(12) United States Patent
Jones et al.

(10) Patent No.: US 10,954,243 B2
(45) Date of Patent: Mar. 23, 2021

(54) SUBSTITUTED HETEROCYCLIC INHIBITORS OF PTPN11

(71) Applicant: NAVIRE PHARMA, INC., Palo Alto, CA (US)

(72) Inventors: Philip Jones, Houston, TX (US); Jason Cross, Pearland, TX (US); Jason Burke, Houston, TX (US); Timothy Mcafoos, Houston, TX (US); Zhijun Kang, Richmond, TX (US)

(73) Assignee: NAVIRE PHARMA, INC., Palo Alto, CA (US)

( * ) Notice: Subject to any disclaimer, the term of this patent is extended or adjusted under 35 U.S.C. 154(b) by 0 days.

(21) Appl. No.: 16/401,047

(22) Filed: May 1, 2019

(65) Prior Publication Data

US 2019/0389867 A1     Dec. 26, 2019

Related U.S. Application Data

(60) Provisional application No. 62/665,818, filed on May 2, 2018, provisional application No. 62/773,915, filed on Nov. 30, 2018.

(51) Int. Cl.
  *C07D 487/04* (2006.01)
  *A61P 35/00* (2006.01)
  *C07D 519/00* (2006.01)

(52) U.S. Cl.
  CPC ............ *C07D 487/04* (2013.01); *A61P 35/00* (2018.01); *C07D 519/00* (2013.01)

(58) Field of Classification Search
  CPC .................................................. C07D 487/04
  See application file for complete search history.

(56) References Cited

U.S. PATENT DOCUMENTS

| | | | |
|---|---|---|---|
| 7,897,607 | B2 | 3/2011 | Gyorkos |
| 10,280,171 | B2 | 5/2019 | Jones et al. |
| 2005/0203091 | A1 | 9/2005 | Arora |
| 2011/0152242 | A1 | 6/2011 | Bayliss et al. |
| 2019/0270746 | A1 | 9/2019 | Jones et al. |
| 2020/0048249 | A1 | 2/2020 | Jones et al. |

FOREIGN PATENT DOCUMENTS

| | | |
|---|---|---|
| CN | 107286150 A | 10/2017 |
| CN | 110143949 A | 8/2019 |
| JP | 2010111624 A | 5/2010 |
| JP | 2011246389 A | 12/2011 |
| WO | 2005028480 A2 | 3/2005 |
| WO | 2005085248 A1 | 9/2005 |
| WO | 2006058074 A1 | 6/2006 |
| WO | 2006063820 A1 | 6/2006 |
| WO | 2008061109 A2 | 5/2008 |
| WO | 2011055911 A1 | 5/2011 |
| WO | 2012106343 A2 | 8/2012 |
| WO | 2013040527 A1 | 3/2013 |
| WO | 2013052263 A2 | 4/2013 |
| WO | 2014047662 A2 | 3/2014 |
| WO | 2014200682 A1 | 12/2014 |
| WO | 2015099481 A1 | 7/2015 |
| WO | 2015107493 A1 | 7/2015 |
| WO | 2015107494 A1 | 7/2015 |
| WO | 2015107495 A1 | 7/2015 |
| WO | 2015190718 A1 | 12/2015 |
| WO | 2016064102 A1 | 4/2016 |
| WO | 2016151501 A1 | 9/2016 |
| WO | 2016203404 A1 | 12/2016 |
| WO | 2016203405 A1 | 12/2016 |
| WO | 2016203406 A1 | 12/2016 |
| WO | 2017156397 A1 | 9/2017 |
| WO | 2017210134 A1 | 12/2017 |
| WO | 2017211303 A1 | 12/2017 |
| WO | 2017216706 A1 | 12/2017 |
| WO | 2018013597 A1 | 1/2018 |
| WO | 2018057884 A1 | 3/2018 |
| WO | 2018081091 A1 | 5/2018 |
| WO | 2018130928 A1 | 7/2018 |
| WO | 2018136264 A1 | 7/2018 |
| WO | 2018136265 A1 | 7/2018 |
| WO | 2018172984 A1 | 9/2018 |
| WO | 2018218133 A1 | 11/2018 |
| WO | 2019051084 A1 | 3/2019 |
| WO | 2019051469 A1 | 3/2019 |
| WO | 2019067843 A1 | 4/2019 |
| WO | 2019075265 A1 | 4/2019 |
| WO | 2019118909 A1 | 6/2019 |
| WO | 2019152454 A1 | 8/2019 |
| WO | 2019158019 A1 | 8/2019 |
| WO | 2019165073 A1 | 8/2019 |
| WO | 2019167000 A1 | 9/2019 |

(Continued)

OTHER PUBLICATIONS

Amarnath, S. et al. (Nov. 30, 2011). "The PDL1-PD1 axis converts human TH1 cells into regulatory T cells," Sci Transl Med 3(111):111ra120.

Anderson, J.N. et al. (Nov. 2001). "Structural and evolutionary relationships among protein tyrosine phosphatase domains," Mol Cell Biol 21(21):7117-7136.

Barr, A.J. et al. (Jan. 23, 2009). "Large-scale structural analysis of the classical human protein tyrosine phosphatome," Cell 136(2):352-363.

Chan, G. et al. (Jun. 2008). "The tyrosine phosphatase Shp2 (PTPN11) in cancer," Cancer Metastasis Rev 27(2):179-192.

Darian, E. et al. (May 2011, e-published Mar. 1, 2011). "Structural mechanism associated with domain opening in gain-of-function mutations in SHP2 phosphatase," Proteins 79(5):1573-1588.

Grossmann, K.S. et al. (2010). "The tyrosine phosphatase Shp2 in development and cancer," Adv Cancer Res 106:53-89.

Huang, W.Q. et al. (2014). "Structure, function, and pathogenesis of SHP2 in developmental disorders and tumorigenesis," Curr Cancer Drug Targets 14(6):567-588.

(Continued)

*Primary Examiner* — Paul V Ward
(74) *Attorney, Agent, or Firm* — Mintz, Levin, Cohn, Ferris, Glovsky & Popeo, P.C.

(57) ABSTRACT

The present invention relates to compounds which may be useful as inhibitors of PTPN11 for the treatment or prevention of cancer and other PTP-mediated diseases. Disclosed herein are new compounds and compounds based on pyrazolopyrazines and their application as pharmaceuticals for the treatment of disease.

18 Claims, No Drawings

(56) References Cited

FOREIGN PATENT DOCUMENTS

| WO | 2019182960 A1 | 9/2019 |
| WO | 2019183364 A1 | 9/2019 |
| WO | 2019183367 A1 | 9/2019 |
| WO | 2019199792 A1 | 10/2019 |
| WO | 2019213318 A1 | 11/2019 |
| WO | 2019233810 A1 | 12/2019 |
| WO | 2020022323 | 1/2020 |
| WO | 2020033828 A1 | 2/2020 |

OTHER PUBLICATIONS

Li, J. et al. (Feb. 1, 2015, e-published Dec. 5, 2014). "PD-1/SHP-2 inhibits Tc1/Th1 phenotypic responses and the activation of T cells in the tumor microenvironment," Cancer Res 75(3):508-518.

Mohi, M.G. et al. (Feb. 2007, e-published Jan. 16, 2007). "The role of Shp2 (PTPN11) in cancer," Curr Opin Genet Dev 17(1):23-30.

Okazaki, T. et al. (Nov. 20, 2001, e-published Nov. 6, 2001). "PD-1 immunoreceptor inhibits B cell receptor-mediated signaling by recruiting src homology 2-domain-containing tyrosine phosphatase 2 to phosphotyrosine," PNAS USA 98(24):13866-13871.

Prahallad, A. et al. (Sep. 29, 2015, e-published Sep. 10, 2015). "PTPN11 is a Central Node in Intrinsic and Acquired Resistance to Targeted Cancer Drugs," Cell Rep 12(12):1978-1985.

Pubchem CID 57384833: Create Date: Jul. 23, 2012; Date accessed: Jun. 19, 2017; p. 3.

Qiu, W. et al. (Mar. 14, 2014). "Structural insights into Noonan/LEOPARD syndrome-related mutants of protein-tyrosine phosphatase SHP2 (PTPN11)," BMC Struct Biol 14:10.

Revesz L. et al., Novel p38a MAP kinase inhibiting scaffolds with oral activity Bioorganic & Medicinal Chemistry Letters; 2006), 16(2), 262-266.

Tajan, M. et al. (Oct. 2015, e-published Sep. 2, 2015). "SHP2 sails from physiology to pathology," Eur J Med Genet 58(10):509-525.

Yokosuka, T. et al. (Jun. 4, 2012, e-published May 28, 2012). "Programmed cell death 1 forms negative costimulatory microclusters that directly inhibit T cell receptor signaling by recruiting phosphatase SHP2," J Exp Med 209(6):1201-1217.

Yu, Z-H. et al. (Apr. 12, 2013, e-published Mar. 1, 2013). "Structural and mechanistic insights into LEOPARD syndrome-associated SHP2 mutations," J Biol Chem 288(15):10472-10482.

International Search Report and Written Opinion for PCT/US2017/034806 dated Sep. 6, 2017, 9 pages.

International Search Report and Written Opinion for PCT/US2019/030277 dated Jul. 26, 2019, 12 pages.

International Search Report and Written Opinion for PCT/US2019/045903 dated Oct. 28, 2019, 12 pages.

SUBSTITUTED HETEROCYCLIC INHIBITORS OF PTPN11

CROSS-REFERENCES TO RELATED APPLICATIONS

This application claims priority to U.S. Provisional Application No. 62/665,818, filed May 2, 2018 and U.S. Provisional Application No. 62/773,915, filed Nov. 30, 2018, each of which is incorporated herein in its entirety and for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Disclosed herein are new compounds and compounds based on pyrazolopyrazines and their application as pharmaceuticals for the treatment of disease. Methods of inhibition of PTPN11 (SHP2) activity in a human or animal subject are also provided for the treatment diseases such as cancer, including leukemia and melanoma, and cancers of the breast, lung, and colon.

Tyrosyl phosphorylation regulates human cellular processes from cell differentiation to growth and apoptosis, and others. Tyrosyl phosphorylation is regulated by protein-tyrosine kinases (PTK) and protein-tyrosine phosphatases (PTP). The breakdown of regulation governed by PTK and PTP activity is thought to lead to cancer. PTK inhibitors have been developed as potential cancer therapeutic agents. Recent studies disclose a possible role for PTPs in cellular regulation as well. (A J Barr et al. *Cell* 2009, 136, 352-363. J N Andersen et al *Mol. Cell. Biol.* 2001, 21, 7117-7136).

Protein-tyrosine phosphatase non-receptor type 11 (PTPN11, also known as Src Homology-2 phosphatase (SHP2)) is a non-receptor protein tyrosine phosphatase encoded by the PTPN11 gene. This PTP contains two tandem Src homology-2 (SH2) domains, which function as phospho-tyrosine binding domains, a catalytic domain, and a C-terminal tail. In the basal state the protein typically exists in an inactive, self-inhibited conformation with the N-terminal SH2 domain blocking the active site. When stimulated by signal transduction mediated by cytokines and growth factor binding of phosphorylated proteins to the SH2 domains the auto-inhibition is relieved, this makes the active site available for dephosphorylation of PTPN11 substrates (MG Mohl, B G Neel, *Curr. Opin. Genetics Dev.* 2007, 17, 23-30. K S Grossmann, *Adv. Cancer Res.* 2010, 106, 53-89. W. Q. Huang et. al. *Curr. Cancer Drug Targets* 2014, 14, 567-588. C. Gordon et. al. *Cancer Metastasis Rev.* 2008, 27, 179-192.).

Germ-line and somatic mutations in PTPN11 have been reported in several human diseases resulting in gain-of-function in the catalytic activity, including Noonan Syndrome and Leopard Syndrome; as well as multiple cancers such as juvenile myelomonocytic leukemia, neuroblastoma, myelodysplastic syndrome, B cell acute lymphoblastic leukemia/lymphoma, melanoma, acute myeloid leukemia and cancers of the breast, lung and colon (M G Mohl, B G Neel, *Curr. Opin. Genetics Dev.* 2007, 17, 23-30). Recent studies have demonstrated that single PTPN11 mutations are able to induce Noonan syndrome, JMML-like myeloproliferative disease and acute leukemia in mice. These mutations disrupt the auto-inhibition between the N—SH2 domains and the catalytic site allowing constitutive access of substrates to the catalytic site of the enzyme (E. Darian et al, *Proteins,* 2011, 79, 1573-1588. Z-H Yu et al, *JBC,* 2013, 288, 10472, W Qiu et al *BMC Struct. Biol.* 2014, 14, 10).

PTPN11 is widely expressed in most tissues and plays a regulatory role in various cell signaling events that are important for a diversity of cell functions that includes proliferation, differentiation, cell cycle maintenance, EMT transition, mitogenic activation, metabolic control, transcription regulation, and cell migration, through multiple signaling pathways including the Ras-MAPK, the JAK-STAT or the PI3K-AKT pathways (Taj an, M. et. al. *Eur. J. Medical Genetics,* 2015, 58, 509-525. Prahallad, A. et. al. *Cell Reports,* 2015, 12, 1978-1985).

Additionally there is growing evidence that PTPN11/SHP2 may be implicated in immune evasion during tumorigenesis, and hence a SHP2 inhibitor could stimulate the immune response in cancer patients (*Cancer Res.* 2015 Feb. 1; 75(3):508-18. T Yokosuka T, *J Exp Med.* 2012, 209(6), 1201. S Amarnath *Sci Transl Med.* 2011, 3, 111ra120. T Okazaki, *PNAS* 2001, 98:24, 13866-71).

Novel compounds and pharmaceutical compositions, certain of which have been found to inhibit PTPN11 (SHP2) have been discovered, together with methods of synthesizing and using the compounds including methods for the treatment of PTP-mediated diseases in a patient by administering the compounds.

BRIEF SUMMARY OF THE INVENTION

In certain embodiments of the present invention, compounds have structural Formula I:

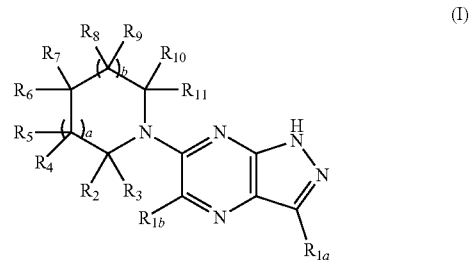

(I)

or a salt or tautomer thereof, wherein the subscripts a and b, and $R_{1a}$, $R_{1b}$, $R_2$, $R_3$, $R_4$, $R_5$, $R_6$, $R_7$, $R_8$, $R_9$, $R_{10}$ and $R_{11}$ are as provided herein.

In certain embodiments, the present invention provides a pharmaceutical composition including a compound having Formula I, together with a pharmaceutically acceptable carrier.

In certain embodiments, the present invention provides methods of inhibition of PTPN11 (SHP2) activity in a human or animal subject for the treatment diseases such as cancer, including leukemia and melanoma, and cancers of the breast, lung, and colon.

BRIEF DESCRIPTION OF THE DRAWINGS

Not applicable

DETAILED DESCRIPTION OF THE INVENTION

Definitions

As used herein, the terms below have the meanings indicated.

When ranges of values are disclosed, and the notation "from $n_1$ . . . to $n_2$" or "between $n_1$ . . . and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—),(—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkynyl" refers to either a straight chain or branched hydrocarbon having at least 2 carbon atoms and at least one triple bond and having the number of carbon atom indicated (i.e., $C_{2-6}$ means to two to six carbons). Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups are optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which is optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term aryloxy as used herein, alone or in combination, refers to an aryl group attached to the parent molecular moiety through an oxy.

The term "carbamate," as used herein, alone or in combination, refers to an ester of carbamic acid (—NHCOO—) which may be attached to the parent molecular moiety from either the nitrogen or acid end, and which is optionally substituted as defined herein.

The term "O-carbamyl" as used herein, alone or in combination, refers to a —OC(O)NRR', group—with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. The term "cycloalkenyl" refers to a cycloalkyl group having one or two double bonds. In certain embodiments, said cycloalkyl (or cycloalkenyl) will comprise from 5 to 7 carbon atoms. Examples of such groups include cyclopropyl, cyclobutyl, cyclopentyl, cyclohexyl, cycloheptyl, cyclobutenyl, cyclopentenyl, cyclohexenyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro, or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms selected from the group consisting of N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom selected from the group consisting of N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each said heteroatom may be independently selected from the group consisting of nitrogen, oxygen, and sulfur. In certain embodiments, said heterocycloalkyl will comprise from 1 to 4 heteroatoms as ring members. In further embodiments, said heterocycloalkyl will comprise from 1 to 2 heteroatoms as ring members. In certain embodiments, said heterocycloalkyl will comprise from 3 to 8 ring members in each ring. In further embodiments, said heterocycloalkyl will comprise from 3 to 7 ring members in each ring. In yet further embodiments, said heterocycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups are optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "iminohydroxy," as used herein, alone or in combination, refers to =N(OH) and =N—O—.

The term "lower amino," as used herein, alone or in combination, refers to —NRR', wherein R and R' are independently selected from the group consisting of hydrogen and lower alkyl, either of which is optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "ring," or equivalently, "cycle," as used herein, in reference to a chemical structure or portion thereof, means a group in which every atom is a member of a common cyclic structure. A ring can be saturated or unsaturated, including aromatic, unless otherwise provided, and may have between 3 and 9 members. If the ring is a heterocycle, it may contain between 1 and 4 heteroatoms or heteroatom-comprising groups selected from the group consisting of B, N, O, S, C(O), S(O)m. Unless specifically prohibited, a ring is optionally substituted.

The terms "sulfonate," "sulfonic acid," and "sulfonic," as used herein, alone or in combination, refer to the —SO$_3$H group and its anion as the sulfonic acid is used in salt formation.

The term "sulfanyl," as used herein, alone or in combination, refers to S.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The term "tautomer", as use herein, alone or in combination, refers to one of two or more isomers that rapidly interconvert. Generally, this interconversion is sufficiently fast so that an individual tautomer is not isolated in the absence of another tautomer. The ratio of the amount of tautomers can be dependent on solvent composition, ionic strength, and pH, as well as other solution parameters. The ratio of the amount of tautomers can be different in a particular solution and in the microenvironment of a biomolecular binding site in said solution. Examples of tautomers that are well known in the art include keto/enol, enamine/imine, and lactam/lactim tautomers. Examples of tautomers that are well known in the art also include 2-hydroxypyridine/2(1H)-pyridone and 2-aminopyridine/2 (1H)-iminopyridone tautomers.

The terms "thia" and "thio," as used herein, alone or in combination, refer to a S group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower haloalkyl, lower haloalkenyl, lower haloalkynyl, lower perhaloalkyl, lower perhaloalkoxy, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which is optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"PTPN11 inhibitor" is used herein to refer to a compound that exhibits an $IC_{50}$ with respect to PTPN11 activity of no more than about 100 µM and more typically not more than about 50 µM, as measured in the PTPN11 assay described generally herein. "$IC_{50}$" is that concentration of inhibitor which reduces the activity of an enzyme (e.g., PTPN11) to half-maximal level. Certain compounds disclosed herein have been discovered to exhibit inhibition against PTPN11. In certain embodiments, compounds will exhibit an $IC_{50}$ with respect to PTPN11 of no more than about 50 µM; in further embodiments, compounds will exhibit an $IC_{50}$ with respect to PTPN11 of no more than about 10 µM; in yet further embodiments, compounds will exhibit an $IC_{50}$ with respect to PTPN11 of not more than about 1 µM; in yet further embodiments, compounds will exhibit an $IC_{50}$ with respect to PTPN11 of not more than about 200 nM, as measured in the PTPN11 assay described herein.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs. Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable.

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methyl amine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid.

LIST OF ABBREVIATIONS

NaOH=sodium hydroxide; M=molar; mL=milliliter; h=hour; min.=minute; HCl=hydrogen chloride; $H_2O$=water; MS=mass spectrometry; ES+=electrospray positive ionization; $^1$H-NMR=proton nuclear magnetic resonance; MHz=megahertz; DMSO-$d_6$=dimethyl sulfoxide deuterated-6; H=hydrogen; rt=room temperature; ° C.=Celsius; $Br_2$=bromine; $NaHSO_3$=sodium bisulfate; NMP=N-Methyl-2-pyrrolidone; MW=microwave; KF=potassium fluoride; Pd(dppf)$Cl_2$=[1,1'-bis(diphenylphosplaino)ferrocene]palladium(10 dichloride; PE petroleum ether; EA=ethyl acetate; $CDCl_3$=deuterated chloroform; MeOH=methanol; $D_2O$=deuterated water; HPLC=high pressure liquid chromatography; DMSO=dimethyl sulfoxide; MeCN=acetonitrile; NIS=N-iodosuccinimide; DMF=dimethylformamide; $K_3PO_4$=potassium phosphate, tribasic; $N_2$=nitrogen; TBDMS=TBS=tert-butyldimethylsilyl; TFA=trifluoroacetic acid; DCM=dichloromethane; $K_2CO_3$=potassium carbonate; ul=microliter.

Embodiments

In certain embodiments of the present invention, compounds have structural Formula I:

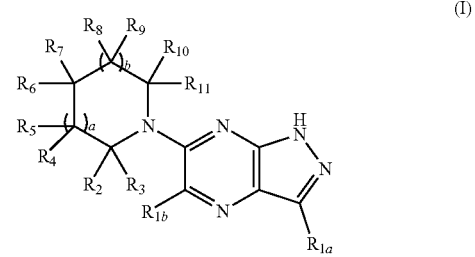

(I)

or a salt or tautomer thereof, wherein:
a is 0 or 1;
b is 0 or 1;
$R_{1a}$ is selected from the group consisting of halo, $C_{6-10}$aryl, $C_{3-8}$cycloalkyl, $C_{3-8}$cycloalkenyl, and a 5-9 membered heteroaryl group containing 1 to 4 heteroatoms or groups independently selected from the group consisting of N, C(O), O, and S; said aryl or heteroaryl of $R_{1a}$ is optionally substituted with 1 to 5 $R_{12}$ groups independently selected from the group consisting of halo, hydroxy, amino, $C_{1-4}$ alkylamino, $C_{1-4}$ dialkylamino, cyano, $C_{1-4}$alkyl, $C_{1-4}$alkoxy, $C_{1-4}$hydroxyalkyl, $C_{1-4}$dihydroxyalkyl, hydroxy$C_{1-4}$alkoxy, dihydroxy$C_{1-4}$alkoxy, $C_{1-4}$haloalkyl, $C_{1-4}$aminoalkyl, $C_{3-8}$cycloalkyl, $C_{3-8}$cycloalkenyl, $NR_{15}C(O)R_{13}$, $NR_{15}C(O)OR_{13}$, $NR_{13}C(O)NR_{15}R_{16}$, $NR_{15}S(O)R_{13}$, $NR_{15}S(O)_2R_{13}$, $C(O)NR_{15}R_{16}$, $S(O)NR_{15}R_{16}$, $S(O)_2NR_{15}R_{16}$, $C(O)R_{13}$, $C(O)OR_{13}$, $OR_{13}$, $SR_{13}$, $S(O)R_{13}$, and $S(O)_2R_{13}$;

$R_{1b}$ is selected from the group consisting of halogen, cyano, $C_{1-6}$ alkyl, $C_{1-6}$ haloalkyl, $C_{1-6}$ hydroxyalkyl, $C_{1-6}$ dihydroxyalkyl, —$CF_2OH$, —CHFOH, —NH—NHR$_{19}$, —NH—OR$_{19}$, —O—NR$_{19}R_{20}$, —NHR$_{19}$, —NHC(O)R$_{19}$, —NHC(O)NHR$_{19}$, —NHS(O)$_2$NHR$_{19}$, —NHS(O)$_2$R$_{19}$, —C(O)OR$_{19}$, —C(O)NR$_{19}R_{20}$, —C(O)NH(CH$_2$)$_n$OH, —C(O)NH(CH$_2$)$_n$R$_{21}$, —C(O)R$_{21}$, —NH$_2$, —OH, —CN, —S(O)$_2$NR$_{19}R_{20}$, $C_3$-$C_8$ cycloalkyl, aryl, heterocyclyl having 1-5 heteroatom ring vertices selected from the group consisting of N, O, S and P, heteroaryl having 1-5 heteroatom ring vertices selected from the group consisting of N, O, S and P; wherein the subscript n is an integer of from 0 to 6; and wherein aryl, heteroaryl, heterocyclyl and cycloalkyl are substituted with 0 to 3 members independently selected from the group consisting of $C_{1-4}$ alkyl, —OH, —NH$_2$, —OR$_{21}$, halogen, cyano and oxo;

$R_2$, $R_3$, $R_{10}$, and $R_{11}$ are independently selected from the group consisting of hydrogen, $C_{1-4}$ alkyl, and $C_{3-8}$cycloalkyl;

$R_4$, $R_5$, $R_8$, and $R_9$ are independently selected from the group consisting of hydrogen, cyano, $C_{1-4}$ alkyl, $C_{1-4}$alkoxy, amino, hydroxy, $C_{3-8}$cycloalkyl, halo, and $C_{1-4}$alkylamino;

$R_6$ is selected from the group consisting of amino, $C_{1-4}$aminoalkyl, and $C_{1-4}$alkylamino;

$R_7$ is selected from the group consisting of hydrogen, cyano, amido, halo, and hydroxy, or is selected from the group consisting of $C_{1-4}$ alkyl, $C_{1-4}$ hydroxyalkyl, $C_{3-6}$ cycloalkyl, phenyl, and 5- or 6-membered heteroaryl, any of which is optionally substituted with one or more $R_{17}$ groups;

or $R_6$ and $R_7$ together with the carbon atom to which they are both attached form a 3- to 7-membered saturated or unsaturated ring that can contain 1 to 3 heteroatoms or groups independently selected from the group consisting of N, C(O), O, and S(O)$_m$, and that is optionally substituted with one $R_{17}$ group, and that is optionally substituted with one or more $R_{18}$ groups;

m is 0, 1, or 2;

any two groups of $R_2$, $R_3$, $R_4$, $R_5$, $R_7$, $R_8$, $R_9$, $R_{10}$ and $R_{11}$ can form a 5- to 6-membered ring, optionally containing a N, O or S heteroatom;

any two groups of $R_2$, $R_4$, $R_6$, $R_8$ and $R_{10}$ can form a direct bond, or a 1 or 2 atom carbon bridge;

$R_{13}$, $R_{15}$, and $R_{16}$ are independently selected from the group consisting of hydrogen, $C_{1-4}$ alkyl, $C_{3-8}$cycloakyl, and 3- to 6-membered heterocyclyl, wherein said alkyl, cycloalkyl and 3- to 6-membered heterocyclyl is optionally substituted by one or more substituents selected from the group consisting of hydroxy, cyano and halo;

each $R_{17}$ and $R_{18}$ is independently selected from the group consisting of amino, halo, hydroxy, cyano, trifluoromethyl, trifluoromethoxy, $C_{1-4}$ alkyl, and $C_{1-4}$ alkoxy;

each $R_{19}$ and $R_{20}$ is independently selected from the group consisting of H, $C_{1-6}$ alkyl, $C_{1-6}$ haloalkyl, $C_{1-6}$ hydroxyalkyl, $C_{2-6}$ alkenyl, $C_{2-6}$ alkynyl and $C_{3-6}$cycloalkyl; and each $R_{21}$ is independently selected from the group consisting of H, —OH, $C_{1-6}$ alkyl, $C_{1-6}$ haloalkyl, $C_{1-6}$ hydroxyalkyl, $C_{2-6}$ alkenyl, $C_{2-6}$ alkynyl and $C_{3-6}$cycloalkyl.

Certain compounds disclosed herein may possess useful PTPN11 inhibiting activity, and may be used in the treatment or prophylaxis of a disease or condition in which PTPN11 plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting PTPN11. Other embodiments provide methods for treating a PTPN11-mediated disorder in a patient in need of such treatment, comprising administering to said patient a therapeutically effective amount of a compound or composition according to the present invention. Also provided is the use of certain compounds disclosed herein for use in the manufacture of a medicament for the treatment of a disease or condition ameliorated by the inhibition of PTPN11.

In certain embodiments, $R_{1b}$ is selected from the group consisting of halogen, cyano, $C_{1-6}$ alkyl, $C_{1-6}$ haloalkyl, $C_{1-6}$ hydroxyalkyl, $C_{1-6}$ dihydroxyalkyl, —CF$_2$OH, —CHFOH, $C_3$-$C_8$ cycloalkyl, 5- or 6-membered heterocyclyl having 1-3 heteroatom ring vertices selected from the group consisting of N, O and S, 5- or 6-membered heteroaryl having 1-4 heteroatom ring vertices selected from the group consisting of N, O, and S; wherein heteroaryl, heterocyclyl and cycloalkyl are substituted with 0 to 3 members independently selected from the group consisting of $C_{1-4}$ alkyl, —OH, —NH$_2$, —OR$_{21}$, halogen, cyano and oxo.

In certain embodiments, $R_{1b}$ is halogen, cyano, $C_{1-6}$ alkyl, $C_{1-6}$ haloalkyl, $C_{1-6}$ hydroxyalkyl, $C_{1-6}$dihydroxyalkyl, —CF$_2$OH, —CHFOH, or $C_3$-$C_8$ cycloalkyl. In certain embodiments, $R_{1b}$ is halogen, $C_{1-6}$ alkyl, $C_{1-6}$haloalkyl, $C_{1-6}$ hydroxyalkyl, $C_{1-6}$ dihydroxyalkyl, —CF$_2$OH, or —CHFOH. In certain embodiments, $R_{1b}$ is halogen, $C_{1-6}$ alkyl, or $C_{1-6}$haloalkyl. In certain embodiments, $R_{1b}$ is $C_{1-6}$ hydroxyalkyl, $C_{1-6}$dihydroxyalkyl, —CF$_2$OH, or —CHFOH. In certain embodiments, $R_{1b}$ is halogen or $C_{1-6}$ alkyl. In certain embodiments, $R_{1b}$ is halogen. In certain embodiments, $R_{1b}$ is $C_{1-6}$ alkyl. In certain embodiments, $R_{1b}$ is $C_{1-6}$ hydroxyalkyl. In certain embodiments, $R_{1b}$ is chloro, methyl, CH$_2$F, CHF$_2$, or CH$_2$OH. In certain embodiments, $R_{1b}$ is chloro. In certain embodiments, $R_{1b}$ is methyl. In certain embodiments, $R_{1b}$ is CH$_2$OH.

In certain embodiments, $R_{1b}$ is 5- or 6-membered heterocyclyl having 1-3 heteroatom ring vertices selected from the group consisting of N, O and S; or 5- or 6-membered heteroaryl having 1-4 heteroatom ring vertices selected from the group consisting of N, O, and S, wherein heteroaryl and heterocyclyl are substituted with 0 to 2 members independently selected from the group consisting of $C_{1-4}$ alkyl, —OH, —NH$_2$, $C_{1-4}$ alkoxy, halogen, cyano and oxo.

In certain embodiments, $R_{1a}$ is $C_{6-10}$aryl or a 5- to 9-membered heteroaryl group containing 1 to 4 heteroatoms or groups independently selected from the group consisting of N, C(O), O, and S; said aryl or heteroaryl of $R_{1a}$ is optionally substituted with 1 to 5 $R_{12}$ groups independently selected from the group consisting of halo, hydroxy, alkoxy, amino, $C_{1-4}$ alkylamino, $C_{1-4}$dialkylamino, cyano, $C_{1-4}$alkyl, $C_{1-4}$hydroxyalkyl, $C_{1-4}$haloalkyl, $C_{1-4}$ aminoalkyl, $C_{3-8}$cycloalkyl, $C_{3-8}$cycloalkenyl, $NR_{15}C(O)R_{13}$, $NR_{15}C(O)OR_{13}$, $NR_{13}C(O)NR_{15}R_{16}$, $NR_{15}S(O)R_{13}$, $NR_{15}S(O)_2R_{13}$, $C(O)NR_{15}R_{16}$, $S(O)NR_{15}R_{16}$, $S(O)_2NR_{15}R_{16}$, $C(O)R_{13}$, $C(O)OR_{13}$, $SR_{13}$, $S(O)R_{13}$, and $S(O)_2R_{13}$; and $R_{13}$, $R_{15}$, and $R_{16}$ are independently selected from the group consisting of hydrogen, $C_{1-4}$ alkyl, and $C_{3-8}$cycloakyl, wherein said alkyl or cycloalkyl is optionally substituted by one or more substituents selected from the group consisting of hydroxy, cyano and halo.

In certain embodiments, $R_{1a}$ is $C_{6-10}$aryl or a 5- to 9-membered heteroaryl group containing 1 to 4 heteroatoms or groups independently selected from the group consisting of N, C(O), O, and S; said aryl or heteroaryl of $R_{1a}$ is optionally substituted with 1 to 5 $R_{12}$ groups independently selected from the group consisting of halo, hydroxy, amino, $C_{1-4}$ alkylamino, $C_{1-4}$ dialkylamino, $C_{1-4}$alkyl, $C_{1-4}$alkoxy, $C_{1-4}$ haloalkyl, and $C_{1-4}$aminoalkyl.

In certain embodiments, $R_{1a}$ is $C_{6-10}$ aryl or a 5- to 9-membered heteroaryl group containing 1 to 4 heteroatoms or groups independently selected from the group consisting of N, C(O), O, and S; said aryl or heteroaryl of $R_{1a}$ is optionally substituted with 1 to 5 $R_{12}$ groups independently selected from the group consisting of halo, hydroxy, amino, $C_{1-4}$ alkylamino, $C_{1-4}$alkyl, $C_{1-4}$alkoxy, and $C_{1-4}$haloalkyl.

In certain embodiments, $R_2$, $R_3$, $R_{10}$, and $R_{11}$ are independently hydrogen or $C_{1-4}$alkyl. In certain embodiments, $R_2$, $R_3$, $R_{10}$, and $R_{11}$ are each hydrogen.

In certain embodiments, $R_4$, $R_5$, $R_8$, and $R_9$ are independently selected from the group consisting of hydrogen, $C_{1-4}$alkyl, $C_{1-4}$alkoxy, amino, hydroxy, $C_{3-8}$cycloalkyl, and $C_{1-4}$ alkylamino. In certain embodiments, $R_4$, $R_5$, $R_8$, and $R_9$ are independently hydrogen or $C_{1-4}$alkyl. In certain embodiments, $R_4$, $R_5$, $R_8$, and $R_9$ are each hydrogen.

In certain embodiments, $R_{1a}$ is $C_{6-10}$ aryl or a 5- to 9-membered heteroaryl group containing 1 to 4 heteroatoms or groups independently selected from the group consisting of N, C(O), O, and S; said aryl or heteroaryl of $R_{1a}$ is optionally substituted with 1 to 5 $R_{12}$ groups independently selected from the group consisting of halo, hydroxy, amino, $C_{1-4}$ alkylamino, $C_{1-4}$ dialkylamino, $C_{1-4}$alkyl, $C_{1-4}$alkoxy, $C_{1-4}$haloalkyl, and $C_{1-4}$aminoalkyl; and $R_4$, $R_5$, $R_8$, and $R_9$ are independently selected from the group consisting of hydrogen, $C_{1-4}$ alkyl, $C_{1-4}$alkoxy, amino, hydroxy, $C_{3-8}$cycloalkyl, and $C_{1-4}$alkylamino.

In certain embodiments, $R_2$, $R_3$, $R_4$, $R_5$, $R_8$, $R_9$, $R_{10}$ and $R_{11}$ are each hydrogen.

In certain embodiments, $R_6$ and $R_7$ together with the carbon atom to which they are both attached form a 3- to 7-membered saturated or unsaturated ring that can contain 1 to 3 heteroatoms or groups independently selected from the group consisting of N, C(O), O, and $S(O)_m$, and that is optionally substituted with one $R_{17}$ group, and that is optionally substituted with one or more $R_{18}$ groups.

In certain embodiments, $R_6$ and $R_7$ together with the carbon atom to which they are both attached forms a 3- to 7-membered cycloalkyl ring that is optionally substituted with one $R_{17}$ group, and that is optionally substituted with one or more $R_{18}$ groups.

In certain embodiments, $R_6$ and $R_7$ together with the carbon atom to which they are both attached forms a 3- to 7-membered heterocycloalkyl ring that is optionally substituted with one $R_{17}$ group, and that is optionally substituted with one or more $R_{18}$ groups.

In certain embodiments, $R_6$ and $R_7$ together with the carbon atom to which they are both attached forms a 3- to 7-membered heterocycloalkyl ring that is optionally substituted with one $R_{17}$ group, and that is optionally substituted with one $R_{18}$ group.

In certain embodiments, $R_6$ and $R_7$ together with the carbon atom to which they are both attached forms a 3- to 7-membered heterocycloalkyl ring that is substituted with one $R_{17}$ group, and that is substituted with one $R_{18}$ group.

In certain embodiments, $R_6$ and $R_7$ together with the carbon atom to which they are both attached forms a 3- to 7-membered heterocycloalkyl ring that is optionally substituted with one $R_{17}$ group.

In certain embodiments, $R_6$ and $R_7$ together with the carbon atom to which they are both attached form a 3- to 6-membered heterocycloalkyl ring that is optionally substituted with one $R_{17}$ group, and that is optionally substituted with one or more $R_{18}$ groups.

In certain embodiments, $R_6$ and $R_7$ together with the carbon atom to which they are both attached form a 3- to 6-membered heterocycloalkyl ring that is optionally substituted with one $R_{17}$ group, and that is optionally substituted with one $R_{18}$ group.

In certain embodiments, $R_6$ and $R_7$ together with the carbon atom to which they are both attached form a 3- to 6-membered heterocycloalkyl ring that is substituted with one $R_{17}$ group, and that is substituted with one $R_{18}$ group.

In certain embodiments, $R_6$ and $R_7$ together with the carbon atom to which they are both attached form a 3- to 6-membered heterocycloalkyl ring that is optionally substituted with one $R_{17}$ group.

In certain embodiments, $R_6$ is selected from the group consisting of amino, $C_{1-4}$ aminoalkyl, and methylamino. In certain embodiments, $R_6$ is amino or $C_{1-4}$aminoalkyl. In certain embodiments, $R_6$ is amino, aminomethyl, or methylamino. In certain embodiments, $R_6$ is amino or aminomethyl. In certain embodiments, $R_6$ is amino. In certain embodiments, $R_6$ is aminomethyl.

In certain embodiments, $R_7$ is selected from the group consisting of hydroxyl, $C_{1-4}$ alkyl, $C_{1-4}$ hydroxyalkyl, $C_{3-6}$cycloalkyl, phenyl, and 5- or 6-membered heteroaryl, any of which is optionally substituted with one or more $R_{17}$ groups. In certain embodiments, $R_7$ is selected from the group consisting of hydroxy, $C_{1-4}$ alkyl, $C_{1-4}$hydroxyalkyl, $C_{3-6}$cycloalkyl, phenyl, and 5- or 6-membered heteroaryl. In certain embodiments, $R_7$ is hydroxy, $C_{1-4}$ alkyl, or $C_{1-4}$hydroxyalkyl. In certain embodiments, $R_7$ is $C_{1-4}$alkyl. In certain embodiments, $R_7$ is methyl.

In certain embodiments, $R_6$ is $C_{1-4}$aminoalkyl; and $R_7$ is selected from the group consisting of hydroxy, $C_{1-4}$ alkyl, $C_{1-4}$hydroxyalkyl, $C_{3-6}$cycloalkyl, phenyl, and 5- or 6-membered heteroaryl, any of which is optionally substituted with one or more $R_{17}$ groups.

In certain embodiments, $R_6$ is aminomethyl; and $R_7$ is selected from the group consisting of hydroxy, $C_{1-4}$ alkyl, $C_{1-4}$hydroxyalkyl, $C_{3-6}$cycloalkyl, phenyl, and 5- or 6-membered heteroaryl.

In certain embodiments, $R_6$ is amino; and $R_7$ is selected from the group consisting of amido, $C_{1-4}$ alkyl, $C_{1-4}$hydroxyalkyl, $C_{3-6}$ cycloalkyl, phenyl, and 5- or 6-membered heteroaryl, any of which is optionally substituted with one or more $R_{17}$ groups.

In certain embodiments, $R_6$ is amino; and $R_7$ is $C_{1-4}$hydroxyalkyl. In certain embodiments, $R_6$ is amino; and $R_7$ is $C_{1-4}$ alkyl. In certain embodiments, $R_6$ is amino; and $R_7$ is methyl.

In any of the above embodiments, the amido of $R_7$ may specifically be $C(O)NH_2$.

In certain embodiments, $R_{1a}$ is $C_{6-10}$ aryl or a 5- to 9-membered heteroaryl group containing 1 to 4 heteroatoms or groups independently selected from the group consisting of N, C(O), O, and S; said aryl or heteroaryl of $R_{1a}$ is optionally substituted with 1 to 5 $R_{12}$ groups independently selected from the group consisting of halo, hydroxy, amino, $C_{1-4}$ alkylamino, $C_{1-4}$ dialkylamino, $C_{1-4}$ alkyl, $C_{1-4}$ alkoxy, $C_{1-4}$ haloalkyl, and $C_{1-4}$aminoalkyl; $R_6$ is selected from the group consisting of amino, $C_{1-4}$ aminoalkyl, and $C_{1-4}$ alkylamino; and $R_7$ is selected from the group consisting of hydrogen, cyano, amido, halo, and hydroxy, or is selected from the group consisting of $C_{1-4}$ alkyl, $C_{1-4}$hydroxyalkyl, $C_{3-6}$ cycloalkyl, phenyl, and 5- or 6-membered heteroaryl, any of which is optionally substituted with one or more $R_{17}$ groups.

In certain embodiments, $R_{1a}$ is $C_{6-10}$aryl or a 5- to 9-membered heteroaryl group containing 1 to 4 heteroatoms or groups independently selected from the group consisting of N, C(O), O, and S; said aryl or heteroaryl of $R_{1a}$ is optionally substituted with 1 to 5 $R_{12}$ groups independently selected from the group consisting of halo, hydroxy, amino, $C_{1-4}$ alkylamino, $C_{1-4}$ alkyl, $C_{1-4}$alkoxy, and $C_{1-4}$haloalkyl; $R_6$ is selected from the group consisting of amino, $C_{1-4}$ aminoalkyl, and $C_{1-4}$ alkylamino; $R_7$ is selected from the group consisting of hydrogen, halo, and hydroxy, or is selected from the group consisting of $C_{1-4}$ alkyl, $C_{1-4}$hydroxyalkyl, $C_{3-6}$cycloalkyl, phenyl, and 5- or 6-membered heteroaryl, any of which is optionally substituted with one or more $R_{17}$ groups.

In certain embodiments, $R_{1a}$ is $C_{6-10}$aryl or a 5- to 9-membered heteroaryl group containing 1 to 4 heteroatoms or groups independently selected from the group consisting of N, C(O), O, and S; said aryl or heteroaryl of $R_{1a}$ is optionally substituted with 1 to 5 $R_{12}$ groups independently selected from the group consisting of halo, hydroxy, amino, $C_{1-4}$ alkylamino, $C_{1-4}$ dialkylamino, $C_{1-4}$ alkyl, $C_{1-4}$ alkoxy, $C_{1-4}$ haloalkyl, and $C_{1-4}$aminoalkyl; $R_6$ and $R_7$ together with the carbon atom to which they are both attached form a 3- to 7-membered saturated or unsaturated ring that can contain 1 to 3 heteroatoms or groups independently selected from the group consisting of N, C(O), O, and S(O)m, and that is optionally substituted with one $R_{17}$ group, and that is optionally substituted with one or more $R_{18}$ groups.

In certain embodiments, $R_{1a}$ is $C_{6-10}$aryl or a 5- to 9-membered heteroaryl group containing 1 to 4 heteroatoms or groups independently selected from the group consisting of N, C(O), O, and S; said aryl or heteroaryl of $R_{1a}$ is optionally substituted with 1 to 5 $R_{12}$ groups independently selected from the group consisting of halo, hydroxy, amino, $C_{1-4}$ alkylamino, $C_{1-4}$ alkyl, $C_{1-4}$alkoxy, and $C_{1-4}$haloalkyl; $R_6$ and $R_7$ together with the carbon atom to which they are both attached form a 3- to 7-membered saturated or unsaturated ring that can contain 1 to 3 heteroatoms or groups independently selected from the group consisting of N, C(O), O, and S(O)m, and that is optionally substituted with one $R_{17}$ group, and that is optionally substituted with one or more $R_{18}$ groups.

In certain embodiments, $R_{1a}$ is $C_{6-10}$aryl or a 5- to 9-membered heteroaryl group containing 1 to 4 heteroatoms or groups independently selected from the group consisting of N, C(O), O, and S; said aryl or heteroaryl of $R_{1a}$ is optionally substituted with 1 to 5 $R_{12}$ groups independently selected from the group consisting of halo, hydroxy, amino, $C_{1-4}$ alkylamino, $C_{1-4}$ dialkylamino, $C_{1-4}$ alkyl, $C_{1-4}$ alkoxy, $C_{1-4}$ haloalkyl, and $C_{1-4}$ aminoalkyl; $R_6$ and $R_7$ together with the carbon atom to which they are both attached form a 3- to 7-membered heterocycloalkyl ring that is optionally substituted with one $R_{17}$ group, and that is optionally substituted with one or more $R_{18}$ groups.

In certain embodiments, $R_{1a}$ is $C_{6-10}$aryl or a 5- to 9-membered heteroaryl group containing 1 to 4 heteroatoms or groups independently selected from the group consisting of N, C(O), O, and S; said aryl or heteroaryl of $R_{1a}$ is optionally substituted with 1 to 5 $R_{12}$ groups independently selected from the group consisting of halo, hydroxy, amino, $C_{1-4}$ alkylamino, $C_{1-4}$ alkyl, $C_{1-4}$alkoxy, and $C_{1-4}$haloalkyl; $R_6$ and $R_7$ together with the carbon atom to which they are both attached form a 3- to 7-membered heterocycloalkyl ring that is optionally substituted with one $R_{17}$ group, and that is optionally substituted with one or more $R_{18}$ groups.

In certain embodiments, each $R_{17}$ is independently selected from the group consisting of amino, halo, hydroxy, and cyano. In certain embodiments, each $R_{17}$ is independently selected from the group consisting of amino, hydroxy, and cyano. In certain embodiments, each $R_{17}$ is selected from the group consisting of amino, halo, and hydroxy. In certain embodiments, each $R_{17}$ is amino.

In certain embodiments, $R_{1a}$ is $C_{6-10}$aryl or a 5- to 9-membered heteroaryl group containing 1 to 4 heteroatoms or groups independently selected from the group consisting of N, C(O), O, and S; said aryl or heteroaryl of $R_{1a}$ is optionally substituted with 1 to 5 $R_{12}$ groups independently selected from the group consisting of halo, hydroxy, amino, $C_{1-4}$ alkylamino, $C_{1-4}$dialkylamino, $C_{1-4}$alkyl, $C_{1-4}$alkoxy, $C_{1-4}$haloalkyl, and $C_{1-4}$aminoalkyl; and $R_{17}$ is selected from the group consisting of amino, halo, and hydroxy.

In certain embodiments, $R_{1a}$ is $C_{6-10}$aryl or a 5- to 9-membered heteroaryl group containing 1 to 4 heteroatoms or groups independently selected from the group consisting of N, C(O), O, and S; said aryl or heteroaryl of $R_{1a}$ is optionally substituted with 1 to 5 $R_{12}$ groups independently selected from the group consisting of halo, hydroxy, amino, $C_{1-4}$ alkylamino, $C_{1-4}$alkoxy, and $C_{1-4}$haloalkyl; and $R_{17}$ is selected from the group consisting of amino, halo, and hydroxy.

In certain embodiments, each $R_{18}$ is independently selected from the group consisting of halo, hydroxy, cyano, and $C_{1-4}$ alkyl. In certain embodiments, each $R_{18}$ is halo. In certain embodiments, each $R_{18}$ is $C_{1-4}$alkyl. In certain embodiments, each $R_{18}$ is methyl.

In certain embodiments, $R_{1a}$ is $C_{6-10}$ aryl or a 5-9 membered heteroaryl group containing 1 to 4 heteroatoms or groups independently selected from the group consisting of N, C(O), O, and S; and said aryl or heteroaryl of $R_{1a}$ is optionally substituted with 1 to 5 $R_{12}$ groups independently selected from the group consisting of halo, hydroxy, amino, $C_{1-4}$ alkylamino, cyano, $C_{1-4}$alkyl, and $C_{1-4}$alkoxy.

In certain embodiments, $R_{1a}$ is selected from the group consisting of:

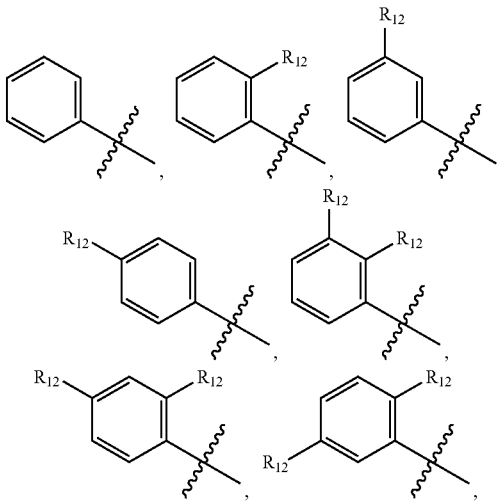

-continued

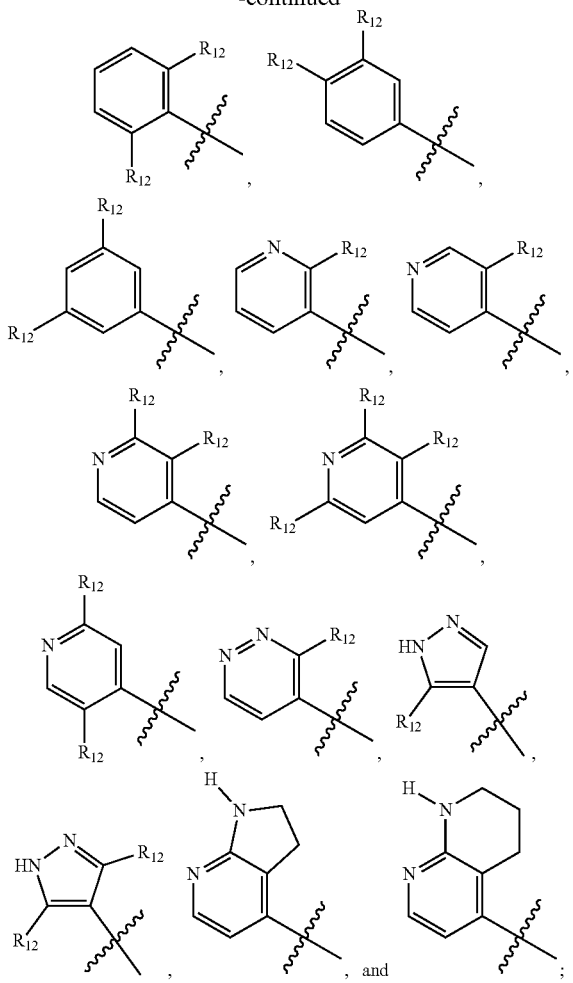

and each $R_{12}$ is independently selected from the group consisting of halo, hydroxy, amino, $C_{1-4}$ alkylamino, $C_{1-4}$dialkylamino, cyano, $C_{1-4}$alkyl, and $C_{1-4}$alkoxy.

In certain embodiments, $R_{1a}$ is selected from the group consisting of:

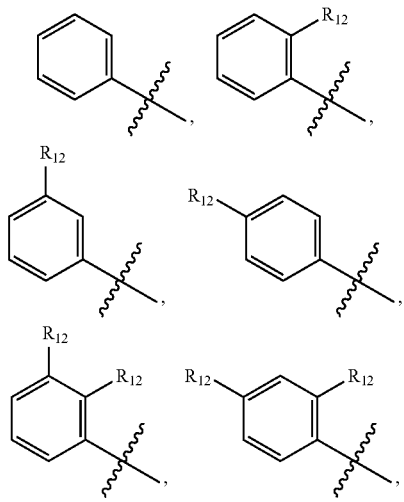

-continued

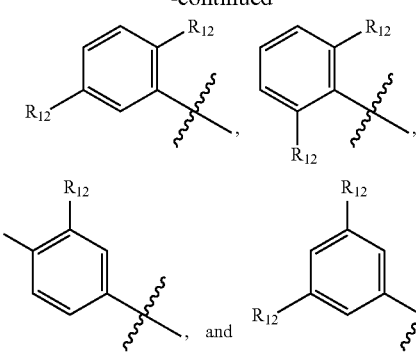

and each $R_{12}$ is independently selected from the group consisting of halo, hydroxy, amino, $C_{1-4}$ alkylamino, $C_{1-4}$dialkylamino, cyano, $C_{1-4}$alkyl, and $C_{1-4}$alkoxy.

In certain embodiments, $R_{1a}$ is selected from the group consisting of:

and each $R_{12}$ is independently selected from the group consisting of halo, hydroxy, amino, $C_{1-4}$ alkylamino, $C_{1-4}$dialkylamino, cyano, $C_{1-4}$alkyl, and $C_{1-4}$alkoxy.

In certain embodiments, $R_{1a}$ is selected as above, wherein each $R_{12}$ is independently selected from the group consisting of halo, hydroxy, amino, $C_{1-4}$ alkylamino, dimethylamino, $C_{1-4}$ alkyl, and $C_{1-4}$ alkoxy. In certain embodiments, $R_{1a}$ is selected as above, wherein each $R_{12}$ is independently halo, amino, or $C_{1-4}$alkylamino. In certain embodiments, $R_{1a}$ is selected as above, wherein each $R_{12}$ is independently halo, amino, methylamino, or ethylamino. In certain embodiments, $R_{1a}$ is selected as above, wherein each $R_{12}$ is independently halo, methylamino, or ethylamino.

In certain embodiments, $R_{1a}$ is selected from the group consisting of pyridyl, piperazinyl, pyrimidinyl, pyrazolyl, and pyridazinyl. In certain embodiments, $R_{1a}$ is pyridyl.

In certain embodiments, $R_{1a}$ is phenyl.

In certain embodiments, compounds have structural Formula II:

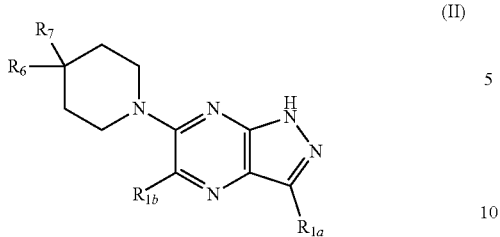 (II)

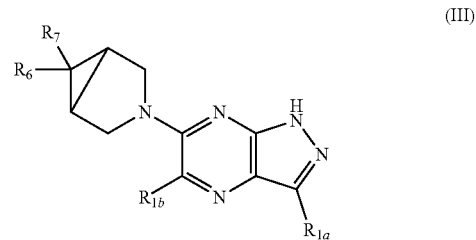 (III)

or a salt or tautomer thereof, wherein:

$R_{1a}$ is selected from the group consisting of halo, $C_{6-10}$aryl, $C_{3-8}$cycloalkyl, $C_{3-8}$cycloalkenyl, and a 5-9 membered heteroaryl group containing 1 to 4 heteroatoms or groups independently selected from the group consisting of N, C(O), O, and S; said aryl or heteroaryl of $R_{1a}$ is optionally substituted with 1 to 5 $R_{12}$ groups independently selected from the group consisting of halo, hydroxy, amino, $C_{1-4}$ alkylamino, $C_{1-4}$ dialkylamino, cyano, $C_{1-4}$alkyl, $C_{1-4}$alkoxy, $C_{1-4}$hydroxyalkyl, $C_{1-4}$haloalkyl, $C_{1-4}$ aminoalkyl, $C_{3-8}$cycloalkyl, $C_{3-8}$cycloalkenyl, $NR_{15}C(O)R_{13}$, $NR_{15}C(O)OR_{13}$, $NR_{13}C(O)NR_{15}R_{16}$, $NR_{15}S(O)R_{13}$, $NR_{15}S(O)_2R_{13}$, $C(O)NR_{15}R_{16}$, $S(O)NR_{15}R_{16}$, $S(O)_2NR_{15}R_{16}$, $C(O)R_{13}$, $C(O)OR_{13}$, $SR_{13}$, $S(O)R_{13}$, and $S(O)_2R_{13}$;

$R_{1b}$ is selected from the group consisting of the group consisting of halogen, cyano, $C_{1-6}$ alkyl, $C_{1-6}$ haloalkyl, $C_{1-6}$ hydroxyalkyl, $C_{1-6}$ dihydroxyalkyl, —$CF_2OH$, —CHFOH, —NH—NHR$_{19}$, —NH—OR$_{19}$, —O—NR$_{19}R_{20}$, —NHR$_{19}$, —OR$_{19}$, —NHC(O)R$_{19}$, —NHC(O)NHR$_{19}$, —NHS(O)$_2$NHR$_{19}$, —NHS(O)$_2$R$_{19}$, —C(O)OR$_{19}$, —C(O)NR$_{19}R_{20}$, —C(O)NH(CH$_2$)$_n$OH, —C(O)NH(CH$_2$)$_nR_{21}$, —C(O)R$_{21}$, —NH$_2$, —OH, —CN, —S(O)$_2$NR$_{19}R_{20}$, $C_3$-$C_8$ cycloalkyl, aryl, heterocyclyl having 1-5 heteroatom ring vertices selected from the group consisting of N, O, S and P, heteroaryl having 1-5 heteroatom ring vertices selected from the group consisting of N, O, S and P; wherein the subscript n is an integer of from 0 to 6; and wherein aryl, heteroaryl, heterocyclyl and cycloalkyl are substituted with 0 to 3 members independently selected from the group consisting of $C_{1-4}$ alkyl, —OH, —NH$_2$, —OR$_{21}$, halogen, cyano and oxo;

$R_6$ is selected from the group consisting of amino, $C_{1-4}$aminoalkyl, and $C_{1-4}$alkylamino;

$R_7$ is selected from the group consisting of hydrogen, cyano, amido, halo, and hydroxy, or is selected from the group consisting of $C_{1-4}$ alkyl, $C_{1-4}$ hydroxyalkyl, $C_{3-6}$ cycloalkyl, phenyl, and 5- or 6-membered heteroaryl, any of which is optionally substituted with one or more $R_{17}$ groups;

$R_{13}$, $R_{15}$, and $R_{16}$ are independently selected from the group consisting of hydrogen, $C_{1-4}$ alkyl, and $C_{3-8}$cycloakyl, wherein said alkyl or cycloalkyl is optionally substituted by one or more substituents selected from the group consisting of hydroxy, cyano and halo; and each $R_{17}$ is independently selected from the group consisting of amino, halo, hydroxy, cyano, trifluoromethyl, trifluoromethoxy, $C_{1-4}$alkyl, and $C_{1-4}$alkoxy.

In certain embodiments, compounds have structural Formula III:

or a salt or tautomer thereof, wherein:

$R_{1a}$ is selected from the group consisting of halo, $C_{6-10}$aryl, $C_{3-8}$cycloalkyl, $C_{3-8}$cycloalkenyl, and a 5-9 membered heteroaryl group containing 1 to 4 heteroatoms or groups independently selected from the group consisting of N, C(O), O, and S; said aryl or heteroaryl of $R_{1a}$ is optionally substituted with 1 to 5 $R_{12}$ groups independently selected from the group consisting of halo, hydroxy, amino, $C_{1-4}$ alkylamino, $C_{1-4}$ dialkylamino, cyano, $C_{1-4}$alkyl, $C_{1-4}$alkoxy, $C_{1-4}$hydroxyalkyl, $C_{1-4}$haloalkyl, $C_{1-4}$ aminoalkyl, $C_{3-8}$cycloalkyl, $C_{3-8}$cycloalkenyl, $NR_{15}C(O)R_{13}$, $NR_{15}C(O)OR_{13}$, $NR_{13}C(O)NR_{15}R_{16}$, $NR_{15}S(O)R_{13}$, $NR_{15}S(O)_2R_{13}$, $C(O)NR_{15}R_{16}$, $S(O)NR_{15}R_{16}$, $S(O)_2NR_{15}R_{16}$, $C(O)R_{13}$, $C(O)OR_{13}$, $SR_{13}$, $S(O)R_{13}$, and $S(O)_2R_{13}$;

$R_{1b}$ is selected from the group consisting of halogen, cyano, $C_{1-6}$ alkyl, $C_{1-6}$haloalkyl, $C_{1-6}$ hydroxyalkyl, $C_{1-6}$ dihydroxyalkyl, —$CF_2OH$, —CHFOH, —NH—NHR$_{19}$, —NH—OR$_{19}$, —O—NR$_{19}R_{20}$, —NHR$_{19}$, —OR$_{19}$, —NHC(O)R$_{19}$, —NHC(O)NHR$_{19}$, —NHS(O)$_2$NHR$_{19}$, —NHS(O)$_2$R$_{19}$, —C(O)OR$_{19}$, —C(O)NR$_{19}R_{20}$, —C(O)NH(CH$_2$)$_n$OH, —C(O)NH(CH$_2$)$_nR_{21}$, —C(O)R$_{21}$, —NH$_2$, —OH, —CN, —S(O)$_2$NR$_{19}R_{20}$, $C_3$-$C_8$ cycloalkyl, aryl, heterocyclyl having 1-5 heteroatom ring vertices selected from the group consisting of N, O, S and P, heteroaryl having 1-5 heteroatom ring vertices selected from the group consisting of N, O, S and P; wherein the subscript n is an integer of from 0 to 6; and wherein aryl, heteroaryl, heterocyclyl and cycloalkyl are substituted with 0 to 3 members independently selected from the group consisting of $C_{1-4}$ alkyl, —OH, —NH$_2$, —OR$_{21}$, halogen, cyano and oxo;

$R_6$ is selected from the group consisting of amino, $C_{1-4}$aminoalkyl, and $C_{1-4}$alkylamino;

$R_7$ is selected from the group consisting of hydrogen, cyano, amido, halo, and hydroxy, or is selected from the group consisting of $C_{1-4}$ alkyl, $C_{1-4}$ hydroxyalkyl, $C_{3-6}$ cycloalkyl, phenyl, and 5- or 6-membered heteroaryl, any of which is optionally substituted with one or more $R_{17}$ groups;

$R_{13}$, $R_{15}$, and $R_{16}$ are independently selected from the group consisting of hydrogen, $C_{1-4}$ alkyl, and $C_{3-8}$cycloakyl, wherein said alkyl or cycloalkyl is optionally substituted by one or more substituents selected from the group consisting of hydroxy, cyano and halo; and each $R_{17}$ is independently selected from the group consisting of amino, halo, hydroxy, cyano, trifluoromethyl, trifluoromethoxy, $C_{1-4}$alkyl, and $C_{1-4}$alkoxy.

In certain embodiments, compounds have structural Formula IV:

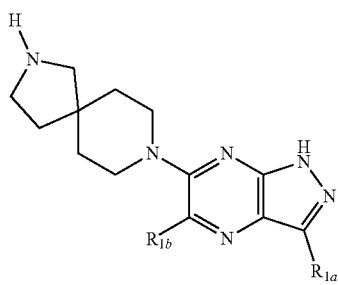

(IV)

or a salt or tautomer thereof, wherein:
$R_{1a}$ is selected from the group consisting of halo, $C_{6-10}$aryl, $C_{3-8}$cycloalkyl, $C_{3-8}$cycloalkenyl, and a 5-9 membered heteroaryl group containing 1 to 4 heteroatoms or groups independently selected from the group consisting of N, C(O), O, and S;
said aryl or heteroaryl of $R_{1a}$ is optionally substituted with 1 to 5 $R_{12}$ groups independently selected from the group consisting of halo, hydroxy, amino, $C_{1-4}$ alkylamino, $C_{1-4}$ dialkylamino, cyano, $C_{1-4}$alkyl, $C_{1-4}$alkoxy, $C_{1-4}$hydroxyalkyl, $C_{1-4}$haloalkyl, $C_{1-4}$ aminoalkyl, $C_{3-8}$cycloalkyl, $C_{3-8}$cycloalkenyl, $NR_{15}C(O)R_{13}$, $NR_{15}C(O)OR_{13}$, $NR_{13}C(O)NR_{15}R_{16}$, $NR_{15}S(O)R_{13}$, $NR_{15}S(O)_2R_{13}$, $C(O)NR_{15}R_{16}$, $S(O)NR_{15}R_{16}$, $S(O)_2NR_{15}R_{16}$, $C(O)R_{13}$, $C(O)OR_{13}$, $SR_{13}$, $S(O)R_{13}$, and $S(O)_2R_{13}$; and
$R_{1b}$ is selected from the group consisting of halogen, cyano, $C_{1-6}$ alkyl, $C_{1-6}$ haloalkyl, $C_{1-6}$ hydroxyalkyl, $C_{1-6}$ dihydroxyalkyl, —$CF_2OH$, —CHFOH, —NH—NHR$_{19}$, —NH—OR$_{19}$, —O—NR$_{19}$R$_{20}$, —NHR$_{19}$, —OR$_{19}$, —NHC(O)R$_{19}$, —NHC(O)NHR$_{19}$, —NHS(O)$_2$NHR$_{19}$, —NHS(O)$_2$R$_{19}$, —C(O)OR$_{19}$, —C(O)NR$_{19}$R$_{20}$, —C(O)NH(CH$_2$)$_n$OH, —C(O)NH(CH$_2$)$_n$R$_{21}$, —C(O)R$_{21}$, —NH$_2$, —OH, —CN, —S(O)$_2$NR$_{19}$R$_{20}$, $C_3$-$C_8$ cycloalkyl, aryl, heterocyclyl having 1-5 heteroatom ring vertices selected from the group consisting of N, O, S and P, heteroaryl having 1-5 heteroatom ring vertices selected from the group consisting of N, O, S and P; wherein the subscript n is an integer of from 0 to 6; and wherein aryl, heteroaryl, heterocyclyl and cycloalkyl are substituted with 0 to 3 members independently selected from the group consisting of $C_{1-4}$ alkyl, —OH, —NH$_2$, —OR$_{21}$, halogen, cyano and oxo;
$R_{13}$, $R_{15}$, and $R_{16}$ are independently selected from the group consisting of hydrogen, $C_{1-4}$ alkyl, and $C_{3-8}$cycloalkyl, wherein said alkyl or cycloalkyl is optionally substituted by one or more substituents selected from the group consisting of hydroxy, cyano and halo.

In certain embodiments, compounds have structural Formula V:

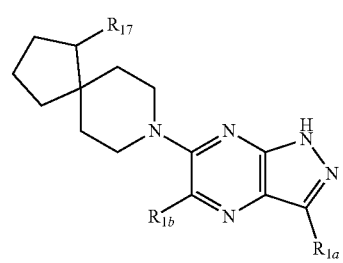

(V)

or a salt or tautomer thereof, wherein:
$R_{1a}$ is selected from the group consisting of halo, $C_{6-10}$aryl, $C_{3-8}$cycloalkyl, $C_{3-8}$cycloalkenyl, and a 5-9 membered heteroaryl group containing 1 to 4 heteroatoms or groups independently selected from the group consisting of N, C(O), O, and S;
said aryl or heteroaryl of $R_{1a}$ is optionally substituted with 1 to 5 $R_{12}$ groups independently selected from the group consisting of halo, hydroxy, amino, $C_{1-4}$ alkylamino, $C_{1-4}$ dialkylamino, cyano, $C_{1-4}$alkyl, $C_{1-4}$alkoxy, $C_{1-4}$hydroxyalkyl, $C_{1-4}$haloalkyl, $C_{1-4}$ aminoalkyl, $C_{3-8}$cycloalkyl, $C_{3-8}$cycloalkenyl, $NR_{15}C(O)R_{13}$, $NR_{15}C(O)OR_{13}$, $NR_{13}C(O)NR_{15}R_{16}$, $NR_{15}S(O)R_{13}$, $NR_{15}S(O)_2R_{13}$, $C(O)NR_{15}R_{16}$, $S(O)NR_{15}R_{16}$, $S(O)_2NR_{15}R_{16}$, $C(O)R_{13}$, $C(O)OR_{13}$, $SR_{13}$, $S(O)R_{13}$, and $S(O)_2R_{13}$;
$R_{1b}$ is selected from the group consisting of halogen, cyano, $C_{1-6}$ alkyl, $C_{1-6}$haloalkyl, $C_{1-6}$hydroxyalkyl, $C_{1-6}$dihydroxyalkyl, —$CF_2OH$, —CHFOH, —NH—NHR$_{19}$, —NH—OR$_{19}$, —O—NR$_{19}$R$_{20}$, —NHR$_{19}$, —OR$_{19}$, —NHC(O)R$_{19}$, —NHC(O)NHR$_{19}$, —NHS(O)$_2$NHR$_{19}$, —NHS(O)$_2$R$_{19}$, —C(O)OR$_{19}$, —C(O)NR$_{19}$R$_{20}$, —C(O)NH(CH$_2$)$_n$OH, —C(O)NH(CH$_2$)$_n$R$_{21}$, —C(O)R$_{21}$, —NH$_2$, —OH, —CN, —S(O)$_2$NR$_{19}$R$_{20}$, $C_3$-$C_8$ cycloalkyl, aryl, heterocyclyl having 1-5 heteroatom ring vertices selected from the group consisting of N, O, S and P, heteroaryl having 1-5 heteroatom ring vertices selected from the group consisting of N, O, S and P; wherein the subscript n is an integer of from 0 to 6; and wherein aryl, heteroaryl, heterocyclyl and cycloalkyl are substituted with 0 to 3 members independently selected from the group consisting of $C_{1-4}$ alkyl, —OH, —NH$_2$, —OR$_{21}$, halogen, cyano and oxo;
$R_{13}$, $R_{15}$, and $R_{16}$ are independently selected from the group consisting of hydrogen, $C_{1-4}$ alkyl, and $C_{3-8}$cycloalkyl, wherein said alkyl or cycloalkyl is optionally substituted by one or more substituents selected from the group consisting of hydroxy, cyano and halo; and
$R_{17}$ is selected from the group consisting of amino, halo, hydroxy, cyano, trifluoromethyl, trifluoromethoxy, $C_{1-4}$ alkyl, and $C_{1-4}$alkoxy.

In certain embodiments, compounds have structural Formula VI:

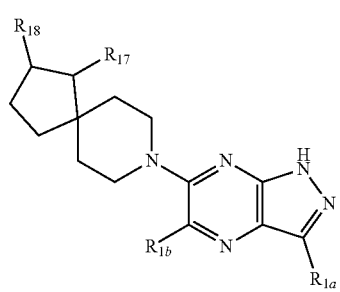

(VI)

or a salt or tautomer thereof, wherein:
$R_{1a}$ is selected from the group consisting of halo, $C_{6-10}$aryl, $C_{3-8}$cycloalkyl, $C_{3-8}$cycloalkenyl, and a 5-9 membered heteroaryl group containing 1 to 4 heteroatoms or groups independently selected from the group consisting of N, C(O), O, and S;
said aryl or heteroaryl of $R_{1a}$ is optionally substituted with 1 to 5 $R_{12}$ groups independently selected from the group consisting of halo, hydroxy, amino, $C_{1-4}$ alkylamino, $C_{1-4}$ dialkylamino, cyano, $C_{1-4}$ alkyl, $C_{1-4}$alkoxy, $C_{1-4}$hydroxyalkyl, $C_{1-4}$haloalkyl, $C_{1-4}$ aminoalkyl, $C_{3-8}$cycloalkyl, $C_{3-8}$cycloalkenyl, $NR_{15}C(O)R_{13}$, $NR_{15}C(O)OR_{13}$, $NR_{13}C(O)NR_{15}R_{16}$, Nit's $S(O)R_{13}$, $NR_{15}S(O)_2R_{13}$, $C(O)NR_{15}R_{16}$, $S(O)NR_{15}R_{16}$, $S(O)_2NR_{15}R_{16}$, $C(O)R_{13}$, $C(O)OR_{13}$, $SR_{13}$, $S(O)R_{13}$, and $S(O)_2R_{13}$;

$R_{1b}$ is selected from the group consisting of halogen, cyano, $C_{1-6}$ alkyl, $C_{1-6}$ haloalkyl, $C_{1-6}$ hydroxyalkyl, $C_{1-6}$ dihydroxyalkyl, —$CF_2OH$, —CHFOH, —NH—$NHR_{19}$, —NH—$OR_{19}$, —O—$NR_{19}R_{20}$, —$NHR_{19}$, —$OR_{19}$, —$NHC(O)R_{19}$, —$NHC(O)NHR_{19}$, —$NHS(O)_2NHR_{19}$, —$NHS(O)_2R_{19}$, —$C(O)OR_{19}$, —$C(O)NR_{19}R_{20}$, —$C(O)NH(CH_2)_nOH$, —$C(O)NH(CH_2)_nR_{21}$, —$C(O)R_{21}$, —$NH_2$, —OH, —CN, —$S(O)_2NR_{19}R_{20}$, $C_3$-$C_8$ cycloalkyl, aryl, heterocyclyl having 1-5 heteroatom ring vertices selected from the group consisting of N, O, S and P, heteroaryl having 1-5 heteroatom ring vertices selected from the group consisting of N, O, S and P; wherein the subscript n is an integer of from 0 to 6; and wherein aryl, heteroaryl, heterocyclyl and cycloalkyl are substituted with 0 to 3 members independently selected from the group consisting of $C_{1-4}$ alkyl, —OH, —$NH_2$, —$OR_{21}$, halogen, cyano and oxo;

$R_{13}$, $R_{15}$, and $R_{16}$ are independently selected from the group consisting of hydrogen, $C_{1-4}$ alkyl, and $C_{3-8}$cycloalkyl, wherein said alkyl or cycloalkyl is optionally substituted by one or more substituents selected from the group consisting of hydroxy, cyano and halo;

$R_{17}$ is selected from the group consisting of amino, halo, hydroxy, cyano, trifluoromethyl, trifluoromethoxy, $C_{1-4}$ alkyl, and $C_{1-4}$alkoxy; and $R_{18}$ is selected from the group consisting of halo, hydroxy, cyano, and $C_{1-4}$ alkyl.

In certain embodiments, compounds have structural Formula VII:

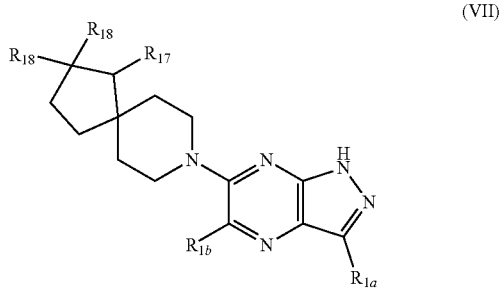

(VII)

or a salt or tautomer thereof, wherein:

$R_{1a}$ is selected from the group consisting of halo, $C_{6-10}$aryl, $C_{3-8}$cycloalkyl, $C_{3-8}$cycloalkenyl, and a 5-9 membered heteroaryl group containing 1 to 4 heteroatoms or groups independently selected from the group consisting of N, C(O), O, and S;

said aryl or heteroaryl of $R_{1a}$ is optionally substituted with 1 to 5 $R_{12}$ groups independently selected from the group consisting of halo, hydroxy, amino, $C_{1-4}$ alkylamino, cyano, $C_{1-4}$alkyl, $C_{1-4}$alkoxy, $C_{1-4}$hydroxyalkyl, $C_{1-4}$ aminoalkyl, $C_{3-8}$cycloalkyl, $C_{3-8}$cycloalkenyl, $NR_{15}C(O)R_{13}$, $NR_{15}C(O)OR_{13}$, $NR_{13}C(O)NR_{15}R_{16}$, $NR_{15}S(O)R_{13}$, $NR_{15}S(O)_2R_{13}$, $C(O)NR_{15}R_{16}$, $S(O)NR_{15}R_{16}$, $S(O)_2NR_{15}R_{16}$, $C(O)R_{13}$, $C(O)OR_{13}$, $SR_{13}$, $S(O)R_{13}$, and $S(O)_2R_{13}$;

$R_{1b}$ is selected from the group consisting of halogen, cyano, $C_{1-6}$ alkyl, $C_{1-6}$haloalkyl, $C_{1-6}$ hydroxyalkyl, $C_{1-6}$ dihydroxyalkyl, —$CF_2OH$, —CHFOH, —NH—$NHR_{19}$, —NH—$OR_{19}$, —O—$NR_{19}R_{20}$, —$NHR_{19}$, —$OR_{19}$, —$NHC(O)R_{19}$, —$NHC(O)NHR_{19}$, —NHS$(O)_2NHR_{19}$, —$NHS(O)_2R_{19}$, —$C(O)OR_{19}$, —$C(O)NR_{19}R_{20}$, —$C(O)NH(CH_2)_nOH$, —$C(O)NH(CH_2)_nR_{21}$, —$C(O)R_{21}$, —$NH_2$, —OH, —CN, —$S(O)_2NR_{19}R_{20}$, $C_3$-$C_8$ cycloalkyl, aryl, heterocyclyl having 1-5 heteroatom ring vertices selected from the group consisting of N, O, S and P, heteroaryl having 1-5 heteroatom ring vertices selected from the group consisting of N, O, S and P; wherein the subscript n is an integer of from 0 to 6; and wherein aryl, heteroaryl, heterocyclyl and cycloalkyl are substituted with 0 to 3 members independently selected from the group consisting of $C_{1-4}$ alkyl, —OH, —$NH_2$, —$OR_{21}$, halogen, cyano and oxo;

$R_{13}$, $R_{15}$, and $R_{16}$ are independently selected from the group consisting of hydrogen, $C_{1-4}$ alkyl, and $C_{3-8}$cycloalkyl, wherein said alkyl or cycloalkyl is optionally substituted by one or more substituents selected from the group consisting of hydroxy, cyano and halo;

$R_{17}$ is selected from the group consisting of amino, halo, hydroxy, cyano, trifluoromethyl, trifluoromethoxy, $C_{1-4}$ alkyl, and $C_{1-4}$alkoxy; and each $R_{18}$ is independently selected from the group consisting of halo, hydroxy, cyano, and $C_{1-4}$ alkyl.

In certain embodiments, compounds have structural Formula VIII:

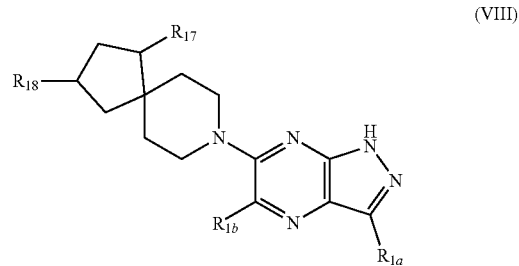

(VIII)

or a salt or tautomer thereof, wherein:

$R_{1a}$ is selected from the group consisting of halo, $C_{6-10}$aryl, $C_{3-8}$cycloalkyl, $C_{3-8}$cycloalkenyl, and a 5-9 membered heteroaryl group containing 1 to 4 heteroatoms or groups independently selected from the group consisting of N, C(O), O, and S;

said aryl or heteroaryl of $R_{1a}$ is optionally substituted with 1 to 5 $R_{12}$ groups independently selected from the group consisting of halo, hydroxy, amino, $C_{1-4}$ alkylamino, $C_{1-4}$ dialkylamino, cyano, $C_{1-4}$alkyl, $C_{1-4}$alkoxy, $C_{1-4}$hydroxyalkyl, $C_{1-4}$haloalkyl, $C_{1-4}$ aminoalkyl, $C_{3-8}$cycloalkyl, $C_{3-8}$cycloalkenyl, $NR_{15}C(O)R_{13}$, $NR_{15}C(O)OR_{13}$, $NR_{13}C(O)NR_{15}R_{16}$, $NR_{15}S(O)R_{13}$, $NR_{15}S(O)_2R_{13}$, $C(O)NR_{15}R_{16}$, $S(O)NR_{15}R_{16}$, $S(O)_2NR_{15}R_{16}$, $C(O)R_{13}$, $C(O)OR_{13}$, $SR_{13}$, $S(O)R_{13}$, and $S(O)_2R_{13}$;

$R_{1b}$ is selected from the group consisting of halogen, cyano, $C_{1-6}$ alkyl, $C_{1-6}$haloalkyl, $C_{1-6}$ hydroxyalkyl, $C_{1-6}$ dihydroxyalkyl, —$CF_2OH$, —CHFOH, —NH—$NHR_{19}$, —NH—$OR_{19}$, —O—$NR_{19}R_{20}$, —$NHR_{19}$, —$OR_{19}$, —$NHC(O)R_{19}$, —$NHC(O)NHR_{19}$, —NHS (O)₂NHR₁₉, —NHS(O)₂R₁₉, —C(O)OR₁₉, —C(O)NR₁₉R₂₀, —C(O)NH(CH₂)ₙOH, —C(O)NH(CH₂)ₙR₂₁, —C(O)R₂₁, —NH₂, —OH, —CN, —S(O)₂NR₁₉R₂₀, C₃-C₈ cycloalkyl, aryl, heterocyclyl having 1-5 heteroatom ring vertices selected from the group consisting of N, O, S and P, heteroaryl having 1-5 heteroatom ring vertices selected from the group consisting of N, O, S and P; wherein the subscript n is an integer of from 0 to 6; and wherein aryl, heteroaryl, heterocyclyl and cycloalkyl are substituted with 0 to 3 members independently selected from the group consisting of C₁₋₄ alkyl, —OH, —NH₂, —OR₂₁, halogen, cyano and oxo;

R₁₃, R₁₅, and R₁₆ are independently selected from the group consisting of hydrogen, C₁₋₄ alkyl, and C₃₋₈cycloakyl, wherein said alkyl or cycloalkyl is optionally substituted by one or more substituents selected from the group consisting of hydroxy, cyano and halo;

R₁₇ is selected from the group consisting of amino, halo, hydroxy, cyano, trifluoromethyl, trifluoromethoxy, C₁₋₄ alkyl, and C₁₋₄alkoxy; and R₁₈ is selected from the group consisting of halo, hydroxy, cyano, and C₁₋₄ alkyl.

In certain embodiments, compounds have structural Formula IX:

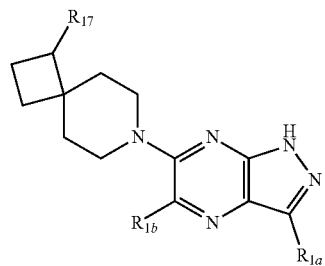

(IX)

or a salt or tautomer thereof, wherein:

R₁ₐ is selected from the group consisting of halo, C₆₋₁₀aryl, C₃₋₈cycloalkyl, C₃₋₈cycloalkenyl, and a 5-9 membered heteroaryl group containing 1 to 4 heteroatoms or groups independently selected from the group consisting of N, C(O), O, and S;

said aryl or heteroaryl of R₁ₐ is optionally substituted with 1 to 5 R₁₂ groups independently selected from the group consisting of halo, hydroxy, amino, C₁₋₄ alkylamino, C₁₋₄ dialkylamino, cyano, C₁₋₄alkyl, C₁₋₄alkoxy, C₁₋₄hydroxyalkyl, C₁₋₄haloalkyl, C₁₋₄ aminoalkyl, C₃₋₈cycloalkyl, C₃₋₈cycloalkenyl, NR₁₅C(O)R₁₃, NR₁₅C(O)OR₁₃, NR₁₃C(O)NR₁₅R₁₆, NR₁₅S(O)R₁₃, NR₁₅S(O)₂R₁₃, C(O)NR₁₅R₁₆, S(O)NR₁₅R₁₆, S(O)₂NR₁₅R₁₆, C(O)R₁₃, C(O)OR₁₃, SR₁₃, S(O)R₁₃, and S(O)₂R₁₃;

R₁ᵦ is selected from the group consisting of halogen, cyano, C₁₋₆ alkyl, C₁₋₆haloalkyl, C₁₋₆ hydroxyalkyl, C₁₋₆ dihydroxyalkyl, —CF₂OH, —CHFOH, —NH—NHR₁₉, —NH—OR₁₉, —O—NR₁₉R₂₀, —NHR₁₉, —OR₁₉, —NHC(O)R₁₉, —NHC(O)NHR₁₉, —NHS(O)₂NHR₁₉, —NHS(O)₂R₁₉, —C(O)OR₁₉, —C(O)NR₁₉R₂₀, —C(O)NH(CH₂)ₙOH, —C(O)NH(CH₂)ₙR₂₁, —C(O)R₂₁, —NH₂, —OH, —CN, —S(O)₂NR₁₉R₂₀, C₃-C₈ cycloalkyl, aryl, heterocyclyl having 1-5 heteroatom ring vertices selected from the group consisting of N, O, S and P, heteroaryl having 1-5 heteroatom ring vertices selected from the group consisting of N, O, S and P; wherein the subscript n is an integer of from 0 to 6; and wherein aryl, heteroaryl, heterocyclyl and cycloalkyl are substituted with 0 to 3 members independently selected from the group consisting of C₁₋₄ alkyl, —OH, —NH₂, —OR₂₁, halogen, cyano and oxo;

R₁₃, R₁₅, and R₁₆ are independently selected from the group consisting of hydrogen, C₁₋₄ alkyl, and C₃₋₈cycloakyl, wherein said alkyl or cycloalkyl is optionally substituted by one or more substituents selected from the group consisting of hydroxy, cyano and halo; and R₁₇ is selected from the group consisting of amino, halo, hydroxy, cyano, trifluoromethyl, trifluoromethoxy, C₁₋₄ alkyl, and C₁₋₄alkoxy.

In certain embodiments, compounds have structural Formula X:

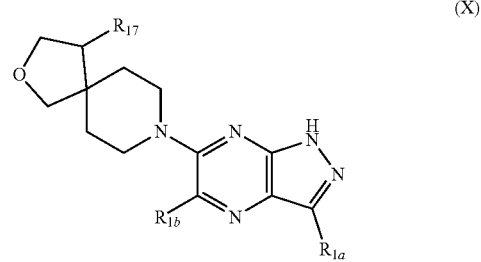

(X)

or a salt or tautomer thereof, wherein:

R₁ₐ is selected from the group consisting of halo, C₆₋₁₀aryl, C₃₋₈cycloalkyl, C₃₋₈cycloalkenyl, and a 5-9 membered heteroaryl group containing 1 to 4 heteroatoms or groups independently selected from the group consisting of N, C(O), O, and S;

said aryl or heteroaryl of R₁ₐ is optionally substituted with 1 to 5 R₁₂ groups independently selected from the group consisting of halo, hydroxy, amino, C₁₋₄ alkylamino, C₁₋₄ dialkylamino, cyano, C₁₋₄alkyl, C₁₋₄alkoxy, C₁₋₄hydroxyalkyl, C₁₋₄haloalkyl, C₁₋₄ aminoalkyl, C₃₋₈cycloalkyl, C₃₋₈cycloalkenyl, NR₁₅C(O)R₁₃, NR₁₅C(O)OR₁₃, NR₁₃C(O)NR₁₅R₁₆, NR₁₅S(O)R₁₃, NR₁₅S(O)₂R₁₃, C(O)NR₁₅R₁₆, S(O)NR₁₅R₁₆, S(O)₂NR₁₅R₁₆, C(O)R₁₃, C(O)OR₁₃, SR₁₃, S(O)R₁₃, and S(O)₂R₁₃;

R₁ᵦ is selected from the group consisting of halogen, cyano, C₁₋₆ alkyl, C₁₋₆haloalkyl, C₁₋₆hydroxyalkyl, C₁₋₆dihydroxyalkyl, —CF₂OH, —CHFOH, —NH—NHR₁₉, —NH—OR₁₉, —O—NR₁₉R₂₀, —NHR₁₉, —OR₁₉, —NHC(O)R₁₉, —NHC(O)NHR₁₉, —NHS(O)₂NHR₁₉, —NHS(O)₂R₁₉, —C(O)OR₁₉, —C(O)NR₁₉R₂₀, —C(O)NH(CH₂)ₙOH, —C(O)NH(CH₂)ₙR₂₁, —C(O)R₂₁, —NH₂, —OH, —CN, —S(O)₂NR₁₉R₂₀, C₃-C₈ cycloalkyl, aryl, heterocyclyl having 1-5 heteroatom ring vertices selected from the group consisting of N, O, S and P, heteroaryl having 1-5 heteroatom ring vertices selected from the group consisting of N, O, S and P; wherein the subscript n is an integer of from 0 to 6; and wherein aryl, heteroaryl, heterocyclyl and cycloalkyl are substituted with 0 to 3 members independently selected from the group consisting of C₁₋₄ alkyl, —OH, —NH₂, —OR₂₁, halogen, cyano and oxo;

R₁₃, R₁₅, and R₁₆ are independently selected from the group consisting of hydrogen, C₁₋₄ alkyl, and C₃₋₈cycloakyl, wherein said alkyl or cycloalkyl is optionally substituted by one or more substituents selected from the group consisting of hydroxy, cyano and halo; and
$R_{17}$ is selected from the group consisting of amino, halo, hydroxy, cyano, trifluoromethyl, trifluoromethoxy, $C_{1-4}$ alkyl, and $C_{1-4}$alkoxy.

In certain embodiments, compounds have structural Formula XI:

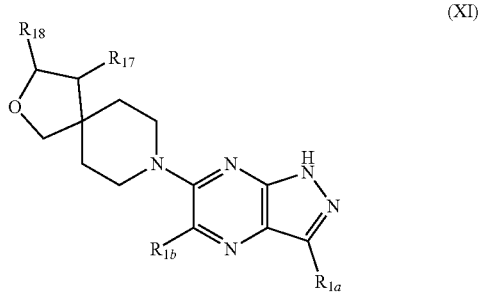

(XI)

or a salt or tautomer thereof, wherein:
$R_{1a}$ is selected from the group consisting of halo, $C_{6-10}$aryl, $C_{3-8}$cycloalkyl, $C_{3-8}$cycloalkenyl, and a 5-9 membered heteroaryl group containing 1 to 4 heteroatoms or groups independently selected from the group consisting of N, C(O), O, and S;
said aryl or heteroaryl of $R_{1a}$ is optionally substituted with 1 to 5 $R_{12}$ groups independently selected from the group consisting of halo, hydroxy, amino, $C_{1-4}$ alkylamino, $C_{1-4}$ dialkylamino, cyano, $C_{1-4}$alkyl, $C_{1-4}$alkoxy, $C_{1-4}$hydroxyalkyl, $C_{1-4}$haloalkyl, $C_{1-4}$ aminoalkyl, $C_{3-8}$cycloalkyl, $C_{3-8}$cycloalkenyl, $NR_{15}C(O)R_{13}$, $NR_{15}C(O)OR_{13}$, $NR_{13}C(O)NR_{15}R_{16}$, $NR_{15}S(O)R_{13}$, $NR_{15}S(O)_2R_{13}$, $C(O)NR_{15}R_{16}$, $S(O)NR_{15}R_{16}$, $S(O)_2NR_{15}R_{16}$, $C(O)R_{13}$, $C(O)OR_{13}$, $SR_{13}$, $S(O)R_{13}$, and $S(O)_2R_{13}$;
$R_{1b}$ is selected from the group consisting of halogen, cyano, $C_{1-6}$ alkyl, $C_{1-6}$ haloalkyl, $C_{1-6}$ hydroxyalkyl, $C_{1-6}$ dihydroxyalkyl, —$CF_2OH$, —CHFOH, —NH—$NHR_{19}$, —NH—$OR_{19}$, —O—$NR_{19}R_{20}$, —$NHR_{19}$, —$OR_{19}$, —NHC(O)$R_{19}$, —NHC(O)NH$R_{19}$, —NHS(O)$_2NHR_{19}$, —NHS(O)$_2R_{19}$, —C(O)O$R_{19}$, —C(O)N$R_{19}R_{20}$, —C(O)NH(CH$_2$)$_n$OH, —C(O)NH(CH$_2$)$_n$$R_{21}$, —C(O)$R_{21}$, —NH$_2$, —OH, —CN, —S(O)$_2$N$R_{19}R_{20}$, $C_3$-$C_8$ cycloalkyl, aryl, heterocyclyl having 1-5 heteroatom ring vertices selected from the group consisting of N, O, S and P, heteroaryl having 1-5 heteroatom ring vertices selected from the group consisting of N, O, S and P; wherein the subscript n is an integer of from 0 to 6; and wherein aryl, heteroaryl, heterocyclyl and cycloalkyl are substituted with 0 to 3 members independently selected from the group consisting of $C_{1-4}$ alkyl, —OH, —NH$_2$, —O$R_{21}$, halogen, cyano and oxo;
$R_{13}$, $R_{15}$, and $R_{16}$ are independently selected from the group consisting of hydrogen, $C_{1-4}$ alkyl, and $C_{3-8}$cycloalkyl, wherein said alkyl or cycloalkyl is optionally substituted by one or more substituents selected from the group consisting of hydroxy, cyano and halo;
$R_{17}$ is selected from the group consisting of amino, halo, hydroxy, cyano, trifluoromethyl, trifluoromethoxy, $C_{1-4}$ alkyl, and $C_{1-4}$alkoxy; and
$R_{18}$ is selected from the group consisting of halo, hydroxy, cyano, and $C_{1-4}$ alkyl.

In certain embodiments of any one of Formulae II-XI, $R_{1a}$, $R_{1b}$, $R_6$, $R_7$, $R_{17}$, and $R_{18}$ may have the meanings set forth in any one or more of the selected embodiments noted above.

In certain embodiments of any one of Formulae II-XI, $R_{1b}$ is selected from the group consisting of halogen, cyano, $C_{1-6}$ alkyl, $C_{1-6}$ haloalkyl, $C_{1-6}$ hydroxyalkyl, $C_{1-6}$dihydroxyalkyl, —$CF_2OH$, —CHFOH, $C_3$-$C_8$ cycloalkyl, 5- or 6-membered heterocyclyl having 1-3 heteroatom ring vertices selected from the group consisting of N, O and S, 5- or 6-membered heteroaryl having 1-4 heteroatom ring vertices selected from the group consisting of N, O, and S; wherein heteroaryl, heterocyclyl and cycloalkyl are substituted with 0 to 3 members independently selected from the group consisting of $C_{1-4}$ alkyl, —OH, —NH$_2$, —O$R_{21}$, halogen, cyano and oxo.

In certain embodiments of any one of Formulae II-XI, $R_{1b}$ is selected from the group consisting of halogen, cyano, $C_{1-6}$ alkyl, $C_{1-6}$ haloalkyl, $C_{1-6}$ hydroxyalkyl, $C_{1-6}$dihydroxyalkyl, —$CF_2OH$, —CHFOH and $C_3$-$C_8$ cycloalkyl. In certain embodiments, $R_{1b}$ is halogen, $C_{1-6}$ alkyl, $C_{1-6}$ haloalkyl, $C_{1-6}$ hydroxyalkyl, $C_{1-6}$ dihydroxyalkyl, —$CF_2OH$, or —CHFOH. In certain embodiments, $R_{1b}$ is halogen, $C_{1-6}$ alkyl, or $C_{1-6}$ haloalkyl. In certain embodiments, $R_{1b}$ is $C_{1-6}$ hydroxyalkyl, $C_{1-6}$dihydroxyalkyl, —$CF_2OH$, or —CHFOH. In certain embodiments, $R_{1b}$ is halogen or $C_{1-6}$ alkyl. In certain embodiments, $R_{1b}$ is halogen. In certain embodiments, $R_{1b}$ is $C_{1-6}$alkyl. In certain embodiments, $R_{1b}$ is $C_{1-6}$ hydroxyalkyl. In certain embodiments, $R_{1b}$ is chloro, methyl, CH$_2$F, CHF$_2$, or CH$_2$OH. In certain embodiments, $R_{1b}$ is chloro. In certain embodiments, $R_{1b}$ is methyl. In certain embodiments, $R_{1b}$ is CH$_2$OH.

In certain embodiments of any one of Formulae II-XI, $R_{1b}$ is 5- or 6-membered heterocyclyl having 1-3 heteroatom ring vertices selected from the group consisting of N, O and S, and 5- or 6-membered heteroaryl having 1-4 heteroatom ring vertices selected from the group consisting of N, O, and S; wherein heteroaryl and heterocyclyl are substituted with 0 to 2 members independently selected from the group consisting of $C_{1-4}$ alkyl, —OH, —NH$_2$, $C_{1-4}$ alkoxy, halogen, cyano and oxo.

In certain embodiments of Formula II or III, $R_6$ is amino. In certain embodiments, $R_6$ is $C_{1-4}$aminoalkyl. In certain embodiments, $R_6$ is aminomethyl. In certain embodiments, $R_6$ is methylamino.

In certain embodiments of Formula II or III, $R_7$ is hydroxy. In certain embodiments, $R_7$ is $C_{1-4}$ hydroxyalkyl. In certain embodiments, $R_7$ is hydroxymethyl. In certain embodiments, $R_7$ is selected from the group consisting of cyano and amido. In certain embodiments, $R_7$ is selected from the group consisting of cyano and C(O)NH$_2$. In certain embodiments, $R_7$ is $C_{1-4}$alkyl. In certain embodiments, $R_7$ is methyl.

In certain embodiments of any one of Formulae II-XI, each $R_{12}$ group is independently selected from the group consisting of halo, hydroxy, amino, methylamino, ethylamino, dimethylamino, cyano, $C_{1-4}$alkyl, $C_{1-4}$alkoxy, $C_{1-4}$hydroxyalkyl, $C_{1-4}$haloalkyl, and $C_{1-4}$aminoalkyl. In certain embodiments, each $R_{12}$ group is independently selected from the group consisting of halo, hydroxy, cyano, $C_{1-4}$alkyl, $C_{1-4}$alkoxy, and $C_{1-4}$hydroxyalkyl. In certain embodiments, each $R_{12}$ is independently halo, amino, methylamino, or ethylamino. In certain embodiments, each $R_{12}$ is independently halo, methylamino, or ethylamino.

In certain embodiments of any one of Formulae V-XI, $R_{17}$ is selected from the group consisting of amino, halo, hydroxy, and cyano. In certain embodiments, $R_{17}$ is selected from the group consisting of amino, hydroxy, and cyano. In certain embodiments, $R_{17}$ is selected from the group consisting of amino, halo, and hydroxy. In certain embodiments, $R_{17}$ is amino.

In certain embodiments any one of Formulae VI, VIII and XI, $R_{18}$ is selected from the group consisting of halo, hydroxy, cyano, and $C_{1-4}$ alkyl. In certain embodiments, $R_{18}$ is halo. In certain embodiments, $R_{18}$ is $C_{1-4}$alkyl. In certain embodiments, $R_{18}$ is methyl.

In certain embodiments of Formula VII, each $R_{18}$ is independently selected from the group consisting of halo, hydroxy, cyano, and $C_{1-4}$ alkyl. In certain embodiments, each $R_{18}$ is independently halo or $C_{1-4}$alkyl. In certain embodiments, each $R_{18}$ is methyl.

In certain embodiments, including any of the embodiments described above, further embodiments are those in which $R_{1a}$ is phenyl or pyridyl, each of which is substituted with 0 to 2 $R_{12}$.

In certain embodiments, including any of the embodiments described above, further embodiments are those in which $R_{1b}$ is selected from the group consisting of $C_{1-6}$ hydroxyalkyl, $C_{1-6}$ dihydroxyalkyl, —$CF_2OH$, and CHFOH. In still other selected embodiments, including any of the embodiments described above, further embodiments are those in which $R_{1b}$ is —$CH_2OH$.

In certain embodiments, including any of the embodiments described above, further embodiments are those in which $R_{1b}$ is methyl.

In certain embodiments, including any of the embodiments described above, further embodiments are those in which $R_{1b}$ is chloro.

Also provided are embodiments wherein any embodiment above may be combined with any one or more of these embodiments, provided the combination is not mutually exclusive.

As used herein, two embodiments are "mutually exclusive" when one is defined to be something which is different than the other. For example, an embodiment wherein two groups combine to form a cycloalkyl is mutually exclusive with an embodiment in which one group is ethyl the other group is hydrogen. Similarly, an embodiment wherein one group is $CH_2$ is mutually exclusive with an embodiment wherein the same group is NH.

Also provided is a compound selected from the Examples disclosed herein.

Methods of Use

The present invention also relates to a method of inhibiting at least one PTPN11 function comprising the step of contacting PTPN11 with a compound as described herein. The cell phenotype, cell proliferation, activity of PTPN11, change in biochemical output produced by active PTPN11, expression of PTPN11, or binding of PTPN11 with a natural binding partner may be monitored. Such methods may be modes of treatment of disease, biological assays, cellular assays, biochemical assays, or the like.

Also provided herein is a method of treatment of a PTPN11-mediated disease comprising the administration of a therapeutically effective amount of a compound as disclosed herein, or a salt or tautomer thereof, to a patient in need thereof.

In certain embodiments, the disease is Noonan Syndrome or Leopard Syndrome.

In certain embodiments, the disease is cancer.

In certain embodiments, the cancer is breast cancer, colon cancer, leukemia, or melanoma.

Also provided herein is a method of treatment of a PTP-mediated disease comprising the administration of a therapeutically effective amount of a compound as disclosed herein, or a salt or tautomer thereof, to a patient in need thereof.

In certain embodiments, the disease is Noonan Syndrome or Leopard Syndrome.

In certain embodiments, the disease is cancer.

In certain embodiments, the cancer is breast cancer, colon cancer, leukemia, or melanoma.

Also provided herein is a compound as disclosed herein for use as a medicament.

Also provided herein is a compound as disclosed herein for use as a medicament for the treatment of a PTPN11-mediated disease.

Also provided herein is a compound as disclosed herein for use as a medicament for the treatment of a PTP-mediated disease.

Also provided is the use of a compound as disclosed herein as a medicament.

Also provided is the use of a compound as disclosed herein as a medicament for the treatment of a PTPN11-mediated disease.

Also provided is a compound as disclosed herein for use in the manufacture of a medicament for the treatment of a PTPN11-mediated disease.

Also provided is the use of a compound as disclosed herein for the treatment of a PTPN11-mediated disease.

Also provided is the use of a compound as disclosed herein for the treatment of a PTP-mediated disease.

Also provided herein is a method of inhibition of PTPN11 comprising contacting PTPN11 with a compound as disclosed herein, or a salt or tautomer thereof.

Also provided herein is a method of inhibition of PTP comprising contacting PTP with a compound as disclosed herein, or a salt or tautomer thereof.

Also provided herein is a method for achieving an effect in a patient comprising the administration of a therapeutically effective amount of a compound as disclosed herein, or a salt or tautomer thereof, to a patient, wherein the effect is cognition enhancement.

In certain embodiments, the PTPN11-mediated disease is Noonan Syndrome or Leopard Syndrome.

In certain embodiments, the PTPN11-mediated disease is cancer.

In certain embodiments, the PTPN11-mediated disease is breast cancer, colon cancer, leukemia, or melanoma.

Also provided is a method of modulation of a PTPN11-mediated function in a subject comprising the administration of a therapeutically effective amount of a compound as disclosed herein.

Pharmaceutical Compositions

Also provided is a pharmaceutical composition comprising a compound as disclosed herein, together with a pharmaceutically acceptable carrier.

In certain embodiments, the pharmaceutical composition is formulated for oral administration.

In certain embodiments, the pharmaceutical composition is formulated for parenteral administration.

In certain embodiments, the pharmaceutical composition is formulated for intravenous administration.

In certain embodiments, the pharmaceutical composition is formulated for subcutaneous administration.

In certain embodiments, the oral pharmaceutical composition is a tablet or a capsule.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration selected. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

Administration and Combination Therapy

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, tautomer, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain compounds of the invention with anti-cancer (chemotherapeutic) drugs. Classes of anti-cancer drugs include, but are not limited to: alkylating agents, anti-metabolites, antimitotics, checkpoint inhibitors, plant alkaloids and terpenoids, topoisomerase inhibitors, cytotoxic antibiotics, aromatase inhibitors, angiogenesis inhibitors, anti-steroids and anti-androgens, mTOR inhibitors, tyrosine kinase inhibitors, and others.

For use in cancer and neoplastic diseases a PTPN11 (SHP2) inhibitor may be optimally used together with one or more of the following non-limiting examples of anti-cancer agents:

(1) alkylating agents, including but not limited to carmustine, chlorambucil (LEUKERAN), cisplatin (PLATIN), carboplatin (PARAPLATIN), oxaliplatin (ELOXATIN), streptozocin (ZANOSAR), busulfan (MYLERAN), dacarbazine, ifosfamide, lomustine (CCNU), melphalan (ALKERAN), procarbazine (MATULAN), temozolomide(TEMODAR), thiotepa, and cyclophosphamide (ENDOXAN);

(2) anti-metabolites, including but not limited to cladribine (LEUSTATIN), mercaptopurine (PURINETHOL), thioguanine, pentostatin (NIPENT), cytosine arabinoside (cytarabine, ARA-C), gemcitabine (GEMZAR), fluorouracil (5-FU, CARAC), capecitabine (XELODA), leucovorin (FUSILEV), methotrexate (RHEUMATREX), raltitrexed;

(3) antimitotics, which are often plant alkaloids and terpenoids, or derivatives thereof, including but not limited to taxanes such as docetaxel (TAXITERE) and paclitaxel (ABRAXANE, TAXOL); *vinca* alkaloids such as vincristine (ONCOVIN), vinblastine, vindesine, and vinorelbine (NAVELBINE);

(4) checkpoint inhibitors, such as anti-PD-1 or PD-L1 antibodies pembrolizumab (KEYTRUDA), nivolumab (OPDIVO), MEDI4736, and MPDL3280A; anti-CTLA-4 antibody ipilimumab (YERVOY); and those that target LAG3 (lymphocyte activation gene 3 protein), MR (killer cell immunoglobulin-like receptor), 4-1BB (tumour necrosis factor receptor superfamily member 9), TIM3 (T-cell immunoglobulin and mucin-domain containing-3) and OX40 (tumour necrosis factor receptor superfamily member 4);

(5) topoisomerase inhibitors, including but not limited to camptothecin (CTP), irinotecan (CAMPTOSAR), topotecan (HYCAMTIN), teniposide (VUMON), and etoposide (EPOSIN);
(6) cytotoxic antibiotics, including but not limited to actinomycin D (dactinomycin, COSMEGEN), bleomycin (BLENOXANE) doxorubicin (ADRIAMYCIN), daunorubicin (CERUBIDINE), epirubicin (ELLENCE), fludarabine (FLUDARA), idarubicin, mitomycin (MITOSOL), mitoxantrone (NOVANTRONE), plicamycin;
(7) aromatase inhibitors, including but not limited to aminoglutethimide, anastrozole (ARIMIDEX), letrozole (FEMARA), vorozole (RIVIZOR), exemestane (AROMASIN);
(8) angiogenesis inhibitors, including but not limited to genistein, sunitinib (SUTENT) and bevacizumab (AVASTIN);
(9) anti-steroids and anti-androgens such as aminoglutethimide (CYTADREN), bicalutamide (CASODEX), cyproterone, flutamide (EULEXIN), nilutamide (NILANDRON);
(10) tyrosine kinase inhibitors, including but not limited to imatinib (GLEEVEC), erlotinib (TARCEVA), lapatininb (TYKERB), sorafenib (NEXAVAR), and axitinib (INLYTA);
(11) mTOR inhibitors such as everolimus, temsirolimus (TORISEL), and sirolimus;
(12) monoclonal antibodies such as trastuzumab (HERCEPTIN) and rituximab (RITUXAN);
(13) other agents, such as amsacrine; *Bacillus* Calmette-Guérin (B-C-G) vaccine; buserelin (ETILAMIDE); chloroquine (ARALEN); clodronate, pamidronate, and other bisphosphonates; colchicine; demethoxyviridin; dichloroacetate; estramustine; filgrastim (NEUPOGEN); fludrocortisone (FLORINEF); goserelin (ZOLADEX); interferon; leucovorin; leuprolide (LUPRON); levamisole; lonidamine; mesna; metformin; mitotane (o,p'-DDD, LYSODREN); nocodazole; octreotide (SANDOSTATIN); perifosine; porfimer (particularly in combination with photo- and radiotherapy); suramin; tamoxifen; titanocene dichloride; tretinoin; anabolic steroids such as fluoxymesterone(HALOTESTIN); estrogens such as estradiol, diethylstilbestrol (DES), and dienestrol; progestins such as medroxyprogesterone acetate (MPA) and megestrol; and testosterone.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating PTPN11-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of PTPN11-mediated disorders.

In some embodiments, methods described herein are used to treat a disease condition comprising administering to a subject in need thereof a therapeutically effective amount of a compound of Formula I or pharmaceutically acceptable salt thereof, wherein the condition is cancer which has developed resistance to chemotherapeutic drugs and/or ionizing radiation.

In some embodiments, methods described herein are used to treat a disease condition comprising administering to a subject in need thereof a therapeutically effective amount of a compound of Formula I or pharmaceutically acceptable salt thereof, wherein the condition is cancer which has developed resistance to chemotherapeutic drugs and/or ionizing radiation.

The compounds, compositions, and methods disclosed herein are useful for the treatment of disease. In certain embodiments, the disease is one of dysregulated cellular proliferation, including cancer. The cancer may be hormone-dependent or hormone-resistant, such as in the case of breast cancers. In certain embodiments, the cancer is a solid tumor. In other embodiments, the cancer is a lymphoma or leukemia. In certain embodiments, the cancer is and a drug resistant phenotype of a cancer disclosed herein or known in the art. Tumor invasion, tumor growth, tumor metastasis, and angiogenesis may also be treated using the compositions and methods disclosed herein. Precancerous neoplasias are also treated using the compositions and methods disclosed herein.

Cancers to be treated by the methods disclosed herein include colon cancer, breast cancer, ovarian cancer, lung cancer and prostate cancer; cancers of the oral cavity and pharynx (lip, tongue, mouth, larynx, pharynx), esophagus, stomach, small intestine, large intestine, colon, rectum, liver and biliary passages; pancreas, bone, connective tissue, skin, cervix, uterus, corpus endometrium, testis, bladder, kidney and other urinary tissues, including renal cell carcinoma (RCC); cancers of the eye, brain, spinal cord, and other components of the central and peripheral nervous systems, as well as associated structures such as the meninges; and thyroid and other endocrine glands. The term "cancer" also encompasses cancers that do not necessarily form solid tumors, including Hodgkin's disease, non-Hodgkin's lymphomas, multiple myeloma and hematopoietic malignancies including leukemias (Chronic Lymphocytic Leukemia (CLL), Acute Lymphocytic Leukemia (ALL), Chronic Myelogenous Leukemia (CML), Acute Myelogenous Leukemia (AML),) and lymphomas including lymphocytic, granulocytic and monocytic. Additional types of cancers which may be treated using the compounds and methods of the invention include, but are not limited to, adenocarcinoma, angiosarcoma, astrocytoma, acoustic neuroma, anaplastic astrocytoma, basal cell carcinoma, blastoglioma, chondrosarcoma, choriocarcinoma, chordoma, craniopharyngioma, cutaneous melanoma, cystadenocarcinoma, endotheliosarcoma, embryonal carcinoma, ependymoma, Ewing's tumor, epithelial carcinoma, fibrosarcoma, gastric cancer, genitourinary tract cancers, glioblastoma multiforme, head and neck cancer, hemangioblastoma, hepatocellular carcinoma, hepatoma, Kaposi's sarcoma, large cell carcinoma, leiomyosarcoma, leukemias, liposarcoma, lymphatic system cancer, lymphomas, lymphangiosarcoma, lymphangioendotheliosarcoma, medullary thyroid carcinoma, medulloblastoma, meningioma mesothelioma, myelomas, myxosarcoma neuroblastoma, neurofibrosarcoma, oligodendroglioma, osteogenic sarcoma, epithelial ovarian cancer, papillary carcinoma, papillary adenocarcinomas, paraganglioma, parathyroid tumours, pheochromocytoma, pinealoma, plasmacytomas, retinoblastoma, rhabdomyosarcoma, sebaceous gland carcinoma, seminoma, skin cancers, melanoma, small cell lung carcinoma, non-small cell lung carcinoma, squamous cell carcinoma, sweat gland carcinoma, synovioma, thyroid cancer, uveal melanoma, and Wilm's tumor.

In certain embodiments, the compositions and methods disclosed herein are useful for preventing or reducing tumor invasion and tumor metastasis.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Methods of Preparation

Synthetic Intermediates

The following synthetic intermediates can be used to practice the present invention.

Intermediate 101 tert-Butyl methyl(4-methylpiperidin-4-yl)carbamate

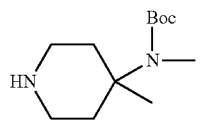 [SMILES: CN(C(=O)OC(C)(C)C)C1(C)CCNCC1]

tert-Butyl 1-benzyl-4-methylpiperidin-4-yl carbamate

To a solution of tert-butyl 4-methylpiperidin-4-yl carbamate (214 mg, 1.0 mmol) and $K_2CO_3$ (276 mg, 2.0 mmol) in DMF (10 mL) was added benzyl bromide (178 mg, 1.05 mmol). The reaction mixture was stirred at 50° C. for overnight. $H_2O$ was added and extracted with EtOAc. The organic layer was separated and washed with brine, dried over $Na_2SO_4$, filtered, and concentrated under reduced pressure. The residue was purified by silica gel column chromatography (Petroleum ether:EtOAc=2:1) to give tert-butyl 1-benzyl-4-methylpiperidin-4-yl carbamate as a colorless oil (267 mg, 88%).

MS (ES+) $C_{18}H_{28}N_2O_2$ requires: 304, found: 305 $[M+H]^+$.

1-Benzyl-N,4-dimethylpiperidin-4-amine

To a solution of the product from the previous step (267 mg, 0.88 mmol) in dry THF (10 mL) was added $LiAlH_4$ (100 mg, 2.64 mmol) slowly. The reaction mixture was heated to reflux for overnight. After cooled to rt, 2~3 drops of $H_2O$ was added and filtered. The solid was washed by EtOAc. The combined organics were concentrated to give the title compound as a colorless oil (180 mg, 94%).

MS (ES+) $C_{14}H_{22}N_2$ requires: 218, found: 219 $[M+H]^+$.

tert-Butyl 1-benzyl-4-methylpiperidin-4-yl(methyl)carbamate

To a solution of the product from the previous step (180 mg, 0.82 mmol) and $(Boc)_2O$ (268 mg, 1.23 mmol) in $CH_2Cl_2$ (10 mL) was added TEA (166 mg, 1.64 mmol). The reaction mixture was stirred at rt for 6 h. The solvent was removed and the residue was purified by silica gel column chromatography (Petroleum ether:EtOAc=2:1) to give the title compound as a colorless oil (190 mg, 73%).

MS (ES+) $C_{19}H_{30}N_2O_2$ requires: 318, found: 319 $[M+H]^+$.

tert-Butyl methyl(4-methylpiperidin-4-yl)carbamate

A solution of the product from the previous step (190 mg, 0.6 mmol) in MeOH (10 mL) was hydrogenated using 10% Pd/C (20 mg) as catalyst at 75° C. under atmospheric pressure for overnight. The catalyst was removed by filtration on CELITE™ and the solvent was evaporated under reduced pressure to give the title compound as a colorless oil (120 mg, 88%).

MS (ES+) $C_{12}H_{24}N_2O_2$ requires: 228, found: 229 $[M+H]^+$. $^1H$ NMR (500 MHz, $CDCl_3$) δ 2.84-2.8 (m, 5H), 2.23-2.18 (m, 2H), 1.71-1.67 (m, 4H), 1.46 (s, 9H), 1.28 (s, 3H).

Intermediate 102

(R)—N—((R)-1-(4-Methoxyphenyl)ethyl)-8-azaspiro[4.5]decan-1-amine

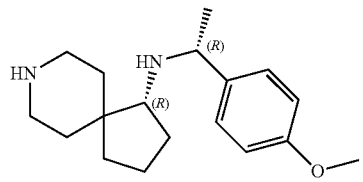

(R)-tert-butyl 1-((R)-1-(4-methoxyphenyl)ethylamino)-8-azaspiro 14.51decane-8-carboxylate To a solution of tert-butyl 1-oxo-8-azaspiro[4.5]decane-8-carboxylate (2.0 g, 7.9 mmol) in THF (15 mL) was added (R)-1-(4-methoxyphenyl)ethanamine (1.79 g, 11.9 mmol) and $Ti(OEt)_4$ (2 mL) at RT under $N_2$, then stirred at 85° C. for 18h. The mixture was concentrated in vacuo, then MeOH (10 mL) was added at RT, followed by the slow addition of $LiBH_4$ (0.33 g, 15.8 mmol). The mixture was stirred at RT for 2h. The reaction was then quenched with $H_2O$ (5 mL) and extracted with EtOAc (15 mL×3). The organic layer was separated and washed with brine, dried over $Na_2SO_4$, filtered, and concentrated under reduced pressure to give the title compound as a colorless oil (2.0 g, 66%).

MS (ES+) $C_{23}H_{36}N_2O_3$ requires: 388, found: 389 $[M+H]^+$.

(R)—N—((R)-1-(4-methoxyphenyl)ethyl)-8-azaspiro[4.5]decan-1-amine

A mixture of the product from the previous step (2.0 g, 5.2 mmol) in HCl/MeOH (3 M, 10 mL) was stirred at RT for 2 h. The mixture was then concentrated in vacuo. An aqueous solution of NaOH was then added to adjust the pH to 1012. The mixture was extracted with EtOAc (15 mL×3). The combined organic layers were separated and washed with brine, dried over $Na_2SO_4$, filtered, and concentrated under Intermediate 103

(S)—N—((R)-1-(4-Methoxyphenyl)ethyl)-2-oxa-8-azaspiro[4.5]decan-4-amine

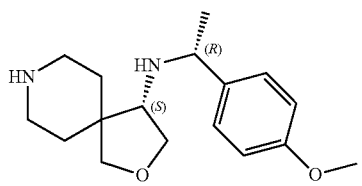

tert-Butyl 4-hydroxy-2-oxa-8-azaspiro[4.5]decane-8-carboxylate

To a solution of 2-oxa-8-azaspiro[4.5]decan-4-ol (1.0 g, 6.4 mmol) in CH$_2$Cl$_2$ (15 mL), was added di-tert-butyl dicarbonate (1.7 g, 7.6 mmol) at RT, then Et$_3$N (1.2 mL, 12.8 mmol) was added at RT. The reaction mixture was stirred at RT for 2h, quenched with H$_2$O (5 mL) and extracted with EtOAc (15 mL×3). The organic layer was separated and washed with brine, dried over Na$_2$SO$_4$, filtered, and concentrated under reduced pressure to give the title compound as a colorless oil (1.5 g, 90%), which was used directly without further purification.

MS (ES+) C$_{13}$H$_{23}$NO$_4$ requires: 257, found: 280 [M+Na]$^+$.

tert-Butyl 4-oxo-2-oxa-8-azaspiro[4.5]decane-8-carboxylate

To a solution of the product from the previous step (1.5 g, 5.8 mmol) in CH$_2$Cl$_2$ (15 mL) was added Dess-Martin reagent (3.7 g, 8.7 mmol) at rt. The resulting mixture was stirred at rt overnight. The reaction mixture was filtered, then quenched with H$_2$O (5 mL) and extracted with EtOAc (15 mL×3). The organic layer was separated and washed with brine, dried over Na$_2$SO$_4$, filtered, and concentrated under reduced pressure. The residue was purified by silica gel column chromatography (Petroleum ether:EtOAc=5:1) to give the title compound as a colorless oil (1.2 g, 86%).

MS (ES+) C$_{13}$H$_{21}$NO$_4$ requires: 255, found: 200 [M-55]$^+$.

(S)-tert-Butyl 4-((R)-1-(4-methoxyphenyl)ethyl-amino)-2-oxa-8-azaspiro[4.5]-decane-8-carboxylate To a solution of the product from the previous step in THF (15 mL) was added (R)-1-(4-methoxyphenyl)ethanamine (1.06 g, 7.06 mmol) and Ti(OEt)$_4$ (2 mL) at RT under N$_2$, then stirred at 85° C. for 18h. The residue was concentrated in vacuo, then MeOH (10 mL) was added. LiBH$_4$ (0.35 g, 14.8 mmol) was added at RT slowly, then the mixture was stirred at RT for 2 h. The reaction was quenched with the addition of H$_2$O (5 mL). The mixture was extracted with EtOAc (15 mL×3). The organic layer was separated and washed with brine, dried over Na$_2$SO$_4$, filtered, and concentrated under reduced pressure. The residue was purified by silica gel column chromatography (petroleum ether:EtOAc=4:1) to give the title compound as a colorless oil (1.3 g, 72%).

MS (ES+) C$_{22}$H$_{34}$N$_2$O$_4$ requires: 390, found: 391 [M+H]$^+$.

(S)—N—((R)-1-(4-Methoxyphenyl)ethyl)-2-oxa-8-azaspiro[4.5]decan-4-amine

A mixture of (S)-tert-butyl 4-((R)-1-(4-methoxyphenyl)ethylamino)-2-oxa-8-azaspiro[4.5]decane-8-carboxylate (1.3 g, 3.3 mmol) in HCl/MeOH (3 M, 10 mL) was stirred at RT for 2 h. Concentrated in vacuo and aqueous solution of NaOH was added to adjust the pH to 10-12, extracted with EtOAc (25 mL×3). The organic layer was separated and washed with brine, dried over Na$_2$SO$_4$, filtered, and concentrated under reduced pressure to give the crude (S)—N—((R)-1-(4-methoxyphenyl) ethyl)-2-oxa-8-azaspiro[4.5] decan-4-amine as a colorless oil (800 mg, yield: 89%) which was used directly without further purification.

MS (ES+) C$_{17}$H$_{26}$N$_2$O$_2$ requires: 290, found: 291 [M+H]$^+$.

Intermediate 104

Benzyl 4-(hydroxymethyl)piperidin-4-yl carbamate hydrochloride

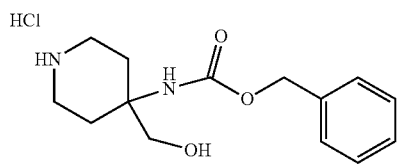

tert-Butyl 4-(benzyloxycarbonylamino)-4-(hydroxymethyl)piperidine-1-carboxylate

To a solution of tert-butyl 4-amino-4-(hydroxymethyl)piperidine-1-carboxylate (355 mg, 1.54 mmol) and benzyl chloroformate (288 mg, 1.69 mmol) in CH$_2$Cl$_2$ (20 mL) was added DIPEA (596 mg, 4.62 mmol) at 0° C. The reaction mixture was stirred at RT for overnight. The solvent was removed and the residue was purified by silica gel column chromatography (Petroleum ether:EtOAc=2:1) to give the titled compound as a white solid (450 mg, 80%).

MS (ES+) C$_{19}$H$_{28}$N$_2$O$_5$ requires: 364, found: 387.2 [M+Na]t $^1$H NMR (500 MHz, DMSO-d$_6$) δ 7.40-7.31 (m, 5H), 6.94 (s, 1H), 4.98 (s, 2H), 4.73 (t, J=6.0 Hz, 1H), 3.65-3.61 (m, 2H), 3.41 (d, J=6.0 Hz, 2H), 2.93-2.89 (m, 2H), 1.95-1.92 (m, 2H), 1.40-1.35 (m, 10H).

Benzyl 4-(hydroxymethyl)piperidin-4-yl carbamate hydrochloride

A solution of the product from the previous step (182 mg, 0.5 mmol) in HCl/MeOH (4M, 2 mL) was stirred at RT for 4 h. The solvent was removed under reduced pressure to give the title compound as a colorless oil (150 mg, 100%) which was used directly without further purification.

MS (ES+) C$_{14}$H$_{21}$ClN$_2$O$_3$ requires: 264, found: 265.3 [M+H]$^+$.

Intermediate 105

Benzyl 4-(fluoromethyl)piperidin-4-yl carbamate hydrochloride

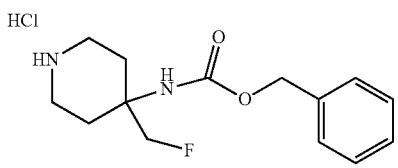 [SMILES: Cl ; O=C(NC1(CF)CCNCC1)OCc1ccccc1]

tert-Butyl 4-(benzyloxycarbonylamino)-4-(fluoromethyl)piperidine-1-carboxylate

To a solution of tert-butyl 4-(benzyloxycarbonylamino)-4-(hydroxymethyl)piperidine-1-carboxylate (255 mg, 0.7 mmol) in $CH_2Cl_2$ (10 mL) was added diethylaminosulfur trifluoride (147 mg, 0.9 mmol) at 0° C. The resulting mixture was stirred at 5° C. for 3h. The solvent was removed and the residue was purified by silica gel column chromatography (Petroleum ether:EtOAc=4:1) to give the title compound as a white solid (180 mg, 70%).

MS (ES+) $C_{19}H_{27}FN_2O_4$ requires: 366, found: 389.2 [M+Na]+.

Benzyl 4-(fluoromethyl)piperidin-4-yl carbamate hydrochloride

A solution of the product from the previous step (92 mg, 0.25 mmol) in HCl/MeOH (4M, 2 mL) was stirred at RT for 4h. The solvent was removed under reduced pressure to give the title compound as a colorless oil (75 mg, 100%) which was used directly without further purification.

MS (ES+) $C_{14}H_{20}ClFN_2O_2$ requires: 266, found: 267 [M+H]+.

Intermediate 106

(2-Chloropyridin-3-yl)(3,5-dichloropyrazin-2-yl)methanone

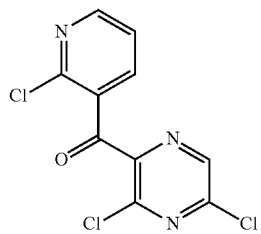 [SMILES: O=C(c1cccnc1Cl)c1ncc(Cl)nc1Cl]

(2-Chloropyridin-3-yl)(3,5-dichloropyrazin-2-yl)methanol

To a −78° C. solution of LDA (2.0M in hexane, 22.0 mmol) in dry THF (40 mL), under argon was slowly added 2,6-dichloropyrazine (1.65 g, 11.1 mmol) in THF (10 mL). After addition was completed, the resulting mixture was stirred at −78° C. for an additional 1 h, then 2-chloronicotinaldehyde (2.34 g, 16.6 mmol) in THF (10 mL) was added dropwise. The reaction mixture was stirred for another hour, then quenched with hydrochloric acid (3.6 mL)/EtOH (15 mL)/THF (18 mL) mixture, and warmed to RT. The reaction mixture was diluted with saturated aqueous $NaHCO_3$ and extracted with EtOAc. The organic layer was separated and washed with brine, dried over $Na_2SO_4$, filtered, and concentrated under reduced pressure. The residue was purified by silica gel column chromatography (Petroleum ether:EtOAc=4:1) to give the title compound as a yellow solid (880 mg, 27%).

MS (ES+) $C_{10}H_6Cl_3N_3O$ requires: 289, found: 290 [M+H]+.

(2-Chloropyridin-3-yl)(3,5-dichloropyrazin-2-yl)methanone

To a solution of the product from the previous step (0.88 g, 3.0 mmol) in $CH_2Cl_2$ (30 mL) was added solid $MnO_2$ (5.28 g, 60.0 mmol) in portions. The resulting mixture was stirred at RT overnight. The reaction mixture was filtered, and the filtrate was concentrated under reduced pressure. The residue was purified by silica gel column chromatography (Petroleum ether:EtOAc=4:1) to give the title compound as a yellow solid (380 mg, 43%).

MS (ES+) $C_{10}H_4Cl_3N_3O$ requires: 287, found: 288 [M+H]+.

Intermediate 107

(3-Chloropyridin-4-yl)(3,5-dichloropyrazin-2-yl)methanone

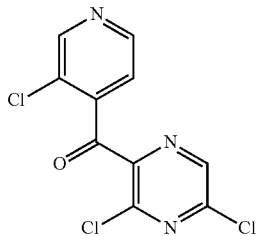 [SMILES: O=C(c1ccncc1Cl)c1ncc(Cl)nc1Cl]

(3-Chloropyridin-4-yl)(3,5-dichloropyrazin-2-yl)methanol

To a −78° C. solution of LDA (2.0M in hexane, 22.0 mmol) in dry THF (40 mL), under argon was slowly added 2,6-dichloropyrazine (1.65 g, 11.1 mmol) in THF (5 mL). After addition was completed, the resulting mixture was stirred at −78° C. for an additional 1 h, then 3-chloroisonicotinaldehyde (2.34 g, 16.6 mmol) in THF (5 mL) was added dropwise. The reaction mixture was stirred for another hour, then quenched with hydrochloric acid (3.6 mL)/EtOH (15 mL)/THF (18 mL) mixture, and warmed to rt. The reaction mixture was diluted with saturated aqueous $NaHCO_3$ and extracted with EtOAc. The organic layer was separated and washed with brine, dried over $Na_2SO_4$, filtered, and concentrated under reduced pressure. The residue was purified by silica gel column chromatography (Petroleum ether: EtOAc=2:1) to give the crude title compound as a yellow solid (900 mg) which was used in next step without further purification.

MS (ES+) $C_{10}H_6Cl_3N_3O$ requires: 289, found: 290 [M+H]+.

(3-Chloropyridin-4-yl)(3,5-dichloropyrazin-2-yl)methanone

To a solution of the crude product from the previous step (0.9 g, 3.1 mmol) in $CH_2Cl_2$ (30 mL) was added solid $MnO_2$ (5.46 g, 62.0 mmol) in portions. The resulting mixture was stirred at rt overnight. The reaction mixture was filtered, and the filtrate was concentrated under reduced pressure. The residue was purified by Prep-HPLC to give the title compound as a yellow solid (118 mg, 4% over 2 steps).
MS (ES+) $C_{10}H_4Cl_3N_3O$ requires: 287, found: 288 [M+H]+.

Intermediate 108

(3-Chloro-2-(4-methoxybenzylamino) pyridin-4-yl)(3,5-dichloropyrazin-2-yl)methanone

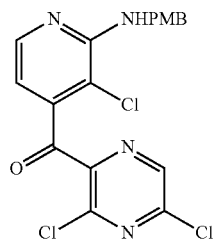

(2,3-Dichloropyridin-4-yl)methanol

A mixture of 2,3-dichloroisonicotinic acid (19.2 g, 10 mmol) in $BH_3$/THF (1 M, 300 mL) was stirred at 60° C. for 3 h. After cooling to RT, MeOH (100 mL) was slowly added, then the reaction mixture was concentrated and diluted with $H_2O$ (100 mL) and extracted with EtOAc (200 mL×3). The organic layer was separated and washed with brine, dried over $Na_2SO_4$, filtered and concentrated under reduced pressure to give the crude title compound (15.4 g, yield 87%) as a yellow solid which was used directly without further purification.
MS (ES+) $C_6H_5Cl_2NO$ requires: 177, found: 178 [M+H]+.

(3-Chloro-2-(4-methoxybenzylamino)pyridin-4-yl)methanol

A mixture of the product from the previous step (15.4 g, 86.5 mmol) in (4-methoxyphenyl)methanamine (15 mL) was stirred at 150° C. for 4 h. The mixture was purified by silica gel column chromatography (Petroleum ether:EtOAc=4:1-2:1) to give the title compound as a yellow solid (20 g, yield 83.3%).
MS (ES+) $C_{14}H_{15}ClN_2O_2$ requires: 278, found: 279 [M+H]+.

3-Chloro-2-(4-methoxybenzylamino)isonicotinaldehyde

To a solution of the product from the previous step (20 g, 71.9 mmol) in DCM (2 L) was added $MnO_2$ (125 g, 1.38 mol) in portionwise. The mixture was stirred at RT overnight. The reaction was filtered and the filtrate was purified by silica gel column chromatography (Petroleum ether:EtOAc=10:1~5:1) to give the title compound as a yellow solid (15 g, yield 75.7%).
MS (ES+) $C_{14}H_{13}ClN_2O_2$ requires: 276, found: 277 [M+H]+.

(3-Chloro-2-(4-methoxybenzylamino)pyridin-4-yl)(3,5-dichloropyrazin-2-yl)methanol To a −78° C. solution of LDA (2.0M in hexane, 22.0 mmol) in dry THF (40 mL), under argon was added 2,6-dichloropyrazine (1.648 g, 11.0 mmol) in THF (10 mL) slowly. After addition was complete, the resulting mixture was stirred at −78° C. for an additional 1 h, then the product from the previous step (4.55 g, 16.5 mmol) in THF (30 mL) was added dropwise. The reaction mixture was stirred for another hour, then quenched with HCl (1.8 mL)/EtOH (7.5 mL)/THF (9.0 mL) mixture, and warmed to RT. The reaction mixture was diluted with saturated aqueous $NaHCO_3$ solution and extracted with EtOAc. The organic layer was separated and washed with brine, dried over $Na_2SO_4$, filtered and concentrated under reduced pressure. The residue was purified by silica gel column chromatography (Petroleum ether:EtOAc=3:1) to give the title compound as a yellow solid (500 mg, yield 10.7%).
MS (ES+) $C_{18}H_{15}Cl_3N_4O_2$ requires: 424, found: 425 [M+H]+.

(3-Chloro-2-(4-methoxybenzylamino)pyridin-4-yl)(3,5-dichloropyrazin-2-yl)methanone To a solution of the product from the previous step (500 mg, 1.18 mmol) in $CH_2Cl_2$ (200 mL) was added solid $MnO_2$ (2.05 g, 23.58 mmol) portionwise. The result mixture was stirred at RT overnight. The reaction mixture was filtered off and the filtrate was concentrated to give the titled compound as a yellow solid (480 mg, yield 96%).
MS (ES+) $C_{18}H_{13}Cl_3N_4O_2$ requires: 422, found: 423 [M+H]+.

Intermediate 109

(3-Chloro-2-methoxypyridin-4-yl)(3,5-dichloropyrazin-2-yl)methanone

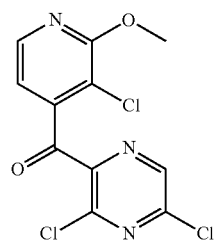 [SMILES: COc1nccc(C(=O)c2ncc(Cl)nc2Cl)c1Cl]

(3-Chloro-2-methoxypyridin-4-yl)methanol

Freshly prepared NaOMe in MeOH (from Na (4.12 g) in dry MeOH (45 mL)) was added dropwise to a solution of (2,3-dichloropyridin-4-yl)methanol (15 g, 87.2 mmol) in dry MeOH (20 mL). The reaction mixture was refluxed overnight, allowed to cool to RT and concentrated. The resulting mixture was quenched with $H_2O$ (300 mL) and extracted with EtOAc (3×300 mL). The combined organic layers were washed with brine (3×100 mL), dried over $Na_2SO_4$ and concentrated in vacuo to afford crude the title compound (13 g, yield 86.6%).

MS (ES+) $C_7H_8ClNO_2$ requires: 173, found: 174 $[M+H]^+$.

3-Chloro-2-methoxyisonicotinaldehyde

To a solution of the product from the previous step (13 g, 75.1 mmol) in DCM (2 L) was added $MnO_2$ (130 g, 1.5 mol) portionwise. The mixture was stirred at RT overnight. The reaction was filtered, and the filtrate was purified by silica gel column chromatography (Petroleum ether:EtOAc=10:1~8:1) to give the title compound as a white solid (10 g, yield 78.1%).

MS (ES+) $C_7H_6ClNO_2$ requires: 171, found: 172 $[M+H]^+$.

(3-Chloro-2-methoxypyridin-4-yl)(3,5-dichloropyrazin-2-yl)methanol

To a −78° C. solution of LDA (2.0M in hexane, 22.0 mmol) in dry THF (40 mL) under argon was added 2,6-dichloropyrazine (1.648 g, 11.0 mmol) in THF (10 mL) slowly. After addition was complete, the resulting mixture was stirred at −78° C. for an additional 1 h, then the product from the previous step (2.82 g, 16.5 mmol) in THF (10 mL) was added dropwise. The reaction mixture was stirred for another hour, then quenched with HCl (1.8 mL)/EtOH (7.5 mL)/THF (9.0 mL) mixture, and warmed to RT. The reaction mixture was diluted with sat. aq. $NaHCO_3$ solution and extracted with EtOAc. The organic layer was separated and washed with brine, dried over $Na_2SO_4$, filtered, and concentrated under reduced pressure. The residue was purified by silica gel column chromatography (Petroleum ether:EtOAc=3:1) to give the title compound as a white solid (500 mg, yield 14.2%).

MS (ES+) $C_{11}H_8Cl_3N_3O_2$ requires: 319, found: 320 $[M+H]^+$.

(3-Chloro-2-methoxypyridin-4-yl)(3,5-dichloropyrazin-2-yl)methanone

To a solution of the product from the previous step (500 mg, 1.56 mmol) in $CH_2Cl_2$ (200 mL) was added solid $MnO_2$ (2.71 g, 31.2 mmol) portionwise. The result mixture was stirred at RT overnight. The reaction mixture was filtered, and the filtrate was concentrated to give the title compound as a white solid (480 mg, yield 96%).

MS (ES+) $C_{11}H_6Cl_3N_3O_2$ requires: 317, found: 318 $[M+H]^+$.

Intermediate 110

(4-(4-Methoxybenzylamino)piperidin-4-yl)methanol dihydrochloride

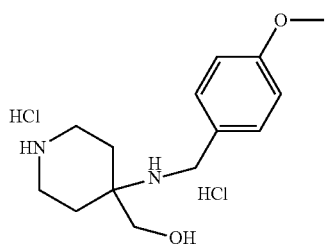 [SMILES: Cl ; COc1ccc(CNC2(CO)CCNCC2)cc1 ; Cl]

tert-Butyl 4-(hydroxymethyl)-4-(4-methoxybenzylamino)piperidine-1-carboxylate

To a solution of tert-butyl 4-amino-4-(hydroxymethyl)piperidine-1-carboxylate (100 mg, 0.43 mmol) and $K_2CO_3$ (119 mg, 0.86 mmol) in DMF (5 mL) was added 1-(chloromethyl)-4-methoxybenzene (81 mg, 0.52 mmol). The mixture was stirred at 50° C. overnight. $H_2O$ (20 mL) was added, and the resulting mixture was extracted with ETOAc (20 mL×3), dried and concentrated. The residue was purified by Prep-TLC eluting with PE:EtOAc=2:1 to give the title compound as a colorless oil (85 mg, 57%). MS (ES+) $C_{19}H_{30}N_2O_4$ requires: 350, found: 351 $[M+H]^+$.

(4-(4-Methoxybenzylamino)piperidin-4-yl)methanol dihydrochloride

A solution of the product from the previous step (85 mg, 0.24 mmol) in 4M HCl/MeOH (3 mL) was stirred at RT for 4 h. The solvent was removed to give the title compound as a white solid (78 mg, 100%), which was used directly without further purification. MS (ES+) $C_{14}H_{24}Cl_2N_2O_2$ requires: 250, found: 251.2 $[M+H]^+$.

Intermediate 111

(5-Chloro-2-(4-methoxybenzylamino)pyridin-4-yl)(3,5-dichloropyrazin-2-yl)methanone

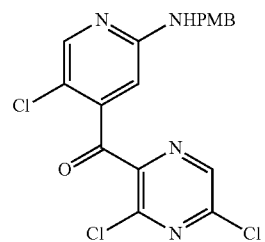

To a solution of (5-chloro-2-(4-methoxybenzylamino)pyridin-4-yl)(3,5-dichloropyrazin-2-yl)methanol (170 mg, 0.4 mmol) in DCM (20 mL) was added Dess-Martin reagent (255 mg, 0.6 mmol) at 0° C. The reaction mixture was stirred at RT for 4h, then poured into aq. $NaHCO_3$ and extracted with EtOAc (25 mL×3). The organic layers were dried over $Na_2SO_4$, filtered, and concentrated under reduced pressure. The residue was purified by Prep-TLC eluting with PE:EtOAc=3:1 to give the title compound as a yellow solid (137 mg, 80%).

MS (ES+) $C_{18}H_{13}Cl_3N_4O_2$ requires: 422, found: 423.1 $[M+H]^+$.

Intermediate 112

(3-Amino-2-chlorophenyl)(3,5-dichloropyrazin-2-yl)methanone

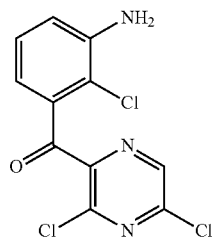

(2-Chloro-3-nitrophenyl)(3,5-dichloropyrazin-2-yl)methanol

To a solution of 2,6-dichloropyrazine (1.06 g, 7.2 mmol) in THF (10 mL) was added 2 M LDA in THF (7.2 mL, 14.4 mmol) at −78° C. under $N_2$ slowly. The mixture was then stirred at −78° C. for 1 h. A solution of 2-chloro-3-nitrobenzaldehyde (2.0 g, 10.8 mmol) in THF (5 mL) was added, and the mixture was stirred at −78° C. for another 1 h. The reaction was then quenched with aq. $NH_4Cl$ (10 mL), then the mixture was extracted with EtOAc (20 mL×3). The combined organic layers were washed with brine, dried over $Na_2SO_4$ and concentrated. The residue was purified by column chromatography on silica gel, eluting with PE:EtOAc=3:1 to give the title compound as a yellow solid (1.2 g, 50%).

MS (ES+) $C_{11}H_6Cl_3N_3O_3$ requires: 333, found: 334 $[M+H]^+$.

(2-Chloro-3-nitrophenyl)(3,5-dichloropyrazin-2-yl)methanone

To a solution of the product from the previous step in DCM (15 mL) was added $MnO_2$ (3.1 g, 36 mmol) at RT, then the mixture was stirred for 18 h, filtered and concentrated in vacuo. The residue was purified by column chromatography on silica gel, eluting with PE:EtOAc=4:1 to give the title compound as a white solid (0.6 g, 50%).

MS (ES+) $C_{11}H_4Cl_3N_3O_3$ requires: 331, found: 332 $[M+H]^+$.

(3-Amino-2-chlorophenyl)(3,5-dichloropyrazin-2-yl)methanone

To a solution of the product from the previous step (0.6 g, 1.8 mmol) in EtOH (10 mL) was added $SnCl_2 \cdot 2H_2O$ (0.8 g, 3.6 mmol) at RT. The mixture was then stirred at 90° C. for 18 h, then concentrated in vacuo. The residue was purified by column chromatography on silica gel, eluting with PE:EtOAc=1:1 to give the titled compound as a white solid (0.4 g, 74%).

MS (ES+) $C_{11}H_6Cl_3N_3O$ requires: 301, found: 302 $[M+H]^+$.

Intermediate 113

(3-Chloro-2-(methylamino)pyridin-4-yl)(3,5-dichloropyrazin-2-yl)methanone

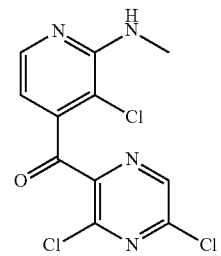 [SMILES: CNc1nccc(C(=O)c2ncc(Cl)nc2Cl)c1Cl]

(3-Chloro-2-(methylamino)pyridin-4-yl)methanol

To a solution of (2,3-dichloropyridin-4-yl)methanol (15.4 g, 87 mmol) in $CH_3NH_2$ (7 M in $H_2O$, 200 mL) was added MeOH (20 mL). The reaction mixture was stirred at 120° C. for 24 h, allowed to cool to RT and concentrated. The mixture was poured into $H_2O$ (100 mL) and extracted with EtOAc (3×300 mL). The combined organic layers were washed with brine (3×100 mL), dried over $Na_2SO_4$ and concentrated in vacuo to afford the titled compound crude (13 g, yield 86.6%).

MS (ES+) $C_7H_9ClN_2O$ requires: 172, found: 173 $[M+H]^+$.

3-Chloro-2-(methylamino)isonicotinaldehyde

To a solution of the product from the previous step (13 g, 75.5 mmol) in DCM (2 L) was added $MnO_2$ (131 g, 1.5 mol) portionwise. The mixture was stirred at RT overnight. The reaction was filtered, and the filtrate was purified by silica gel column chromatography (Petroleum ether:EtOAc=10:1~4:1) to give the title compound as a yellow solid (11 g, yield 84.6%).

MS (ES+) $C_7H_7ClN_2O$ requires: 170, found: 171 $[M+H]^+$.

(3-Chloro-2-(methylamino)pyridin-4-yl)(3,5-dichloropyrazin-2-yl)methanol

To a −78° C. solution of LDA (2.0M in hexane, 22.0 mmol) in dry THF (40 mL) under argon was added 2,6-dichloropyrazine (1.648 g, 11.0 mmol) in THF (10 mL) slowly. After addition was complete, the resulting mixture was stirred at −78° C. for an additional 1 h, then the product from the previous step (2.8 g, 16.5 mmol) in THF (10 mL) was added dropwise. The reaction mixture was stirred for another hour, then quenched with HCl (1.8 mL)/EtOH (7.5 mL)/THF (9.0 mL) mixture, and warmed to RT. The reaction mixture was diluted with sat. aq. $NaHCO_3$ solution and extracted with EtOAc. The organic layer was separated and washed with brine, dried over $Na_2SO_4$, filtered and concentrated under reduced pressure. The residue was purified by silica gel column chromatography (Petroleum ether:EtOAc=3:1) to give the title compound as a yellow solid (500 mg, yield 14.2%).

S (ES+) $C_{11}H_9Cl_3N_4O$ requires: 318, found: 319 $[M+H]^+$.

(3-Chloro-2-(methylamino)pyridin-4-yl)(3,5-dichloropyrazin-2-yl)methanone

To a solution of the product from the previous step (500 mg, 1.56 mmol) in CH$_2$Cl$_2$ (200 mL) was added solid MnO$_2$ (2.71 g, 31.2 mmol) portionwise. The resulting mixture was stirred at RT overnight. The reaction mixture was filtered, and the filtrate was concentrated to give the titled compound as a yellow solid (480 mg, yield 96%).

MS (ES+) C$_{11}$H$_{17}$Cl$_3$N$_4$O requires: 316, found: 317 [M+H]$^+$.

Intermediate 114

(R)-2-methyl-N-(1-(4-methylpiperidin-4-yl)ethyl)propane-2-sulfinamide

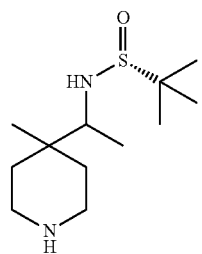 [SMILES: CC(N[S@](=O)C(C)(C)C)C1(C)CCNCC1]

tert-Butyl 4-(methoxy(methyl)carbamoyl)-4-methylpiperidine-1-carboxylate

To a solution of 1-(tert-butyloxycarbonyl)-4-methylpiperidine-4-carboxylic acid (15 g, 61.7 mmol), N,O-dimethylhydroxylamine hydrochloride (12 g, 123.4 mmol) and HATU (30.8 g, 80.2 mmol) in DMF (100 mL) was added TEA (25 g). The mixture was stirred at RT overnight. The mixture was diluted with EtOAc (700 mL) and washed with aq. NH$_4$Cl (200 mL×5). The organic phase was dried over Na$_2$SO$_4$ and concentrated to obtain the title compound as a brown oil (15 g, 90%).

MS (ES+) C$_{14}$H$_{26}$N$_2$O$_4$ requires: 286, found: 287 [M+H]$^+$.

tert-Butyl 4-acetyl-4-methylpiperidine-1-carboxylate

To a solution of the product from the previous step (5 g, crude) in THF (50 mL) was added MeMgCl (2M in THF, 26 mL, 52 mmol) at 0° C. The mixture was stirred at RT overnight. The mixture was poured into cold aq. NH$_4$Cl slowly then extracted with EtOAc (100 mL×3). The organic phase was washed with brine (100 mL), dried with Na$_2$SO$_4$, and concentrated to obtained the title compound as a brown oil (4 g, 85%).

MS (ES+) C$_{13}$H$_{23}$NO$_3$ requires 241, found: 242 [M+H]$^+$.

(R,E)-tert-Butyl 4-(1-(tert-butylsulfinylimino)ethyl)-4-methylpiperidine-1-carboxylate To a solution of the product from the previous step (2.0 g, 8.3 mmol) in dry THF (20 mL) was added (R)-2-methylpropane-2-sulfinamide (2.0 g, 16.6 mmol) and Ti(OEt)$_4$ (6 mL). The mixture was stirred at 85° C. overnight. The mixture was concentrated and use directly for the next step.

MS (ES+) C$_{17}$H$_{32}$N$_2$O$_3$S requires: 344, found: 345 [M+H]$^+$.

tert-Butyl 4-(1-((R)-1,1-dimethylethylsulfinamido)ethyl)-4-methylpiperidine-1-carboxylate and diastereomer To a mixture of the product from the previous step (2 g, crude) in MeOH (10 mL) was added NaBH$_4$ (631 mg, 16.6 mmol) at 0° C. The resulting mixture was stirred at RT for 4 hours. The mixture was quenched with water (10 mL), then concentrated under vacuum. EtOAc (50 mL) was added and filtered through a short CELITE® column. The aqueous phase was extracted with EtOAc (50 mL×3), then the organic phases were combined and washed with brine (50 mL), dried with MgSO$_4$, concentrated and purified by Pre-HPLC to obtain the title compound as a white solid (isomer 1:500 mg, isomer 2:240 mg).

MS (ES+) C$_{17}$H$_{34}$N$_2$O$_3$S requires: 346, found: 347 [M+H]$^+$.

(R)-2-methyl-N-(1-(4-methylpiperidin-4-yl)ethyl)propane-2-sulfinamide

To a solution of tert-butyl 4-(1-((R)-1,1-dimethylethylsulfinamido)ethyl)-4-methylpiperidine-1-carboxylate (isomer 1, 200 mg) in DCM (10 mL) was added TFA (2 mL) slowly at 0° C. and stirred at this temperature for 30 min, concentrated and used directly for the next step.

MS (ES+) C$_{12}$H$_{26}$N$_2$OS requires: 246, found: 247 [M+H]$^+$.

The same method was used to prepare the other diastereomer.

Intermediate 115

(3,5-Dichloropyrazin-2-yl)(2-(4-methoxybenzylamino)-3-methylpyridin-4-yl)methanone

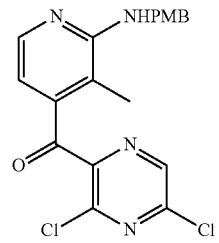

2-Fluoro-4-iodo-3-methylpyridine

To a solution of LDA (68 mL, 135 mmol) at −78° C. was added a solution of 2-fluoro-3-iodopyridine (30 g, 135 mmol) in THF (100 mL), and the mixture is stirred for 1 hour at −78° C. under nitrogen. MeI (25 mL, 405 mmol) was then added, and the mixture was stirred for 30 min at −78° C. The mixture was quenched with sat. aq. NaHCO$_3$ solution at −78° C. and then extracted with ether. The combined ether extracts were dried with MgSO$_4$ and concentrated in vacuo. The residue was purified by silica gel column chromatography (Petroleum ether:EtOAc=4:1) to give the title compound as a brown solid (22 g, 69%).

MS (ES+) C$_6$H$_5$FIN requires: 237, found: 238 [M+H]$^+$.

Methyl 2-fluoro-3-methylisonicotinate

A mixture of the product from the previous step (22 g, 93 mmol), Pd(OAc)$_2$ (2.2 g, 9.8 mmol), 1,1'-bisdiphenylphosphino ferrocene (5.1 g, 9.2 mmol), and NaHCO$_3$ (46.7 g, 556 mmol) in MeOH (1 L) was stirred overnight in a CO atmosphere at 80° C. The mixture was cooled to room temperature, then water and sat. aq. NaHCO$_3$ solution were added. The mixture was then extracted with EtOAc. The organic layers was washed with saturated brine, and then dried over anhydrous sodium sulfate. The mixture was filtered and concentrated under reduced pressure, and the obtained residue was purified by silica gel column chromatography (Petroleum ether:EtOAc=4:1) to give the title compound as a colorless oil (12 g, 77%).

MS (ES+) C$_8$H$_8$FNO$_2$ requires: 169, found: 170 [M+H]$^+$.

(2-Fluoro-3-methylpyridin-4-yl)methanol

To a solution of the product from the previous step (12 g, 71 mmol) in MeOH (100 mL) was added NaBH$_4$ (11 g, 290 mmol) portionwise. The resulting mixture was stirred at RT for 0.5 h, concentrated in vacuo. The residue was purified by silica gel column chromatography (Petroleum ether:EtOAc=2:1) to give the title compound as a brown solid (9 g, 90%).

MS (ES+) C$_7$H$_8$FNO requires: 141, found: 142 [M+H]$^+$.

(2-(4-Methoxybenzylamino)-3-methylpyridin-4-yl)methanol

A solution of the product from the previous step (9.7 g, 69 mmol), methoxybenzylamine (14.1 g, 103 mmol) and K$_2$CO$_3$ (14.1 g, 103 mmol) in DMSO (100 mL) was sealed and stirred at 150° C. for 1 hour. The reaction mixture was cooled to room temperature, then poured into cold water (500 mL) and extracted with EtOAc (500 mL×2). The combined EtOAc solution was washed with brine, dried over Na$_2$SO$_4$ and concentrated. The residue was purified by silica gel column chromatography (DCM:MeOH=100:3) to give the title compound as a brown solid (8 g, 45%).

MS (ES+) C$_{15}$H$_{18}$N$_2$O$_2$ requires: 258, found: 259 [M+H]$^+$.

2-(4-Methoxybenzylamino)-3-methylisonicotinaldehyde

To a solution of the product from the previous step (8 g, 31 mmol) in CH$_2$Cl$_2$ (1.5 L) was added MnO$_2$ (54 g, 620 mmol). The mixture was stirred at RT overnight, then filtered. The filtrate was concentrated under reduced pressure, and the obtained residue was purified by silica gel column chromatography (Petroleum ether:EtOAc=4:1) to give the title compound as a brown solid (7.2 g, 91%).

MS (ES+) C$_{15}$H$_{16}$N$_2$O$_2$ requires: 256, found: 257 [M+H]$^+$.

(3,5-Dichloropyrazin-2-yl)(2-(4-methoxybenzylamino)-3-methyl pyridin-4-yl)-methanol To a −78° C. solution of LDA (26 mL, 52 mmol) in dry THF (100 mL) under Ar was added 2,6-dichloropyrazine (3.9 g, 26 mmol) in 20 mL THF dropwise. The resulting solution was stirred at −78° C. for 1 h, then the product from the previous step (6.7 g, 26 mmol) in THF (20 mL) was added to the mixture dropwise at −78° C. The resulting solution was stirred at −78° C. for 1 h, then quenched with HCl (1.8 mL)/EtOH (7.5 mL)/THF (9.0 mL) mixture and warmed to rt. The reaction mixture was diluted with sat. aq. NaHCO$_3$ solution and extracted with EtOAc. The combined organic layers were separated and washed with brine, dried over Na$_2$SO$_4$, filtered, and concentrated under reduced pressure. The residue was purified by silica gel column chromatography (Petroleum ether:EtOAc=4:1) to give the title compound as a yellow solid (1.1 g, 11%).

MS (ES+) C$_{19}$H$_{18}$Cl$_2$N$_4$O$_2$ requires: 404, found: 405 [M+H]$^+$.

(3,5-Dichloropyrazin-2-yl)(2-(4-methoxybenzylamino)-3-methyl pyridin-4-yl)-methanone To a solution of the product from the previous step (1.1 g, 2.7 mmol) in CH$_2$Cl$_2$ (200 mL) was added MnO$_2$ (4.7 g, 54 mmol). The mixture was stirred at RT overnight, filtered, and concentrated under reduced pressure The obtained residue was purified by silica gel column chromatography (Petroleum ether:EtOAc=2:1) to give the title compound as a brown solid (600 mg, 55%).

MS (ES+) C$_{19}$H$_{16}$Cl$_2$N$_4$O$_2$ requires: 402, found: 403 [M+H]$^+$.

Intermediate 116

(R)—N-((1R,3S)-3-(tert-butyldimethylsilyloxy)-8-azaspiro[4.5]decan-1-yl)-2-methylpropane-2-sulfinamide

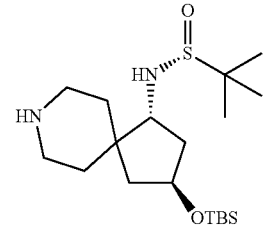 [SMILES: CC(C)(C)[S@@](=O)N[C@@H]1C[C@@H](O[Si](C)(C)C(C)(C)C)CC12CCNCC2]

tert-Butyl 2-oxo-6-oxaspiro[bicyclo[3.1.0]hexane-3,4'-piperidine]-1'-carboxylate A stirred solution of tert-butyl-1-oxo-8-azaspiro[4.5]dec-2-ene-8-carboxylate (500 mg; 1.99 mmoles) in MeOH (10 mL) was added H$_2$O$_2$ (13.93 mmol, 1.58 mL) followed by NaOH (656 μmol; 131 μL) at 0° C. After 45 min, the reaction was quenched by addition of one drop AcOH. The reaction mixture was poured into brine and extracted with EtOAc (3×25 mL). The combined organic layers were washed with NaHSO$_3$, dried and concentrated to obtain the title compound (440 mg, yield 82.7%) as a light brown oil which was used directly in the next step.

MS (ES+): C$_{14}$H$_{21}$NO$_4$ requires: 267.1, found: 290.0 [M+Na]$^+$, $^1$H NMR (500 MHz, CDCl$_3$) δ 4.08-3.95 (m, 1H), 3.92 (t, J=2.0 Hz, 1H), 3.88-3.73 (m, 1H), 3.48 (d, J=2.2 Hz, 1H), 2.92 (d, J=11.5 Hz, 2H), 2.44 (d, J=14.6 Hz, 1H), 1.87 (d, J=14.6 Hz, 1H), 1.78 (ddd, J=13.4, 11.4, 4.3 Hz, 1H), 1.70-1.62 (m, 1H), 1.45 (s, 9H), 1.32-1.18 (m, 2H).

tert-Butyl 3-hydroxy-1-oxo-8-azaspiro[4.5]decane-8-carboxylate

A solution of the product from the previous step (979 mg, 3.7 mmol) in acetone (25 mL) was treated with NaI (2.0 g, 13.5 mmol), NaOAc (1.36 mmol, 111 mg) and AcOH (13.55 mmol, 776 µL) at 25° C. for 30 min. The iodine formed from the reaction was reduced by addition of a saturated aqueous $Na_2S_2O_3$ solution (25 mL), and the acetone was removed by evaporation. The remaining aqueous mixture was diluted with EtOAc (75 mL) and washed with water (2×25 mL), sat. aq. $Na_2CO_3$ solution (3×25 mL), and brine (20 mL). The organic layer was dried ($MgSO_4$) and concentrated. The residue was purified on silica gel eluting with EtOAc-DCM 10-50% to obtain the title compound (819 mg, 83% yield) as a white solid.

MS (ES+): $C_{14}H_{23}NO_4$ requires: 269.2, found: 292.1 [M+Na]+; $^1$H NMR (500 MHz, $CDCl_3$) δ 4.67-4.56 (m, 1H), 3.99-3.75 (m, 2H), 3.10-2.90 (m, 2H), 2.65 (dd, J=18.4, 5.9 Hz, 1H), 2.46-2.33 (m, 1H), 2.19-2.04 (m, 2H), 1.97 (s, 1H), 1.85-1.76 (m, 1H), 1.70-1.62 (m, 2H), 1.45 (s, 9H).

tert-Butyl 3-(tert-butyldimethylsilyloxy)-1-oxo-8-azaspiro[4.5]decane-8-carboxylate A mixture of the product from the previous step (819 mg, 3.04 mmol), imidazole (4.56 mmol, 320.12 mg) and TBDMSCl (3.80 mmol, 590.61 mg) in DMF (5 mL) was stirred 16 h at room temperature. The reaction mixture was poured into a separation funnel containing sat. aq $NH_4Cl$:$H_2O$ (1:1, 50 mL) and extracted with $Et_2O$ (5×20 mL). The combined organic phases were dried over $MgSO_4$ and filtered, and the volatiles were removed under reduced pressure. The resulting residue was purified by silica chromatography (0-30% EtOAc/heptane eluent) to give the title compound (965 mg, 82.7% yield) as a colorless oil.

MS (ES+): $C_{20}H_{37}NO_4Si$ requires: 383.2, found: 406.2 [M+Na]+, $^1$H NMR (500 MHz, $CDCl_3$) δ 4.47-4.42 (m, 1H), 3.92-3.74 (m, 2H), 3.04-2.84 (m, 2H), 2.49 (dd, J=18.2, 5.7 Hz, 1H), 2.29 (d, J=18.1 Hz, 1H), 2.07-1.93 (m, 2H), 1.75-1.67 (m, 1H), 1.64-1.56 (m, 2H), 1.40 (s, 9H), 1.24-1.21 (m, 1H), 0.81 (s, 9H), 0.01 (s, 3H), -0.00 (s, 3H).

(R,E)-tert-butyl 3-(tert-butyldimethylsilyloxy)-1-((R)-tert-butylsulfinylimino)-8-azaspiro[4.5]decane-8-carboxylate and (S,E)-tert-butyl 3-(tert-butyldimethylsilyloxy)-1-((R)-tert-butylsulfinylimino)-8-azaspiro[4.5]decane-8-carboxylate A solution of the product from the previous step (0.21 g, 547 µmol), Ti(OEt)$_4$ (2.19 mmol, 462 µL) and (R)-2-methylpropane-2-sulfinamide (1.09 mmol, 132.7 mg) in THF (3 mL) was heated at 65° C. for 16 hours. The mixture was cooled to RT, quenched with sat. $NaHCO_3$ solution, and extracted with EtOAc (15 mL×4). The combined organic layers were washed with brine (20 mL), dried ($Na_2SO_4$), filtered and concentrated, and the residue was purified on silica gel eluting with EtOAc-PE 0-45% to obtain first the (R,E)-isomer ($R_f$=0.75, 74 mg, 28% yield) as a white solid:

MS (ES+): $C_{24}H_{46}N_2O_4SSi$ requires: 486.3, found: 509.3 [M+Na]+, $^1$H NMR (500 MHz, $CDCl_3$) δ 4.42-4.34 (m, 1H), 4.05-3.83 (m, 2H), 3.16 (dd, J=19.0, 3.3 Hz, 1H), 3.04-2.73 (m, 3H), 1.88-1.77 (m, 2H), 1.75-1.63 (m, 3H), 1.40 (s, J=3.3 Hz, 9H), 1.31-1.25 (m, 1H), 1.19 (s, 9H), 0.80 (s, 9H), 0.00 (d, J=3.0 Hz, 6H).

followed by the (S,E)-isomer ($R_f$=0.35, 75 mg, 28% yield) as a colorless oil:

MS (ES+): $C_{24}H_{46}N_2O_4SSi$ requires: 486.3, found: 509.3 [M+Na]+, $^1$H NMR (500 MHz, $CDCl_3$) δ 4.47-4.38 (m, 1H), 4.01-3.81 (m, 2H), 3.07 (dd, J=18.8, 5.6 Hz, 1H), 2.96-2.78 (m, 3H), 1.91 (d, J=13.4 Hz, 1H), 1.77 (dd, J=13.5, 5.0 Hz, 2H), 1.73-1.65 (m, 2H), 1.41 (s, 9H), 1.35-1.30 (m, 1H), 1.19 (s, 9H), 0.80 (s, 9H), -0.00 (s, 6H).

(1R,3S)-tert-butyl 3-(tert-butyldimethylsilyloxy)-1-((R)-1,1-dimethyl ethylsulfinamido)-8-azaspiro[4.5]decane-8-carboxylate To a solution of the product from the previous step (0.072 g, 148 µmol) in THF (5 mL) was added MeOH (0.5 mL) at -78° C., followed by LiBH$_4$ (444 µmol, 222 µL). The resulting mixture was stirred for 4 h at -78° C. Sat. $NH_4Cl$ solution was then added slowly to quench the excess of borohydride, followed by addition of EtOAc (25 mL). The resulting mixture was vigorously stirred for 15 min and then filtered through a pad of CELITE®. The volatiles were removed under reduced pressure, and the resulting residue was purified by silica chromatography (0 to 50% EtOAc/heptane) to give the title compound (56 mg, 77% yield) as a colorless oil.

MS (ES+): $C_{24}H_{48}N_2O_4SSi$ requires: 488.3, found: 489.3 [M+H]$^+$; $^1$H NMR (500 MHz, $CDCl_3$) δ 4.26 (s, 1H), 4.04-3.78 (m, 2H), 3.27 (s, 1H), 2.95-2.75 (m, 2H), 2.29 (s, 1H), 1.891.51 (m, 7H), 1.41 (s, 9H), 1.26-1.20 (m, 1H), 1.16 (s, 9H), 0.83 (s, 9H), -0.00 (s, 6H).

(R)—N-((1R,3S)-3-(tert-butyldimethylsilyloxy)-8-azaspiro[4.5]decan-1-yl)-2-methylpropane-2-sulfinamide To the product from the previous step (50 mg, 102 µmol) in DCM (5 mL) was added TFA (0.5 mL). The mixture was stirred at RT for 2 hours, then concentrated to obtain the title compound (40 mg, 100% yield) as a pale oil which was used without further purification.

MS(ES+): $C_{19}H_{40}N_2O_2SSi$ requires: 388.3, found: 389.3 [M+H]$^+$.

Intermediate 117

4-Aminopiperidine-4-carboxamide dihydrochloride

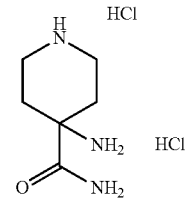

tert-butyl 4-amino-4-carbamoylpiperidine-1-carboxylate

To a solution of tert-butyl 4-amino-4-cyanopiperidine-1-carboxylate (50 mg, 0.22 mmol) and $K_2CO_3$ (61 mg, 0.44 mmol) in DMSO (1 mL) was added $H_2O_2$ (30% in water, 25 mg, 0.44 mmol) slowly. The resulting mixture was stirred at RT for 72h. The reaction mixture was quenched with aqueous $Na_2S_2O_3$ (15 mL), extracted with $CHCl_3$:i-PrOH (4:1, 30 mL×3), washed with brine, dried over $Na_2SO_4$ and concentrated under reduced pressure to give the title compound as a colorless syrup solid (60 mg, crude).

MS (ES+) $C_{11}H_{21}N_3O_3$ requires: 243, found 266 [M+Na]+.

4-Aminopiperidine-4-carboxamide dihydrochloride

To a solution of tert-butyl 4-amino-4-carbamoylpiperidine-1-carboxylate (60 mg, 0.25 mmol) in MeOH (0.5 mL) was added HCl/dioxane (4 M, 3 mL, 12 mmol). The resulting mixture was stirred at RT for 2h. The solid precipitated was filtered to give the title compound as a white solid (60 mg).

MS (ES+) $C_6H_{13}N_3O$ requires: 143, found: 144 $[M+H]^+$.

Intermediate 118

(3,5-Dichloropyrazin-2-yl)(2-(4-methoxybenzylamino)-5-methyl pyridin-4-yl)methanone

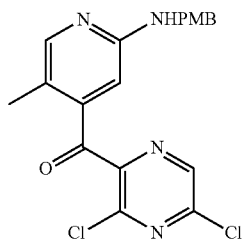

Methyl 2-fluoro-5-methylisonicotinate

A mixture of 2-fluoro-4-iodo-5-methyl-pyridine (3.4 g, 14 mmol), Pd(OAc)$_2$ (314 mg, 1.4 mmol), 1,1'-bisdiphenylphosphino ferrocene (776 mg, 1.4 mmol), TEA (7 g, 70 mmol) in MeOH (200 mL) was stirred overnight in a CO atmosphere at 80° C. The mixture was cooled to RT, then concentrated and purified by silica gel column chromatography (Petroleum ether:EtOAc=4:1) to give the title compound as a white solid (1.5 g, 75%).

MS (ES+) $C_8H_8FNO_2$ requires: 169, found: 170 $[M+H]^+$.

(2-Fluoro-5-methylpyridin-4-yl)methanol

To a solution of the product from the previous step (1.2 g, 7.1 mmol) in MeOH (20 mL) was added NaBH$_4$ (1.1 g, 29 mmol) portionwise. The resulting mixture was stirred at RT for 0.5 h, the reaction mixture was concentrated in vacuo. The residue was dissolved in EtOAc (50 mL), washed with brine (50 mL×3), and concentrated to give the title compound as a brown solid (970 mg, crude).

MS (ES+) $C_7H_8FNO$ requires: 141, found: 142 $[M+H]^+$.

(2-(4-Methoxybenzylamino)-5-methylpyridin-4-yl)methanol

A solution of (2-fluoro-5-methylpyridin-4-yl)methanol (0.97 g, 6.9 mmol) in 4-methoxybenzylamine (5 mL) was sealed and stirred at 135° C. for 72 hours. The reaction mixture was cooled to RT, and then purified by silica gel column chromatography (DCM:MeOH=100:3) to give the title compound as a brown solid (800 mg, crude).

MS (ES+) $C_{15}H_{18}N_2O_2$ requires: 258, found: 259 $[M+H]^+$.

2-(4-Methoxybenzylamino)-5-methylisonicotinaldehyde

To a solution of the product from the previous step (0.8 g, 3.1 mmol) in CH$_2$Cl$_2$ (300 mL) was added MnO$_2$ (5.4 g, 62 mmol), The mixture was stirred at RT overnight, then filtered. The filtrate was concentrated under reduced pressure, and the obtained residue was purified by silica gel column chromatography (Petroleum ether:EtOAc=4:1) to give the title compound as a brown solid (720 mg, 90%).

MS (ES+) $C_{15}H_{16}N_2O_2$ requires: 256, found: 257 $[M+H]^+$.

(3,5-Dichloropyrazin-2-yl)(2-(4-methoxybenzylamino)-5-methyl pyridin-4-yl)methanol To a −78° C. solution of LDA (2.6 mL, 5.2 mmol) in dry THF (10 mL) under argon was added 2,6-dichloropyrazine (390 mg, 26 mmol) in THF (4 mL) dropwise at −78° C. The resulting solution was stirred at −78° C. for 1 h, then the product from the previous step (670 mg, 2.6 mmol) in THF (4 mL) was added to the mixture dropwise at −78° C. The resulting solution was stirred at −78° C. for 1 h, then quenched with HCl (1.8 mL)/EtOH (7.5 mL)/THF (9.0 mL) mixture, and warmed to RT. The reaction mixture was diluted with sat. aq. NaHCO$_3$ solution and extracted with EtOAc. The organic layer was separated and washed with brine, dried over Na$_2$SO$_4$, filtered, and concentrated under reduced pressure. The residue was purified by silica gel column chromatography (Petroleum ether:EtOAc=4:1) and further purified with Pre-HPLC to give the title compound as a yellow solid (80 mg, 6%).

MS (ES+) $C_{19}H_{18}Cl_2N_4O_2$ requires: 404, found: 405 $[M+H]^+$.

(3,5-Dichloropyrazin-2-yl)(2-(4-methoxybenzylamino)-5-methyl pyridin-4-yl)methanone To a solution of the product from the previous step (80 mg, 0.20 mmol) in CH$_2$Cl$_2$ (10 mL) was added Dess-Martin periodinane (127 mg, 0.3 mmol) at 0° C., the mixture was stirred at 0° C. for 1 hour, then another batch of Dess-Martin periodinane (127 mg, 0.3 mmol) was added and the mixture was stirred for another 4 hours at 0° C. The mixture was washed with aq. NaHCO$_3$ dried over MgSO$_4$, and concentrated under reduced pressure, and the residue was purified by silica gel column chromatography (Petroleum ether:EtOAc=2:1) to give the title compound as a brown solid (20 mg, 25%).

MS (ES+) $C_{19}H_{16}Cl_2N_4O_2$ requires: 402, found: 403 $[M+H]^+$.

Intermediate 119 methyl 3-((3S,4S)-4-((tert-butoxycarbonyl)amino)-3-methyl-2-oxa-8-azaspiro[4.5]decan-8-yl)-5-chloropyrazine-2-carboxylate

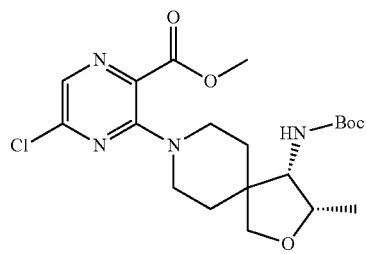 [SMILES: COC(=O)c1ncc(Cl)nc1N1CCC2(CC1)CO[C@@H](C)[C@H]2NC(=O)OC(C)(C)C]

Methyl 3-((3S,4S)-4-amino-3-methyl-2-oxa-8-azaspiro[4.5]decan-8-yl)-5-chloropyrazine-2-carboxylate To a solution of (3S,4S)-3-methyl-2-oxa-8-azaspiro[4.5]decan-4-amine dihydrochloride (5.1 g, 20.97 mmol) in Dioxane (105 ml) were added methyl 3,5-dichloropyrazine-2-carboxylate (4.34 g, 20.97 mmol) and Hunig's Base (18.32 ml, 105 mmol) and the resulting mixture was stirred at 24° C. for 18 h. H2O (20 mL) was added, and the layers were separated. The aqueous phase was extracted with EtOAc (3×20 mL), the combined organic layers were washed with sat NaCl, dried over Na2SO4, filtered and concentrated under reduced pressure. The residue was purified via silica gel chromatography (0-100% EtOAc in hexanes to give methyl 3-((3S,4S)-4-amino-3-methyl-2-oxa-8-azaspiro[4.5]decan-8-yl)-5-chloropyrazine-2-carboxylate (1.6 g, 4.69 mmol, 22.38% yield) as a pale yellow liquid. Mass:

MS (ES+) C15H21ClN4O3 requires: 340, found: 341 [M+Na]$^+$.

Methyl 3-((3S,4S)-4-((tert-butoxycarbonyl)amino)-3-methyl-2-oxa-8-azaspiro[4.5]decan-8-yl)-5-chloropyrazine-2-carboxylate To a solution of methyl 3-((3S,4S)-4-amino-3-methyl-2-oxa-8-azaspiro[4.5]decan-8-yl)-5-chloropyrazine-2-carboxylate (5.1 g, 14.96 mmol) in THF (100 ml) were added BOC-Anhydride (4.17 ml, 17.96 mmol) and TEA (2.503 ml, 17.96 mmol) and the resulting mixture was stirred at 25° C. for 8 h. H2O (20 mL) was added, and the layers were separated. The aqueous phase was extracted with EtOAc (3×20 mL), the combined organic layers were washed with sat NaCl, dried over Na2SO4, filtered and concentrated under reduced pressure. The residue was purified via silica gel chromatography (0-10% EtOAc in hexanes to give methyl 3-((3S,4S)-4-((tert-butoxycarbonyl)amino)-3-methyl-2-oxa-8-azaspiro[4.5]decan-8-yl)-5-chloropyrazine-2-carboxylate (6 g, 13.61 mmol, 91% yield) as a yellow liquid. Mass: MS (ES+) C20H29ClN4O5 requires: 440, found: 463 [M+Na]$^+$.

Intermediate 120

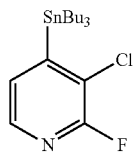

3-Chloro-2-fluoro-4-(tributylstannyl)pyridine

To a solution of 3-chloro-2-fluoro-4-iodopyridine (500 mg, 1.945 mmol) in i-PrOH (20 mL) were added Sn2Bu6 (2.25 g, 3.891 mmol), Pd2(dba)3 (178 mg, 0.194 mmol), and DIPEA (752 mg, 5.836 mmol), flushed with Ar and stirred at 25° C. for 48 hours. The volitiles were removed under reduced pressure and the residue was purified via silica gel chromatography (100% hexanes) to give the title compound as a colorless oil (700 mg, 80%). MS (ES+) C17H29ClFNSn requires: 421, found: 422 [M+H]$^+$.

Intermediate 121

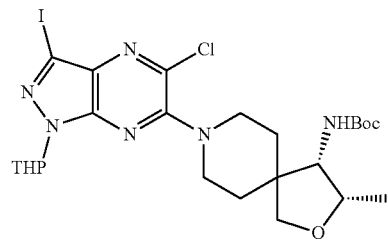

Step 1: Ethyl 2-(3,5-dichloropyrazin-2-yl)-2-oxoacetate

To a cooled (−78° C., internal thermometer) solution of 2,6-dichloropyrazine (24) (25 g, 160 mmol) and diethyl oxalate (25 g, 170 mmol) in 500 mL of anhydrous THF under N2 was added LDA (85 mL, 2M) dropwise so as to maintain the −78° C. internal temperature. The reaction was quenched cold 15 min after the addition was complete by the dropwise addition of acetic acid (9.6 mL, 160 mmol). The reaction mixture was poured into saturated NH4Cl solution and extracted with EtOAc (3×500 mL). The combined organic layers were dried over Na2SO4, filtered and concentrated in vacuo to get the crude product which was purified by silica gel chromatography with a 0-10% ethyl acetate/petroleum gradient as eluent to give the product (9 g, 22%) as a brown oil. 1H NMR (400 MHz, CDCl3, two rotamers) δ 8.61 (s, 1H), 8.50 (s, 1H), 4.45 (q, J=7.1 Hz, 2H), 4.33 (q, J=7.1 Hz, 2H), 1.41 (t, J=7.2 Hz, 3H), 1.27 (t, J=7.1 Hz, 3H). MS (ES+): m/z 249.9 (M+1). GCMS: 100%.

Step 2: (Z)-Ethyl 2-(3,5-dichloropyrazin-2-yl)-2-hydrazonoacetate

To a solution of hydrazine hydrate (3.4 g, 69 mmol) in 50 mL of ethanol at 0° C. was added hydrochloride aqueous(6 M, 11.5 mL, 69 mmol) dropwise. Then ethyl 2-(3,5-dichloropyrazin-2-yl)-2-oxoacetate (17 g, 69 mmol) in 45 mL of EtOH was added dropwise to the mixture. The reaction mixture was heated to 80° C. for 2 h. It was then cooled, poured into saturated aqueous NaHCO3 solution, and extracted with EtOAc (3×800 mL). The organic layers were combined, dried over Na2SO4, and concentrated invacuo to give (Z)-ethyl dichloropyrazin-2-yl)-2-hydrazonoacetate (17.6 g, 98%) as a brown oil which was used in the next step directly. MS (ES+) C8H8Cl2N4O2 requires: 262, found: 263 [M+H]$^+$.

Step 3: Ethyl 6-chloro-1H-pyrazolo[3,4-b]pyrazine-3-carboxylate

To a solution of (Z)-ethyl 2-(3,5-dichloropyrazin-2-yl)-2-hydrazonoacetate (17.6 g, 67 mmol) in 300 mL of THF at 0° C. was added NaH (3.2 g, 134 mmol) slowly in portions. The reaction mixture was warmed to rt for 30 min. The reaction was quenched with saturated NH4Cl solution and then poured into saturated NH4Cl solution. The pH of the aqueous layer was adjusted to 5 with 1 N hydrochloride aqueous, and it was then extracted with EA (3×500 mL). The combined organic layers were dried over Na2SO4, filtered and concentrated in vacuo to give the crude product which was recrystallized with EA to give ethyl 6-chloro-1H-pyrazolo

[3,4-b]pyrazine-3-carboxylate (5.3 g, 35%) as a pale-yellow solid. MS (ES+) C8H7ClN4O2 requires: 226, found: 227 [M+H]+.

Step 4: 6-Chloro-1H-pyrazolo[3,4-b]pyrazine-3-carboxylic Acid

A solution of ethyl 6-chloro-1H-pyrazolo[3,4-b]pyrazine-3-carboxylate (5 g, 22 mmol) in 6N HCl (30 mL) was stirred at 100° C. for 16 h. Then the precipitate was filtered, washed with water and dried to give 6-chloro-1H-pyrazolo[3,4-b]pyrazine-3-carboxylic acid (3.7 g, 84%) as a brown solid. MS (ES+) C6H3ClN4O2 requires: 198, found: 199 [M+H]+.

Step 5: 6-Chloro-3-iodo-1H-pyrazolo[3,4-b]pyrazine

To a stirred solution of 6-chloro-1H-pyrazolo[3,4-b]pyrazine-3-carboxylic acid (2.0 g, 10 mmol) in DCE/H2O (20/20 mL) was added NaHCO$_3$ (2.5 g, 30 mmol), follow by added NaI (3.9 g, 26 mmol), I$_2$(3.3 g, 13 mmol). The resulting mixture was stirred at 100° C. for 1 h. The mixture was poured into water and extracted with EtOAc (3×300 mL). The combined organic layers were washed with 10% Na$_2$S$_2$O$_3$ (500 mL) and saturated NaHCO$_3$(500 mL). Then organic layers were dried over Na$_2$SO$_4$, filtered and concentrated in vacuo to give the crude product which was washed with EtOAc. The precipitate was filtered to give 6-chloro-3-iodo-1H-pyrazolo[3,4-b]pyrazine (1.6 g, 57%) as a yellow solid. MS (ES+) C5H2ClIN4 requires: 280, found: 281 [M+H]+.

Step 6: 6-Chloro-3-iodo-1-(tetrahydro-2H-pyran-2-yl)-1H-pyrazolo[3,4-b]pyrazine

A mixture of 6-chloro-3-iodo-1H-pyrazolo[3,4-b]pyrazine (5 g, 17.857 mmol), DHP (3 g, 35.714 mmol) in EtOAc (100 ml) was added TosOH (300 mg, 1.78 mmol) stirred at 60° C. for 2 hours, LCMS monitored, the mixture was purified via silica gel chromatography (0-50% EtOAc in PE) to give the title compound as a white solid (5.1 g, 78%). MS (ES+) C10H10ClN4O requires: 363.96, found: 365 [M+H]+.

Step 7: N-((3S,4S)-8-(3-Iodo-1-(tetrahydro-2H-pyran-2-yl)-1H-pyrazolo[3,4-b]pyrazin-6-yl)-3-methyl-2-oxa-8-azaspiro[4.5]decan-4-yl)-2-methylpropane-2-sulfinamide A mixture of 6-chloro-3-iodo-1-(tetrahydro-2H-pyran-2-yl)-1H-pyrazolo[3,4-b]pyrazine (1 g, 2.74 mmol), tert-butyl (3S,4S)-3-methyl-2-oxa-8-azaspiro[4.5]decan-4-ylcarbamate (740 mg, 2.74 mmol), and DIPEA (1.06 g, 8.22 mmol) in DMF (10 ml) stirred at 100° C. for 3 h, LCMS monitored, concentrated and purified via silica gel chromatography (30-50% EA in PE) to give the title compound as a yellow solid (1.3 g, 78%). MS (ES+) C23H35IN6O3S requires: 602, found: 603 [M+H]+.

Step 8: (3S,4S)-8-(3-Iodo-1H-pyrazolo[3,4-b]pyrazin-6-yl)-3-methyl-2-oxa-8-azaspiro[4.5]decan-4-amine A solution of N-((3S,4S)-8-(3-iodo-1-(tetrahydro-2H-pyran-2-yl)-1H-pyrazolo[3,4-b]pyrazin-6-yl)-3-methyl-2-oxa-8-azaspiro[4.5]decan-4-yl)-2-methylpropane-2-sulfinamide (1.3 g, 2.16 mmol) in 4N HCl (10 ml in dioxane) stirred at 50° C. for 1 h, LCMS monitored, concentrated to obtain the title compound as a yellow solid (630 mg, crude). MS (ES+) C14H19IN6O requires: 414, found: 415 [M+H]+.

Step 9: Tert-butyl (3S,4S)-8-(3-iodo-1H-pyrazolo[3,4-b]pyrazin-6-yl)-3-methyl-2-oxa-8-azaspiro[4.5]decan-4-ylcarbamate A mixture of (3S,4S)-8-(3-iodo-1H-pyrazolo[3,4-b]pyrazin-6-yl)-3-methyl-2-oxa-8-azaspiro[4.5]decan-4-amine (600 mg, 1.45 mmol), Boc2O (380 mg, 1.74 mmol) and Et$_3$N (440 mg, 4.35 mmol) was stirred at rt for 16 h, LCMS monitored, concentrated and purified via silica gel chromatography (0-10% MeOH in DCM) to give the title compound as a yellow solid (720 mg, 92%). MS (ES+) C19H27IN6O3 requires: 514, found: 515 [M+H]+.

Step 10: Tert-butyl (3S,4S)-8-(3-iodo-1-(tetrahydro-2H-pyran-2-yl)-1H-pyrazolo[3,4-b]pyrazin-6-yl)-3-methyl-2-oxa-8-azaspiro[4.5]decan-4-ylcarbamate A mixture of tert-butyl (3 S,4 S)-8-(3-iodo-1H-pyrazolo[3,4-b]pyrazin-6-yl)-3-methyl-2-oxa-8-azaspiro[4.5]decan-4-ylcarbamate (720 mg, 1.4 mmol), DHP (840 mg, 8.4 mmol) and PPTs (10 mg, Cat.) was flushed with Ar refluxed overnight, LCMS monitored, concentrated and purified via silica gel chromatography (0-10% MeOH in DCM) to give the title compound as a yellow solid (750 mg, 89%). MS (ES+) C24H35IN6O4 requires: 598, found: 599 [M+H]+.

Step 11: Tert-butyl (3S,4S)-8-(5-chloro-3-iodo-1-(tetrahydro-2H-pyran-2-yl)-1H-pyrazolo[3,4-b]pyrazin-6-yl)-3-methyl-2-oxa-8-azaspiro[4.5]decan-4-ylcarbamate To a solution of tert-butyl (3S,4S)-8-(3-iodo-1-(tetrahydro-2H-pyran-2-yl)-1H-pyrazolo[3,4-b]pyrazin-6-yl)-3-methyl-2-oxa-8-azaspiro[4.5]decan-4-ylcarbamate (400 mg, 0.669 mmol) in DMF (4 ml) was added NCS (267 mg, 2.007 mmol), the mixture was stirred at room temperature for 1 hours, LCMS monitored, The mixture was quenched with a drop of NaHSO$_3$ (sat. aq.) and brine (15 ml), extracted with EtOAc (15 ml×3), washed with water (15 ml), brine (15 ml), concentrated to obtained the title compound as a light yellow solid (300 mg, 75%). MS (ES+) C24H34ClIN6O4 requires: 632, found: 633 [M+H]+.

Intermediate 122

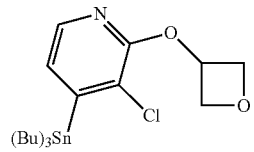

Step 1: 3-Chloro-4-iodo-2-(oxetan-3-yloxy)pyridine

A solution of oxetan-3-ol (345 mg, 0.467 mmol) in DMF (10 ml) was added NaH (60%, 202 mg, 0.56 mmol) at 0° C. and stirred for 1 hour, 3-chloro-2-fluoro-4-iodopyridine (1 g, 0.389 mmol) in DMF (2 ml) was added, warmed to room temperature slowly and stirred for 1 hour, quenched with NH$_4$Cl (sat. aq, 1 ml), added water 20 ml, stirred at 0° C. for 10 min, filtered to obtained the title compound as a white solid (1.1 g, 91%). MS (ES+) C8H7ClINO2 requires: 311, found: 312[M+H]⁺.

Step 2: 3-Chloro-2-(oxetan-3-yloxy)-4-(tributylstannyl)pyridine

A mixture of 3-chloro-4-iodo-2-(oxetan-3-yloxy)pyridine (1 g, 3.89 mmol), Pd₂(dba)₃ (356 mg, 0.39 mmol), Bu₆Sn₂ (3.44 g, 5.83 mmol), DIPEA (1.5 g, 11.67 mmol) in i-PrOH (20 ml), flushed with Ar, stirred at RT for 48 hours, LCMS monitored, The mixture was purified via silica gel chromatography (0-100% EtOAc in PE) to give the title compound as colorless oil (800 mg, 52%). MS (ES+) C20H34ClNO2Sn requires: 475, found: 476 [M+H]⁺. 1H NMR (500 MHz, CDCl3) δ 7.98-7.77 (m, 1H), 6.97-6.68 (m, 1H), 5.70-5.54 (m, 1H), 5.00 (t, J=7.2 Hz, 2H), 4.88-4.67 (m, 2H), 1.56-1.43 (m, 6H), 1.42-1.27 (m, 6H), 1.26-1.09 (m, 6H), 0.89 (t, J=7.3 Hz, 9H).

Intermediate 123

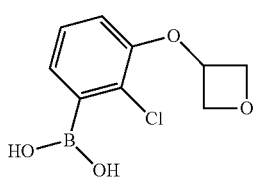

Step 1: 3-Tosyloxetane

A mixture of oxetan-3-ol (2 g, 27 mmol) in DCM (25 ml) was added DIPEA (6.97 g, 54.1 mmol), TosCl (6.16 g, 32.4 mmol), the mixture was stirred at room temperature overnight, LCMS monitored. The mixture was washed with aq. NH₄Cl (25 ml×3) and brine (25 ml), purified via silica gel chromatography (0-20% EtOAc in PE) to give the title compound as a white solid (4 g, 70%). MS (ES+) C10H12O3S requires: 212, found: 213 [M+H]⁺.

Step 2: 3-(3-Bromo-2-chlorophenoxy)oxetane

A mixture of 3-bromo-2-chlorophenol (2.1 g, 10.2 mmol), 3-tosyloxetane (3.5 g, 15.3 mmol), KI (168 mg, 1.02 mmol), Cs₂CO₃ (6.65 g, 20.4 mmol) in DMF (20 ml) was stirred at 80° C. overnight, LCMS monitored. The mixture was poured into water (150 ml), extracted with EtOAc (75 ml×3), washed with sat. NH₄Cl (100 ml×2) and brine (100 ml), purified via silica gel chromatography (0-20% EA in PE) to give the title compound as a white solid (1.5 g, 56%). MS (ES+) C9H8BrClO2 requires: 261.94, found: 263 [M+H]⁺.

Step 3: 2-(2-Chloro-3-(oxetan-3-yloxy)phenyl)-4,4,5,5-tetramethyl-1,3,2-dioxaborolane A mixture of 3-(3-bromo-2-chlorophenoxy)oxetane (750 mg, 2.85 mmol), 4,4,4',4',5,5,5',5'-octamethyl-2,2'-bi(1,3,2-dioxaborolane) (1.45 g, 5.703 mmol), Pd(dppf)Cl₂ (208 mg, 0.285 mmol), KOAc (838 mg, 8.555 mmol) in dioxane (20 ml) flushed with Ar and refluxed overnight, LCMS monitored. The mixture was purified via silica gel chromatography (0-25% EtOAc in PE) to give the title compound as a white solid (0.8 g, 90%). MS (ES+) C15H2OBClO4 requires: 310, found: 311[M+H]⁺. 1H NMR (400 MHz, CDCl3) δ 7.28 (dd, J=7.4, 1.3 Hz, 1H), 7.15 (t, J=7.7 Hz, 1H), 6.56 (dd, J=8.1, 1.3 Hz, 1H), 5.30-5.12 (m, 1H), 4.96 (t, J=6.9 Hz, 2H), 4.90-4.75 (m, 2H), 1.38 (s, 12H).

Intermediate 124

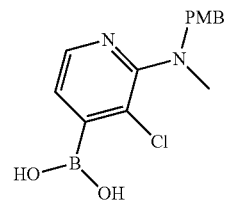

Step 1: 3-Chloro-N-methylpyridin-2-amine

A mixture of 2,3-dichloropyridine (10 g) in MeNH₂ (40%, aq) was stirred in a sealed tube at 125° C. overnight, The mixture was concentrated and extracted with EtOAc (100 ml×5) washed with brine (100 ml×2), concentrated to obtained the title compound as a colorless oil (7.5 g, 70%). MS (ES+) C6H7ClN2 requires: 142, found: 143 [M+H]⁺.

Step 2: 3-Chloro-N-(4-methoxybenzyl)-N-methylpyridin-2-amine

To a solution of 3-chloro-N-methylpyridin-2-amine (1 g, 7.04 mmol) in DMF (dry, 10 ml) was added NaH (338 mg, 8.45 mmol) at 0° C., then stirred at room temperature for 1 hour. PMBCl (1.65 g, 10.05 mmol) was added slowly at 0° C., warmed to room temperature overnight. The mixture was quenched with brine (20 ml) extracted with EtOAc (25 ml×3) washed with aq. NH4Cl (25 ml×2) and brine (25 ml), concentrated and purified via silica gel chromatography (10-50% EtOAc in PE) to give the title compound as a colorless oil (900 mg, 48%). MS (ES+) C14H15ClN2O requires: 262, found: 263 [M+H]⁺.

Step 3: 3-Chloro-2-((4-methoxybenzyl)(methyl)amino)pyridin-4-ylboronic Acid

To a solution of 3-chloro-N-(4-methoxybenzyl)-N-methylpyridin-2-amine (1 g, 3.816 mmol) in THF (10 ml) at −78° C. was added n-BuLi (2.4 ml, 1.6 M, 3.816 mmol) slowly, then stirred at this temperature for 40 min, i-PrO₃B (1.4 g, 7.633 mmol) was added at −78° C. After 2 hour, it was quenched with NH₄Cl (10 ml), adjust pH=6 with citric acid, extracted with EtOAc (20 ml×5), concentrated and purified via silica gel chromatography (0-2-% MeOH in DCM) to give the title compound as a brown solid (150 mg, crude). MS (ES+) C14H16BClN2O3 requires: 306, found: 307 [M+H]⁺.

SYNTHETIC SCHEMES

The following schemes can be used to practice the present invention.

Scheme I

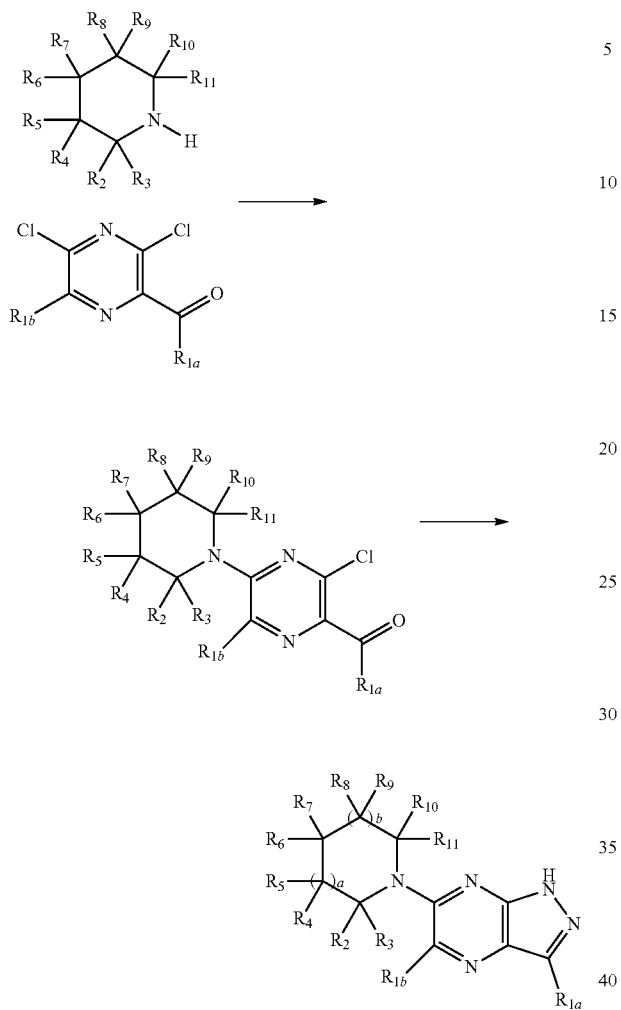

A general, non-limiting synthetic strategy for the disclosed compounds is illustrated in Scheme I, above. An appropriately substituted piperidine is condensed with a chlorinated pyrazine. The pyrazolo[3,4-b]pyrazine core formed on reaction of the intermediate with hydrazine. It will be appreciated that other synthetic routes may be available for practice of the present invention.

Scheme II

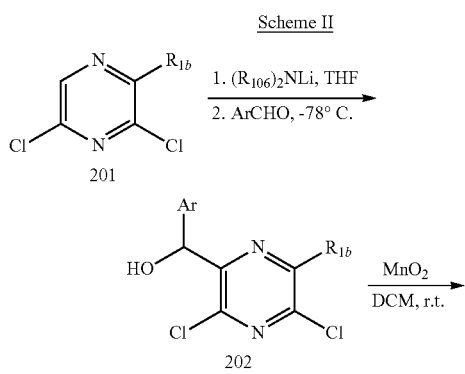

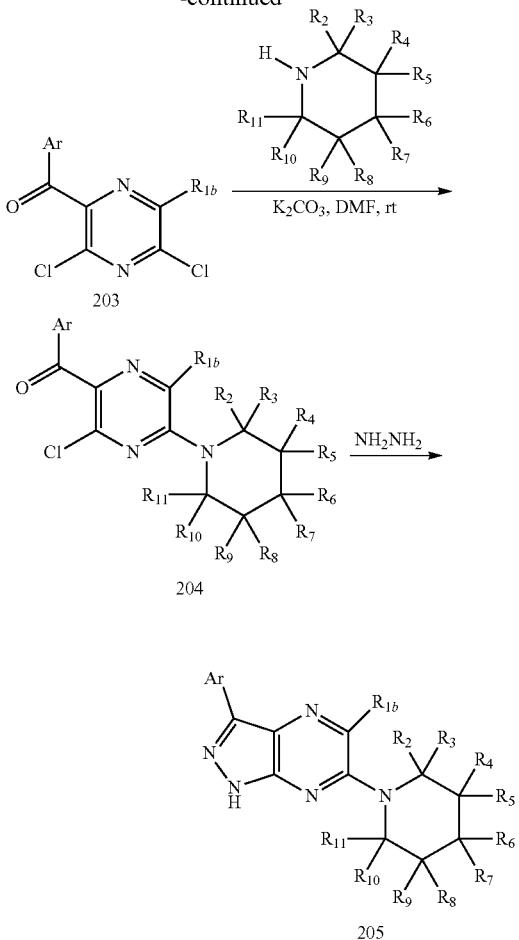

Examples disclosed herein can be synthesized using the general synthetic procedure set forth in Scheme II. Ortho metalation of the pyrazine 201 can be accomplished with a metalated secondary amine $(R_{106})_2NLi$, which can be prepared from $(R_{106})_2NH$ and BuLi (not shown). Without limitation, examples of suitable secondary amines $(R_{106})_2NH$ for this transformation include diiosopropylamine and 2,2,6,6-tetramethylpiperidine. The metalated pyrazine is condensed with a substituted aryl carboxaldehyde to give benzylic alcohol 202. Oxidation to the ketone 203 is followed by substitution of the aryl halide with an appropriately substituted piperidine to give amine 204. Reaction with hydrazine gives the pyrazolo[3,4-b]pyrazine ring of 205.

It will be apparent that Scheme II can be modified to accommodate functionality in the piperidine. A protected amine can be incorporated into the piperidine as an —$NHP_1$ group. In this scheme the group "$P_1$" is an appropriate amino protecting group. Without limitation, $P_1$ can be a carbamate protecting group such as Boc or CBz, or a labile aromatic protecting group, such as p-methoxybenzyl. The protecting group $P_1$ is removed from 205 to afford the product. A carbamate protecting group can be removed under acid conditions to afford the product.

Scheme III

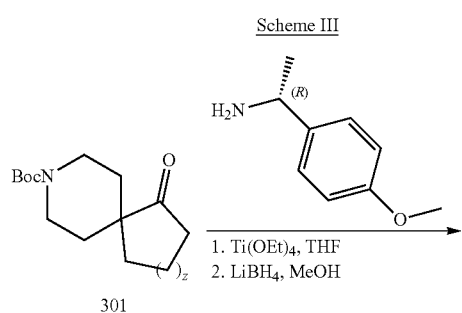

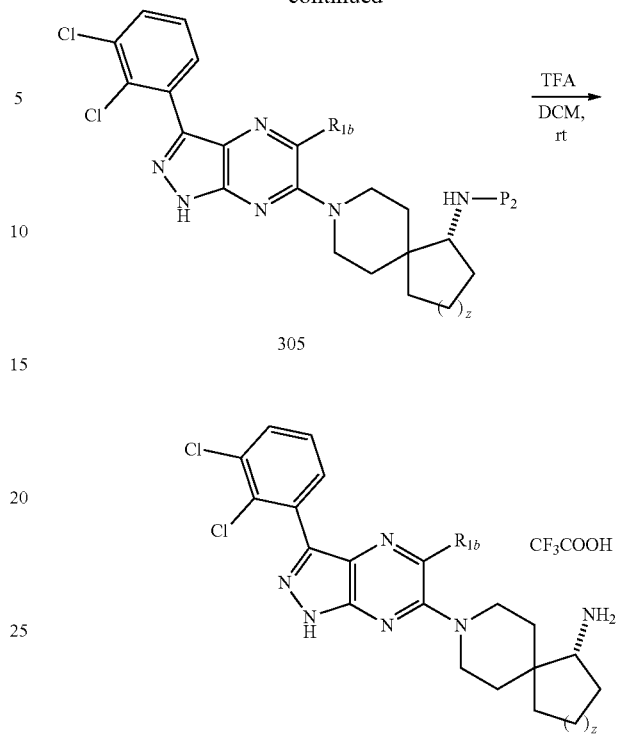

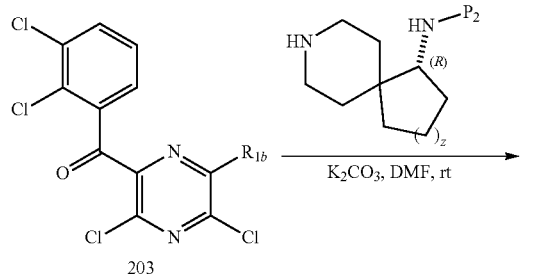

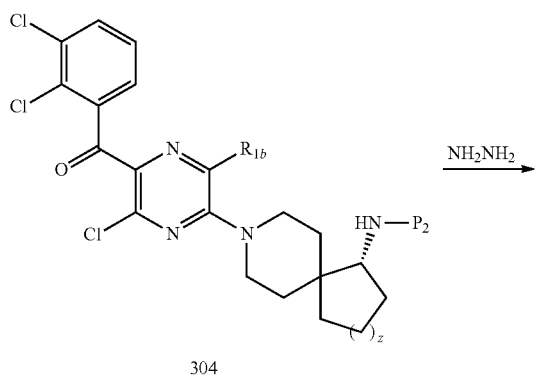

Examples disclosed herein can be synthesized using the general synthetic procedure set forth in Scheme III. Condensation of spiro ketone 301 (z=1) with enantiopure 1-(4-methoxy-phenyl)ethylamine), followed by reduction, gives chiral secondary amine 302. The Boc protecting group is removed under acidic conditions, giving amine 303. In this scheme, the symbol $P_2$ is intended to represent the 1-(4-methoxyphenyl)ethyl group. Reaction with a ketone such as 203 (Scheme II) affords amine 304. Reaction with hydrazine gives the pyrazolo[3,4-b]-pyrazine ring of 305. Finally, the 1-(4-methoxyphenyl)ethyl group is removed under acid conditions. This procedure can be modified to access spiro compounds of differing ring sizes, i.e., z≠1. The compound may then be isolated as the free base by methods known in the art.

Scheme IV

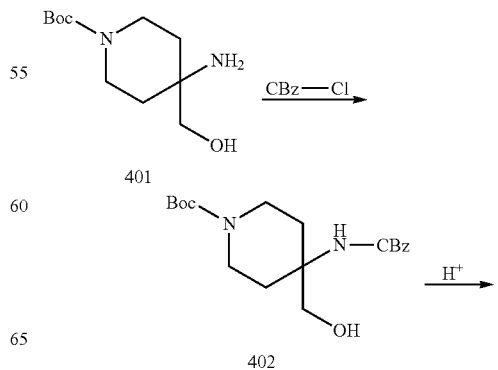

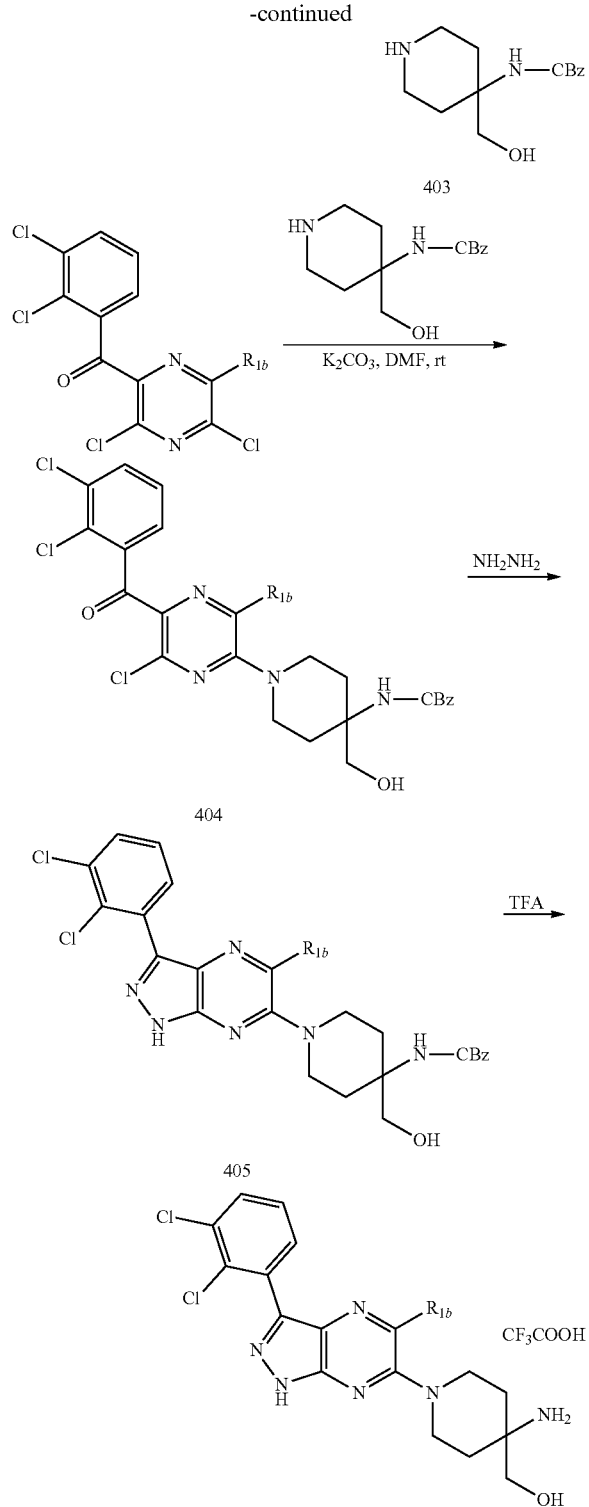

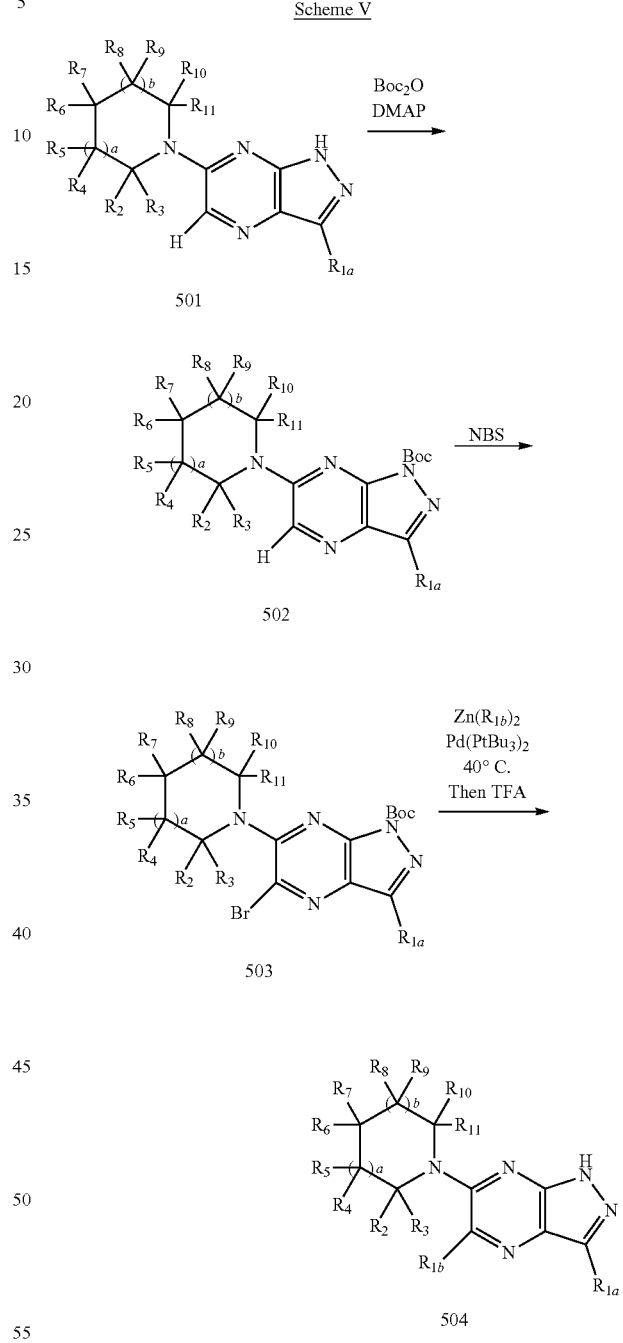

Examples disclosed herein can be synthesized using the general synthetic procedure set forth in Scheme IV. Reaction of primary amine 401 with CBz-Cl gives protected amine 402. The Boc protecting group is removed under acidic conditions, giving amine 403, and leaving the CBz group intact. Reaction with the previously presented ketone 203 affords amine 404. Reaction with hydrazine gives the pyrazolo[3,4-b]pyrazine ring of 405. Finally, the CBz group is removed under more vigorous acid conditions to give the product. The compound may then be isolated as the free base by methods known in the art.

Examples disclosed herein can be synthesized using the general synthetic procedure set forth in Scheme V. Reaction of pyrazolopyrazine 501 with Boc2O and DMAP gives protected heterocycle 502. The core can then be brominated using N-Bromosuccinimide to give 503. This bromo-heterocycle can then be cross-coupled with organozine reagents to provide a functionalized heterocycle, and removal of the Boc group furnished compounds of this invention. The desired compounds may then be isolated as the free bases or salts by methods known in the art.

Scheme VI

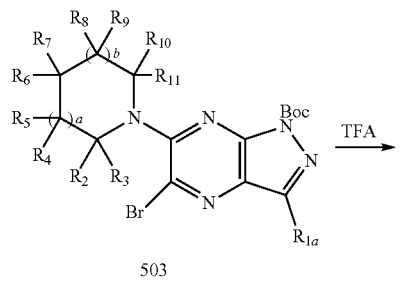
503

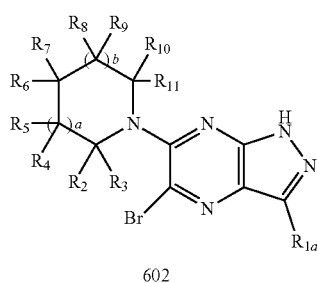
602

Examples disclosed herein can be synthesized using the general synthetic procedure set forth in Scheme VI. Reaction of bromopyrazolopyrazine 503 with TFA gives the furnished bromindated compounds 602 of this invention. The desired compounds may then be isolated as the free bases or salts by methods known in the art.

Scheme VII

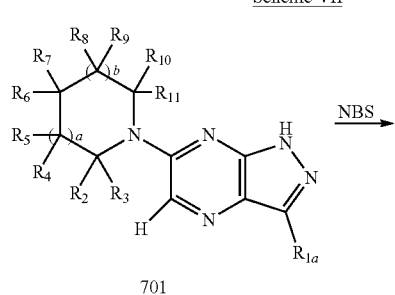
701

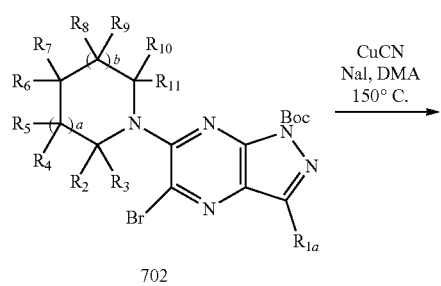
702

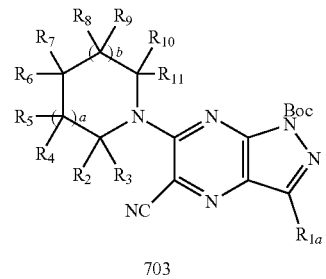
703

Examples disclosed herein can be synthesized using the general synthetic procedure set forth in Scheme VII. The pyrazolopyrazine 701 can be bromindated using N-Bromosuccinimide to give 702. This bromoheterocycle can then reacted with copper (I) cyanide and sodium iodide in DMA solvent at elevated temperature to a functionalized heterocycle 703 as compounds of this invention. The desired compounds may then be isolated as the free bases or salts by methods known in the art.

Scheme VIII

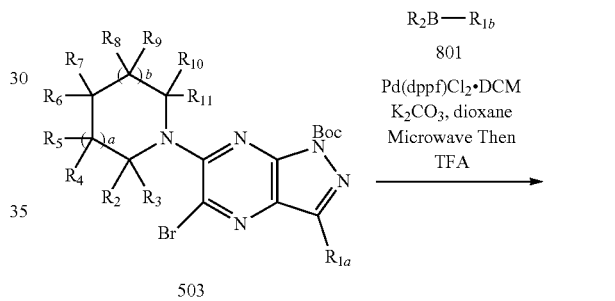
503

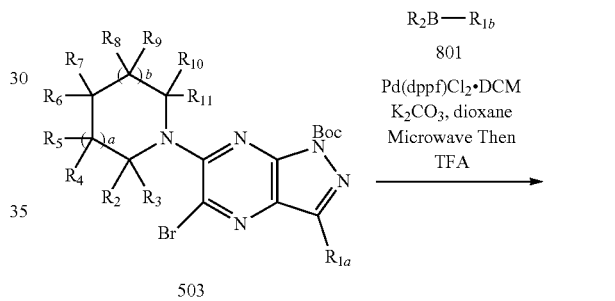
802

Examples disclosed herein can be synthesized using the general synthetic procedure set forth in Scheme VIII. Reaction of Boc-protect bromopyrazolopyrazine 503 with organoboronic acid and ester derivatives 801 under palladium catalysis in the presence of an inorganic base such as $K_2CO_3$ with thermal or microwave irradiation give functionalized heterocycles. Removal of the Boc group furnished compounds 802 of this invention. The desired compounds may then be isolated as the free bases or salts by methods known in the art.

Scheme IX

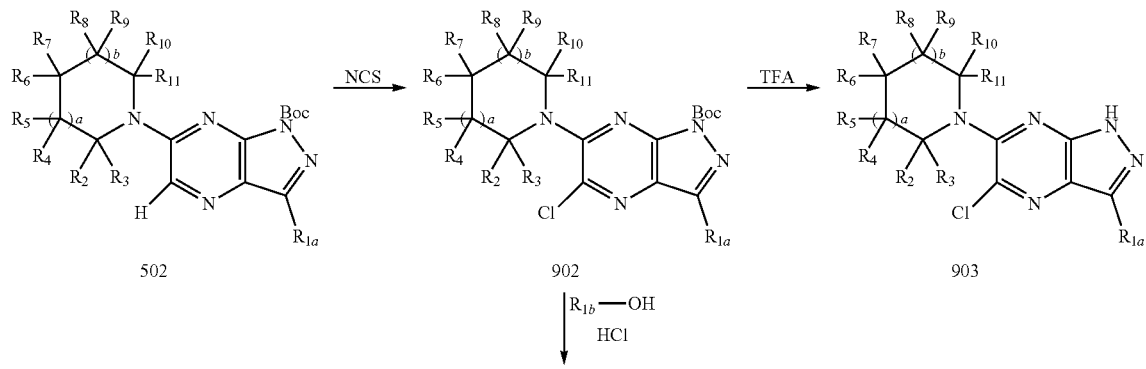

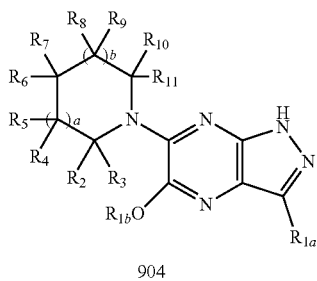

Examples disclosed herein can be synthesized using the general synthetic procedure set forth in Scheme IX. Reaction of Boc-protect pyrazolopyrazine 502 with N-chlorosuccinimide give the chlorinated heterocycle 902, this can then in turn be deprotected with TFA to give compound 903 of this invention. Alternatively 902 can be reacted with an alcohol in the presence of hydrochloric acid to give the ether containing compounds 904 of this invention. The desired compounds may then be isolated as the free bases or salts by methods known in the art.

Scheme X

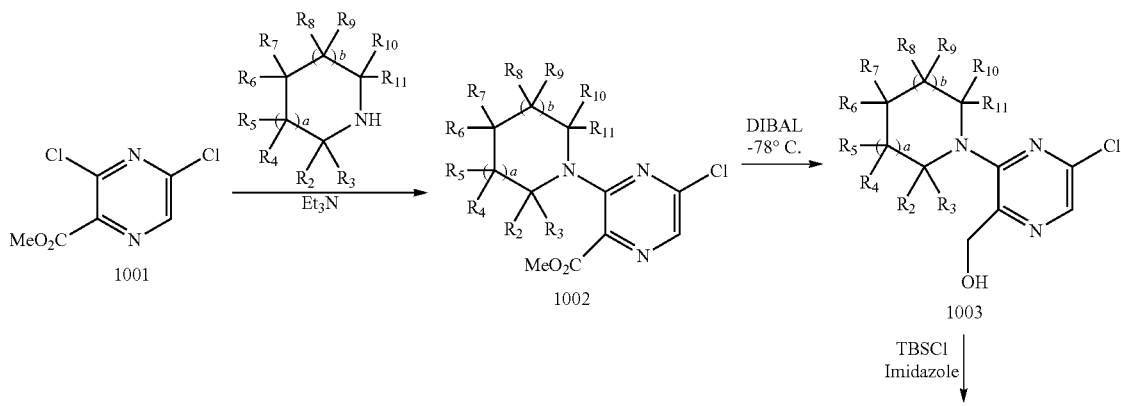

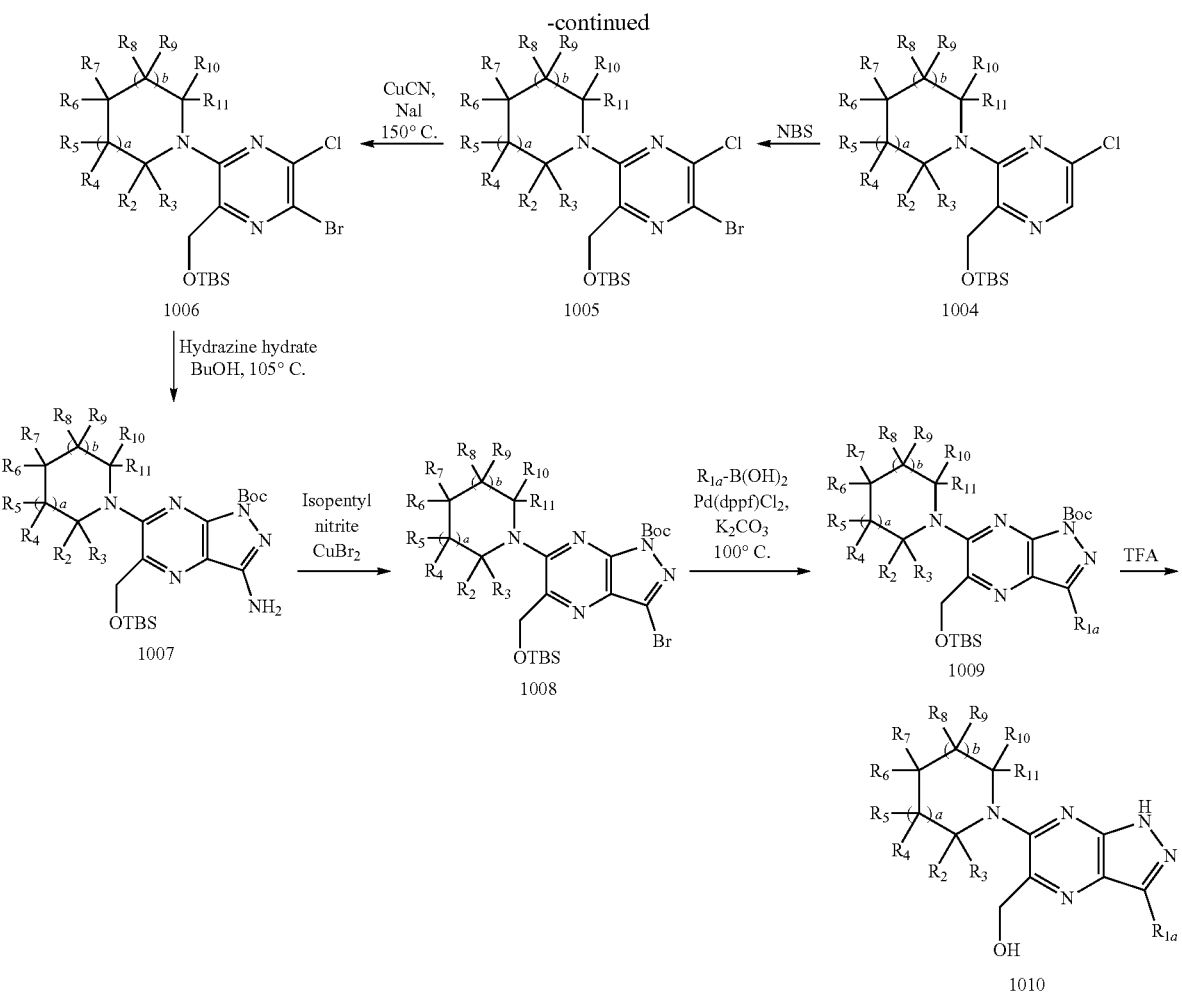

Examples disclosed herein can be synthesized using the general synthetic procedure set forth in Scheme X. Reaction of the dichloropyrazine 1001 with a cyclic amine elaborates the desired functionalized pyrazine 1002. In turn, this can be reduced with reducing agents such as DIBAL to give the desired alcohols 1003. The free hydroxyl group can then be protected by methods known to those in the art, for instance using TBS-Cl in the presence of imidazole, to yield the protected compound 1004. This functionalized pyrazine can be bromindated using NBS to yield compound 1005, which can then be converted to the pyrazine nitrile 1006 by reaction with copper (I) cyanide and sodium iodide at 150° C. Reaction of 1006 with hydrazine hydrate in an alcohol solvent, such as butanol, cyclizes to yield the pyrazolo-pyridzaine ring system 1007. The amino group can then be diazitized and converted into the corresponding hetrocyclic bromide 1008 by methods such as reaction with isopentyl nitrite and copper (II) bromide. Suzuki cross-coupling of 1008 with boronic acids and esters in the presence of palladium catalysis yields the functionalized compounds 1009. These can then be deprotected to yield compounds 1010 of this invention. The desired compounds may then be isolated as the free bases or salts by methods known in the art.

Scheme XI

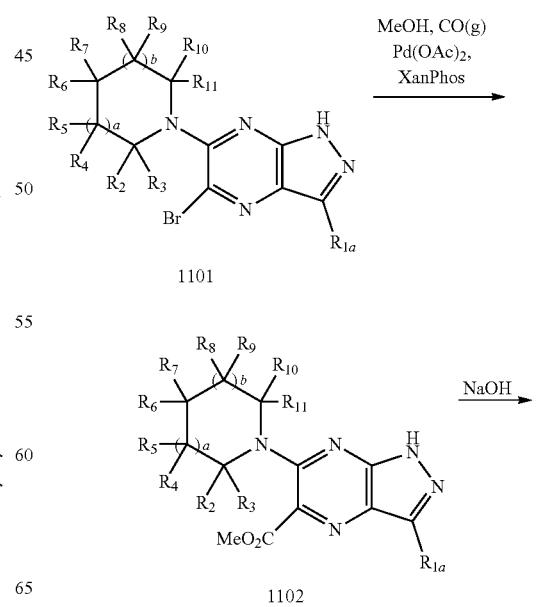

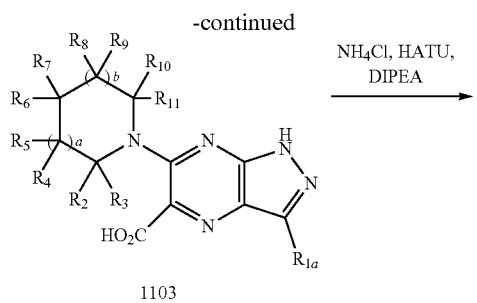

1103

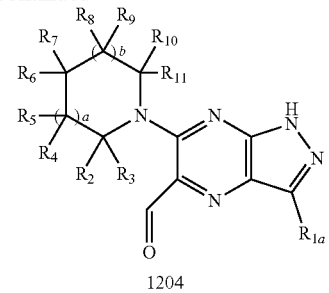

1204

Examples disclosed herein can be synthesized using the general synthetic procedure set forth in Scheme XII. The bromo-protect pyrazolopyrazine 1201 can be converted to the corresponding vinyl derivative 1203 by known methods, for instance by coupling with a vinyl boron derivative like 1202 using palladium catalysis (e.g. Pd(dppf)Cl2 and an inorganic base such as $K_2CO_3$). In turn, the vinyl group can be cleaved to liberate aldehydes 1204 of this invention, for example using a mixture of osium tetraoxide and sodium periodinate in solvents such as dioxane and water. The desired compounds may then be isolated as the free bases or salts by methods known in the art.

1104

Examples disclosed herein can be synthesized using the general synthetic procedure set forth in Scheme XI. The bromo-protect pyrazolopyrazine 1101 can be carbonylated by known methods, for instance with carbon monoxide gas in an alcohol solvent such as MeOH, using palladium catalysis (e.g. Pd(OAc)$_2$ and XanPhos) to yield esters such as 1102. In turn, these can be hydrolyzed with an inorganic base in a solvent such as THF and water at elevated temperature to give acid 1103. The acid can then be coupled with amines such as ammonium chloride with coupling reagents such as HATU in the presence of an organic base to give compounds 1104 of this invention. The desired compounds may then be isolated as the free bases or salts by methods known in the art.

Scheme XIII

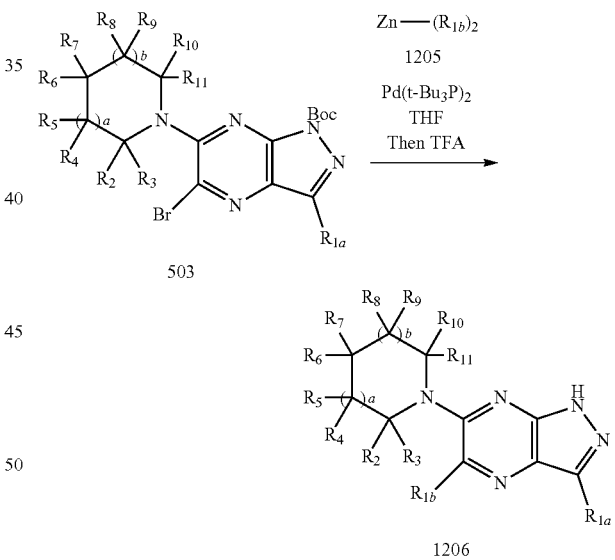

Scheme XII

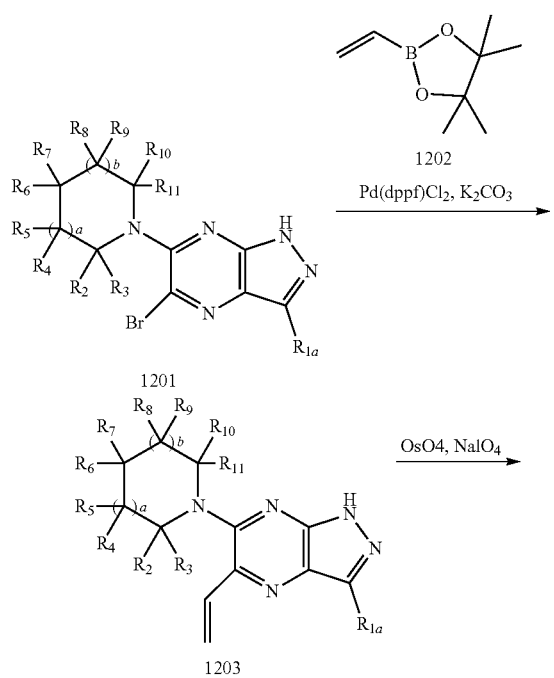

Examples disclosed herein can be synthesized using the general synthetic procedure set forth in Scheme XIII Reaction of Boc-protect bromopyrazolopyrazine 503 with organozinc derivatives 1205 under palladium catalysis to give functionalized heterocycles. Removal of the Boc group furnished compounds 1206 of this invention. The desired compounds may then be isolated as the free bases or salts by methods known in the art.

The invention is further illustrated by the following examples, which may be synthesized and isolated as free bases or as TFA salts.

Example 1: 1-(3-(2,3-dichlorophenyl)-5-methyl-1H-pyrazolo[3,4-b]pyrazin-6-yl)-4-methylpiperidin-4-amine

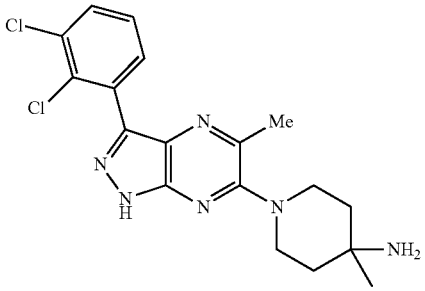 [SMILES: Cc1nc2c(-c3cccc(Cl)c3Cl)n[nH]c2nc1N1CCC(C)(N)CC1]

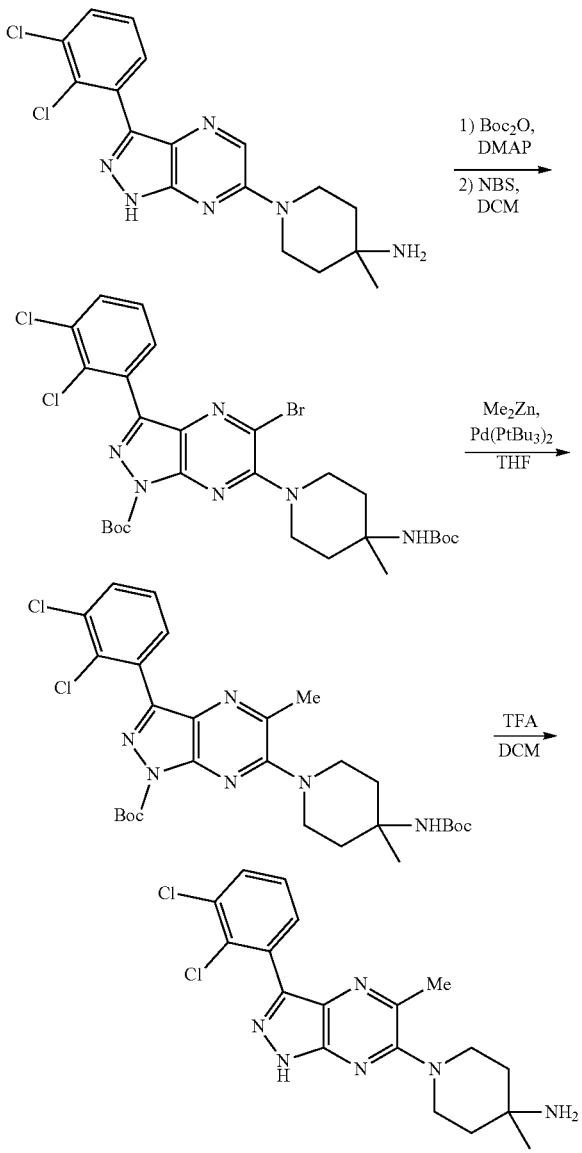

Scheme 1 tert-Butyl 6-(4-((tert-butoxycarbonyl)amino)-4-methylpiperidin-1-yl)-3-(2,3-dichlorophenyl)-1H-pyrazolo[3,4-b]pyrazine-1-carboxylate To a suspension of 1-(3-(2,3-dichlorophenyl)-1H-pyrazolo[3,4-b]pyrazin-6-yl)-4-methylpiperidin-4-amine (300 mg, 0.795 mmol) in THF (7.9 mL) were added DMAP (243 mg, 1.99 mmol) and $Boc_2O$ (462 μl, 1.99 mmol) and the resulting mixture was stirred at RT for 6 h. The volatiles were removed under reduced pressure. The residue was adsorbed onto silica gel and purified via flash chromatography (0-60% EtOAc in hexanes) to give the title compound (410 mg, 89%) as a yellow amorphous material. MS (ES+) $C_{27}H_{34}Cl_2N_6O_4$ requires: 576, found: 577 [M+H]$^+$.

tert-Butyl 5-bromo-6-(4-((tert-butoxycarbonyl)amino)-4-methylpiperidin-1-yl)-3-(2,3-dichlorophenyl)-1H-pyrazolo[3,4-b]pyrazine-1-carboxylate To a solution of tert-butyl 6-(4-((tert-butoxycarbonyl)amino)-4-methylpiperidin-1-yl)-3-(2,3-dichlorophenyl)-1H-pyrazolo[3,4-b]pyrazine-1-carboxylate (100 mg, 0.173 mmol) in DCM (1.7 mL) at 0° C. was added NBS (46 mg, 0.26 mmol) and the resulting mixture was allowed to warm to RT over 1 h. The volatiles were removed under reduced pressure. The residue was adsorbed onto silica gel and purified via flash chromatography (0-100% EtOAc in hexanes) to give the title compound (82 mg, 72%) as an orange amorphous material. MS (ES+) $C_{27}H_{33}BrCl_2N_6O_4$ requires: 654, found: 655 [M+H]$^+$.

tert-Butyl 6-(4-((tert-butoxycarbonyl)amino)-4-methylpiperidin-1-yl)-3-(2,3-dichlorophenyl)-5-methyl-1H-pyrazolo[3,4-b]pyrazine-1-carboxylate A solution of bis(tri-t-butylphosphine)palladium(O) (3.1 mg, 6.1 μmol) and tert-butyl 5-bromo-6-(4-((tert-butoxycarbonyl)amino)-4-methylpiperidin-1-yl)-3-(2,3-dichlorophenyl)-1H-pyrazolo[3,4-b]pyrazine-1-carboxylate (80 mg, 0.12 mmol) in THF (1.2 mL) was degassed with $N_2$ for 1 min. Dimethylzinc in heptane (244 μl, 0.244 mmol, 1M) was added and the mixture was degassed with $N_2$ for an additional 2 min. The reaction mixture was heated to 40° C. and stirred for 1 h. The reaction was quenched slowly with MeOH (1 mL). The volatiles were removed under reduced pressure. The residue was purified via silica gel chromatography (0-100% EtOAc in hexanes) to give the title compound (41 mg, 57%) as a pale yellow amorphous material. MS (ES+) $C_{28}H_{36}Cl_2N_6O_4$ requires: 590, found: 591 [M+H]$^+$.

1-(3-(2,3-dichlorophenyl)-5-methyl-1H-pyrazolo[3,4-b]pyrazin-6-yl)-4-methylpiperidin-4-amine To a solution of tert-butyl 6-(4-((tert-butoxycarbonyl)amino)-4-methylpiperidin-1-yl)-3-(2,3-dichlorophenyl)-5-methyl-1H-pyrazolo[3,4-b]pyrazine-1-carboxylate (40 mg, 0.068 mmol) in DCM (676 μl) was added trifluoroacetic acid (208 μl, 2.70 mmol) and the resulting mixture was stirred at RT for 1 h. The volatiles were removed under reduced pressure. The residue was purified by mass-triggered preparative HPLC (Mobile phase: A=0.1% TFA/$H_2O$, B=0.1% TFA/MeCN; Gradient: B=10-90%; 12 min; Column: C18) to give the title compound (16 mg, 60%) as a off-white solid. MS (ES+) $C_{18}H_{20}Cl_2N_6$ requires: 390, found: 391 [M+H]$^+$. $^1$H NMR (600 MHz, Methanol-$d_4$) δ 7.67 (d, J=8.1 Hz, 1H), 7.57 (d, J=7.6 Hz, 1H), 7.43 (t, J=7.9 Hz, 1H), 3.70-3.61 (m, 2H), 3.30-3.26 (m, 2H), 2.62 (s, 3H), 2.10-2.00 (m, 2H), 1.99-1.89 (m, 2H), 1.52 (s, 3H).

Example 2: 1-(5-bromo-3-(2,3-dichlorophenyl)-1H-pyrazolo[3,4-b]pyrazin-6-yl)-4-methylpiperidin-4-amine

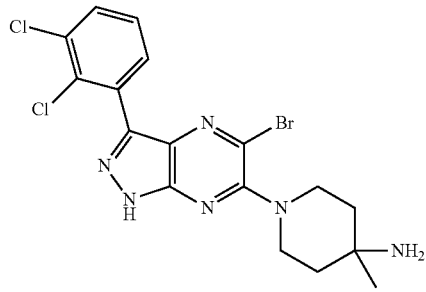 [SMILES: CC1(N)CCN(c2nc3[nH]nc(-c4cccc(Cl)c4Cl)c3nc2Br)CC1]

1-(5-Bromo-3-(2,3-dichlorophenyl)-1H-pyrazolo[3,4-b]pyrazin-6-yl)-4-methylpiperidin-4-amine To a solution of tert-butyl (1-(5-bromo-3-(2,3-dichlorophenyl)-1H-pyrazolo[3,4-b]pyrazin-6-yl)-4-methylpiperidin-4-yl)carbamate (15 mg, 0.027 mmol) in DCM (539 µl) was added trifluoroacetic acid (104 µl, 1.35 mmol) and the resulting mixture was stirred at RT for 2 h. The volatiles were removed under reduced pressure. The residue was purified by mass-triggered preparative HPLC (Mobile phase: A=0.1% TFA/H$_2$O, B=0.1% TFA/MeCN; Gradient: B=10-90%; 12 min; Column: C18) to give the title compound (3 mg, 24%) as a white solid. MS (ES+) C$_{17}$H$_{17}$BrCl$_2$N$_6$ requires: 454 found: 455 [M+H]$^+$. $^1$H NMR (500 MHz, DMSO-d$_6$) δ 14.11 (s, 1H), 7.97 (s, 3H), 7.80 (dd, J=8.0, 1.6 Hz, 1H), 7.66 (dd, J=7.7, 1.6 Hz, 1H), 7.53 (dd, J=7.9 Hz, 1H), 3.82-3.68 (m, 2H), 3.29-3.19 (m, 2H), 2.00-1.88 (m, 2H), 1.88-1.78 (m, 2H), 1.40 (s, 3H).

Example 3: 6-(4-amino-4-methylpiperidin-1-yl)-3-(2,3-dichlorophenyl)-1H-pyrazolo[3,4-b]pyrazin-5-ol

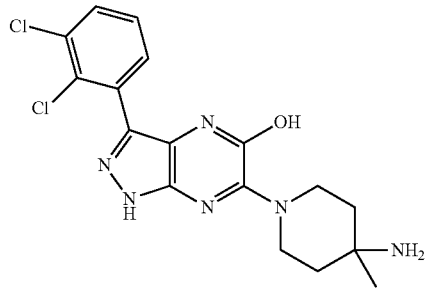 [SMILES: CC1(N)CCN(c2nc3[nH]nc(-c4cccc(Cl)c4Cl)c3nc2C#N)CC1]

6-(4-Amino-4-methylpiperidin-1-yl)-3-(2,3-dichlorophenyl)-1H-pyrazolo[3,4-b]pyrazin-5-ol The title compound (5 mg, 47%) was isolated as a yellow amorphous material from the reaction mixture of Example 2. MS (ES+) C$_{17}$H$_{19}$Cl$_2$N$_6$O requires: 392, found: 393 [M+H]$^+$. $^1$H NMR (500 MHz, DMSO-d$_6$) δ 11.90 (s, 1H), 7.97 (s, 3H), 7.71 (dd, J=7.5, 2.1 Hz, 1H), 7.51-7.37 (m, 2H), 4.42-4.28 (m, 2H), 3.48-3.37 (m, 2H), 1.88-1.79 (m, 2H), 1.78-1.70 (m, 2H), 1.38 (s, 3H).

Example 4: 6-(4-amino-4-methylpiperidin-1-yl)-3-(2,3-dichlorophenyl)-1H-pyrazolo[3,4-b]pyrazine-5-carbonitrile

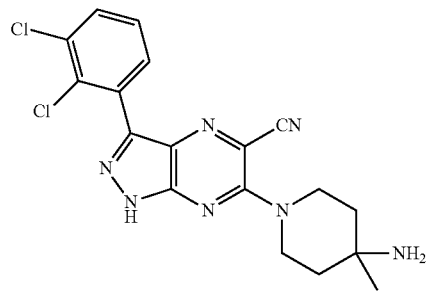

Scheme 2

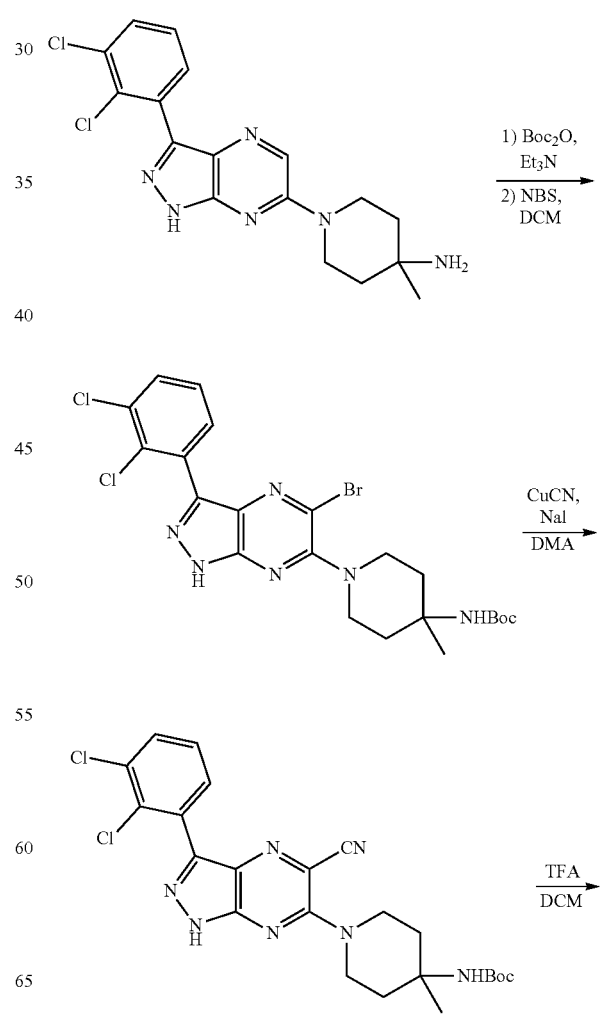

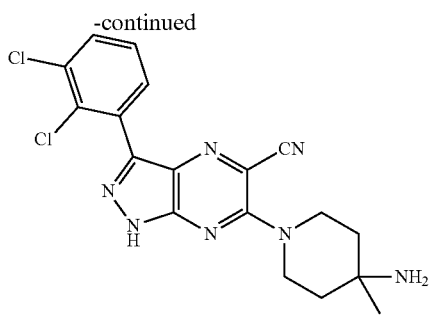

tert-Butyl (1-(3-(2,3-dichlorophenyl)-1H-pyrazolo[3,4-b]pyrazin-6-yl)-4-methylpiperidin-4-yl)carbamate To a suspension of 1-(3-(2,3-dichlorophenyl)-1H-pyrazolo[3,4-b]pyrazin-6-yl)-4-methylpiperidin-4-amine (150 mg, 0.398 mmol) in DMF (2.0 mL) were added triethylamine (222 µl, 1.59 mmol) and Boc20 (231 µl, 0.994 mmol) and the resulting mixture was stirred at 40° C. for 12 h. The volatiles were removed under reduced pressure. The residue was adsorbed onto silica gel and purified via flash chromatography (0-100% EtOAc in hexanes) to give the title compound (159 mg, 84%) as a yellow amorphous material. MS (ES+) $C_{22}H_{26}Cl_2N_6O_2$ requires: 476 found: 477 [M+H]$^+$.

tert-Butyl (1-(5-bromo-3-(2,3-dichlorophenyl)-1H-pyrazolo[3,4-b]pyrazin-6-yl)-4-methylpiperidin-4-yl)carbamate To a solution of tert-butyl (1-(3-(2,3-dichlorophenyl)-1H-pyrazolo[3,4-b]pyrazin-6-yl)-4-methylpiperidin-4-yl)carbamate (50 mg, 0.11 mmol) in DCM (1.0 mL) at 0° C. was added NBS (28.0 mg, 0.157 mmol) and the resulting mixture was allowed to warm to RT over 1 h. The volatiles were removed under reduced pressure. The residue was adsorbed onto silica gel and purified via flash chromatography (0-100% EtOAc in hexanes) to give the title compound (48 mg, 83%) as an orange amorphous material. MS (ES+) $C_{22}H_{25}BrCl_2N_6O_2$ requires: 554 found: 555 [M+H]$^+$.

tert-Butyl (1-(5-cyano-3-(2,3-dichlorophenyl)-1H-pyrazolo[3,4-b]pyrazin-6-yl)-4-methylpiperidin-4-yl)carbamate A suspension of tert-butyl (1-(5-bromo-3-(2,3-dichlorophenyl)-1H-pyrazolo[3,4-b]pyrazin-6-yl)-4-methylpiperidin-4-yl)carbamate (43 mg, 0.077 mmol), copper(I) cyanide (9.0 mg, 0.10 mmol) and sodium iodide (15 mg, 0.10 mmol) in DMA (773 µl) was degassed with $N_2$ for 2 min. The reaction mixture was heated to 150° C. and stirred for 1 h. The volatiles were removed under reduced pressure. The residue was adsorbed onto silica gel and purified via flash chromatography (10-100% EtOAc in hexanes) to give the title compound (30 mg, 77%) as a yellow solid. MS (ES+) $C_{23}H_{25}Cl_2N_7O_2$ requires: 501 found: 502 [M+H]$^+$.

6-(4-amino-4-methylpiperidin-1-yl)-3-(2,3-dichlorophenyl)-1H-pyrazolo[3,4-b]pyrazine-5-carbonitrile To a suspension of tert-butyl (1-(5-cyano-3-(2,3-dichlorophenyl)-1H-pyrazolo[3,4-b]pyrazin-6-yl)-4-methylpiperidin-4-yl)carbamate (29 mg, 0.058 mmol) in DCM (577 µl) were added trifluoroacetic acid (89 µl, 1.1 mmol) and the resulting mixture was stirred at RT for 1 h. The volatiles were removed under reduced pressure. The residue was adsorbed onto silica gel and purified via flash chromatography (0-10% MeOH in DCM with 0.5% NH$_4$OH) to the title compound (15 mg, 65%) as a yellow solid. MS (ES+) $C_{18}H_{17}Cl_2N_7$ requires: 401 found: 402 [M+H]$^+$. $^1$H NMR (600 MHz, DMSO-d$_6$) δ 7.77 (d, J=8.0 Hz, 1H), 7.69 (d, J=7.7 Hz, 1H), 7.52 (dd, J=7.9 Hz, 1H), 3.73-3.65 (m, 4H), 1.73-1.54 (m, 4H), 1.19 (s, 3H).

Example 5: 1-(3-(2,3-dichlorophenyl)-5-(1H-pyrazol-3-yl)-1H-pyrazolo[3,4-b]pyrazin-6-yl)-4-methylpiperidin-4-amine

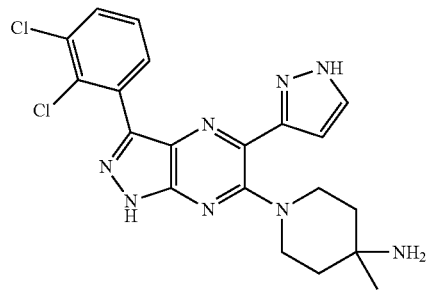 [SMILES: CC1(N)CCN(c2nc3[nH]nc(-c4cccc(Cl)c4Cl)c3nc2-c2cc[nH]n2)CC1]

tert-Butyl 6-(4-((tert-butoxycarbonyl)amino)-4-methylpiperidin-1-yl)-3-(2,3-dichlorophenyl)-5-(1H-pyrazol-3-yl)-1H-pyrazolo[3,4-b]pyrazine-1-carboxylate A solution of tert-butyl 5-bromo-6-(4-((tert-butoxycarbonyl)amino)-4-methylpiperidin-1-yl)-3-(2,3-dichlorophenyl)-1H-pyrazolo[3,4-b]pyrazine-1-carboxylate (25 mg, 0.038 mmol), 3-(4,4,5,5-tetramethyl-1,3,2-dioxaborolan-2-yl)-1H-pyrazole (9.6 mg, 0.050 mmol) and K$_2$CO$_3$ (15.8 mg, 0.114 mmol) in Dioxane (173 µl) and water (17 µl) was degassed with N$_2$ for 30 sec. PdCl$_2$ (dppf)-CH$_2$Cl$_2$ adduct (3.1 mg, 3.8 µmol) was added and the mixture was degassed with N$_2$ for an additional 30 sec. The reaction mixture was irradiated in the microwave for 1 h at 120° C. The reaction mixture was filtered through a Celite plug, washed with DCM, and concentrated to give the crude title compound (24 mg, 100%). MS (ES+) $C_{30}H_{36}Cl_2N_8O_4$ requires: 642, found: 643 [M+H]$^+$.

1-(3-(2,3-Dichlorophenyl)-5-(1H-pyrazol-3-yl)-1H-pyrazolo[3,4-b]pyrazin-6-yl)-4-methylpiperidin-4-amine To a solution of tert-butyl 6-(4-((tert-butoxycarbonyl)amino)-4-methylpiperidin-1-yl)-3-(2,3-dichlorophenyl)-5-(1H-pyrazol-3-yl)-1H-pyrazolo[3,4-b]pyrazine-1-carboxylate (24 mg, 0.038 mmol) in DCM (190 µl) was added TFA (59 µl, 0.76 mmol) and the resulting mixture was stirred at 20° C. for 2 h. The mixture was concentrated and the residue was purified by mass-triggered preparative HPLC (Mobile phase: A=0.1% TFA/H$_2$O, B=0.1% TFA/MeCN; Gradient: B=10-50%; 20 min; Column: C18) to give the title compound (10 mg, 34%) as a pale yellow solid. MS (ES+) $C_{20}H_{20}Cl_2N_8 \cdot 3C_2HF_3O_2$ requires: 442, found: 443 [M+H]$^+$. $^1$H NMR (600 MHz, Methanol-d$_4$) δ 7.72 (d, J=2.1 Hz, 1H), 7.66 (t, J=7.6 Hz, 2H), 7.42 (t, J=7.6 Hz, 1H), 6.89 (d, J=2.1

Hz, 1H), 3.62-3.55 (m, 2H), 3.21 (dd, J=13.4, 9.7 Hz, 2H), 2.00-1.93 (m, 2H), 1.83 (d, J=13.4 Hz, 2H), 1.46 (s, 3H).

Example 6: 1-(3-(2,3-dichlorophenyl)-5-methoxy-1H-pyrazolo[3,4-b]pyrazin-6-yl)-4-methylpiperidin-4-amine bis(2,2,2-trifluoroacetate)

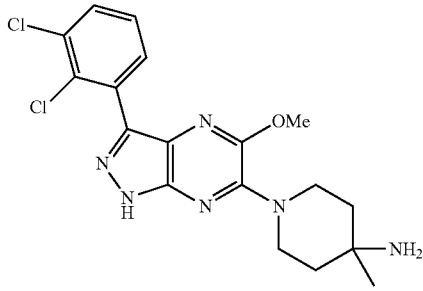 [SMILES: COc1nc2c(-c3cccc(Cl)c3Cl)n[nH]c2nc1N1CCC(C)(N)CC1]

To a solution of tert-butyl 6-(4-((tert-butoxycarbonyl)amino)-4-methylpiperidin-1-yl)-5-chloro-3-(2,3-dichlorophenyl)-1H-pyrazolo[3,4-b]pyrazine-1-carboxylate (20 mg, 0.033 mmol) in MeOH (163 μl) was added aq. HCl (327 μl, 0.327 mmol, 1M) and the resulting mixture was stirred at 20° C. for 4 h. The mixture was concentrated and the residue was purified by mass-triggered preparative HPLC (Mobile phase: A=0.1% TFA/H$_2$O, B=0.1% TFA/MeCN; Gradient: B=20-60%; 20 min; Column: C18) to give the title compound (7.5 mg, 29%) as a white solid. MS (ES+) C$_{18}$H$_{20}$Cl$_2$N$_6$O.2C$_2$HF$_3$O$_2$ requires: 406, found: 407 [M+H]$^+$. $^1$H NMR (600 MHz, Methanol-d$_4$) δ 7.70-7.58 (m, 2H), 7.46-7.38 (m, 1H), 4.21-4.17 (m, 2H), 4.00 (s, 3H), 3.45-3.42 (m, 2H), 2.11-2.03 (m, 2H), 2.02-1.88 (m, 2H), 1.52 (s, 3H).

Example 7: (6-(4-amino-4-methylpiperidin-1-yl)-3-(2,3-dichlorophenyl)-1H-pyrazolo[3,4-b]pyrazin-5-yl)methanol

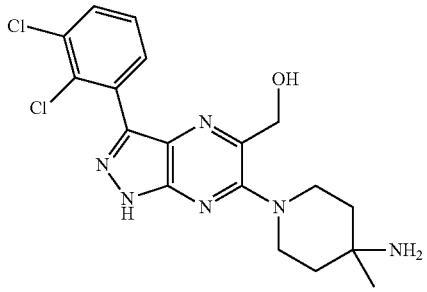 [SMILES: CC1(N)CCN(c2nc3[nH]nc(-c4cccc(Cl)c4Cl)c3nc2CO)CC1]

Scheme 3

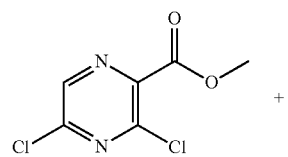

-continued

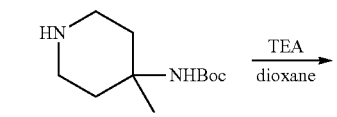

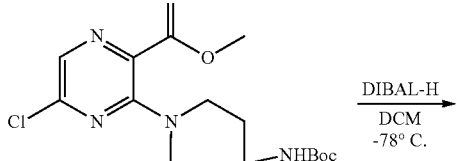

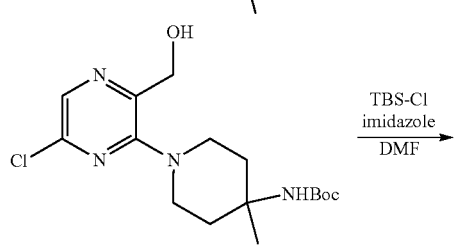

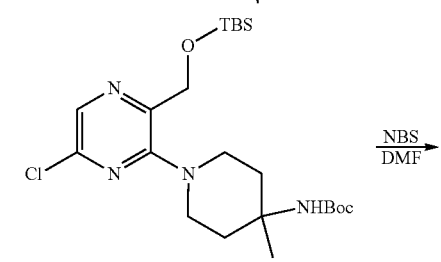

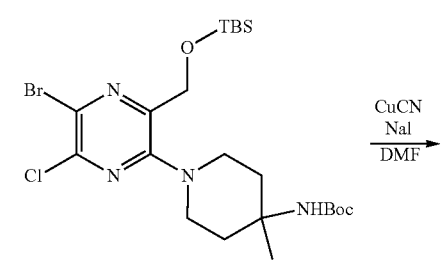

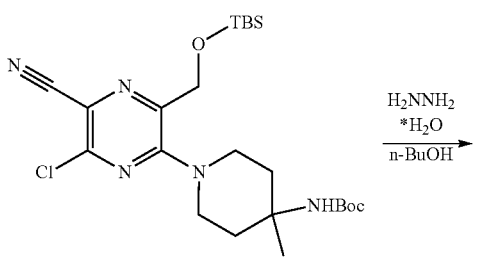

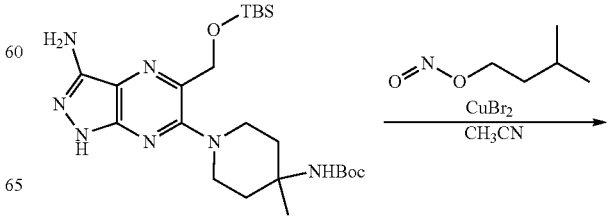

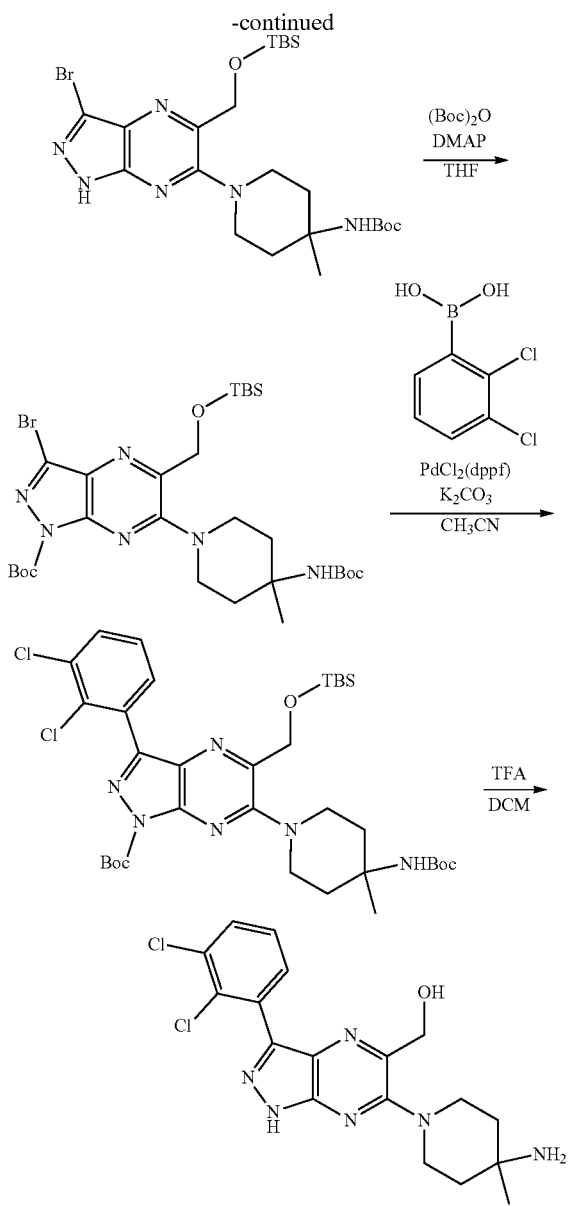

Methyl 3-(4-((tert-butoxycarbonyl)amino)-4-methylpiperidin-1-yl)-5-chloropyrazine-2-carboxylate To a solution of methyl 3,5-dichloropyrazine-2-carboxylate (100 mg, 0.483 mmol) in dioxane (1.93 mL) were added tert-butyl (4-methylpiperidin-4-yl)carbamate (109 mg, 0.507 mmol) and TEA (0.141 mL, 1.01 mmol) and the resulting mixture was stirred at 24° C. for 18 h. H$_2$O (20 mL) was added, and the layers were separated. The aqueous phase was extracted with EtOAc (3×20 mL), the combined organic layers were washed with sat NaCl, dried over Na$_2$SO$_4$, filtered and concentrated under reduced pressure. The residue was purified via silica gel chromatography (0-100% EtOAc in hexanes) to give the title compound (120 mg, 64%) as pale yellow solid. MS (ES+) C17H$_{25}$ClN$_4$O$_4$ requires: 384, found: 407 [M+Na]$^+$. $^1$H NMR (500 MHz, Chloroform-d) δ 7.88 (s, 1H), 4.40 (s, 1H), 3.96 (s, 3H), 3.71-3.57 (m, 2H), 3.46-3.27 (m, 2H), 2.19-2.04 (m, 2H), 1.74-1.62 (m, 2H), 1.54-1.34 (m, 12H). Also isolated regioisomer methyl 5-(4-((tert-butoxycarbonyl)amino)-4-methylpiperidin-1-yl)-3-chloropyrazine-2-carboxylate (60 mg, 32%) as a pale yellow solid. $^1$H NMR (500 MHz, Chloroform-d) δ 8.03 (s, 1H), 4.41 (s, 1H), 4.06-3.96 (m, 2H), 3.95 (s, 3H), 3.53-3.39 (m, 2H), 2.26-2.12 (m, 2H), 1.72-1.57 (m, 2H), 1.50-1.37 (m, 12H).

Tert-butyl (1-(6-chloro-3-(hydroxymethyl)pyrazin-2-yl)-4-methylpiperidin-4-yl)carbamate To a cooled −78° C. solution of methyl 3-(4-((tert-butoxycarbonyl)amino)-4-methylpiperidin-1-yl)-5-chloropyrazine-2-carboxylate (150 mg, 0.390 mmol) in DCM (4.0 mL) was added DIBAL-H (1.55 mL, 1.55 mmol, 1.0M). The resulting mixture was stirred at −78° C. for 30 min. The mixture was then warmed to 0° C. for 30 min and cooled back down to −78° C. Na$_2$SO$_4$ decahydrate was added to the mixture at −78° C. and allowed to warm to RT where it remained for 2 h. The reaction mixture was diluted with DCM (10 mL), filtered through Celite, and the filtrate was concentrated under reduced pressure. The residue was purified via silica gel chromatography (0-50% EtOAc in hexanes) to give the title compound (80 mg, 57%) as an off-white solid. MS (ES+) C16H$_{25}$ClN$_4$O$_3$ requires: 356, found: 357 [M+H]$^+$. $^1$H NMR (600 MHz, Chloroform-d) δ 8.05 (s, 1H), 4.64 (s, 2H), 4.39 (s, 1H), 3.73 (s, 1H), 3.40-3.28 (m, 2H), 3.25-3.12 (m, 2H), 2.19-2.05 (m, 2H), 1.79-1.68 (m, 2H), 1.49-1.36 (m, 12H).

Tert-butyl (1-(3-(((tert-butyldimethylsilyl)oxy)methyl)-6-chloropyrazin-2-yl)-4-methylpiperidin-4-yl)carbamate To a solution of tert-butyl (1-(6-chloro-3-(hydroxymethyl)pyrazin-2-yl)-4-methylpiperidin-4-yl)carbamate (80 mg, 0.22 mmol) in DMF (1.12 mL) were added TBS-Cl (40.5 mg, 0.269 mmol) and imidazole (38 mg, 0.56 mmol) and the resulting mixture was stirred at 25° C. for 12 h. The reaction mixture was diluted with EtOAc (10 mL), H$_2$O (10 mL) was added, and the layers were separated. The aqueous phase was extracted with EtOAc (3×10 mL), the combined organic layers were washed with sat NaCl, dried over Na$_2$SO$_4$, filtered and concentrated under reduced pressure. The residue was purified via silica gel chromatography (0-20% EtOAc in hexanes) to give the title compound (92 mg, 87%) as a colorless liquid. MS (ES+) C$_{22}$H$_{39}$ClN$_4$O$_3$Si requires: 470, found: 471 [M+H]$^+$. $^1$H NMR (600 MHz, Chloroform-d) δ 8.02 (s, 1H), 4.68 (s, 2H), 4.41 (s, 1H), 3.63-3.54 (m, 2H), 3.34-3.21 (m, 2H), 2.16-2.05 (m, 2H), 1.75-1.66 (m, 2H), 1.47-1.37 (m, 12H), 0.88 (s, 9H), 0.10 (d, J=1.0 Hz, 6H).

Tert-butyl (1-(5-bromo-3-(((tert-butyldimethylsilyl)oxy)methyl)-6-chloropyrazin-2-yl)-4-methylpiperidin-4-yl)carbamate To a cooled 0° C. solution of tert-butyl (1-(3-(((tert-butyldimethylsilyl)oxy)methyl)-6-chloropyrazin-2-yl)-4-methylpiperidin-4-yl)carbamate (172 mg, 0.365 mmol) in DMF (3651 µl) was added NBS (97 mg, 0.548 mmol). The resulting mixture was stirred at 25° C. for 2 h. sat NaHCO$_3$ (5 mL)/sat. Na$_2$S$_2$O$_4$ (5 mL) were added and allowed to stir for 30 min. The layers were separated, the aqueous phase was extracted with EtOAc (3×10 mL), the combined organic layers were washed with sat NaCl, dried over Na$_2$SO$_4$, filtered and concentrated under reduced pressure. The residue was purified via silica gel chromatography (0-15%

Tert-butyl (1-(3-(((tert-butyldimethylsilyl)oxy) methyl)-6-chloro-5-cyanopyrazin-2-yl)-4-methylpiperidin-4-yl)carbamate To a solution of tert-butyl (1-(5-bromo-3-(((tert-butyldimethylsilyl)oxy)methyl)-6-chloropyrazin-2-yl)-4-methylpiperidin-4-yl)carbamate (20 mg, 0.036 mmol) in DMF (182 µl) were added copper(I) cyanide (3.6 mg, 0.040 mmol) and sodium iodide (6.0 mg, 0.040 mmol) and the resulting mixture was stirred at 150° C. for 3 h. The reaction mixture was allowed to cool to RT, filtered through Celite, and the filtrate was concentrated under reduced pressure. The residue was diluted with EtOAc (5 mL), water (5 mL) was added, and the layers were separated. The aqueous phase was extracted with EtOAc (3×5 mL), the combined organic layers were washed with sat. NaHCO$_3$(3×5 mL), brine, dried over Na$_2$SO$_4$, filtered and concentrated under reduced pressure. The residue was purified via silica gel chromatography (0-100% EtOAc in hexanes) to give the title compound (12 mg, 66%) as a yellow liquid. MS (ES+) C$_{23}$H$_{38}$ClN$_5$O$_3$Si requires: 495, found: 496, 498 [M+H]$^+$. $^1$H NMR (600 MHz, Chloroform-d) δ 4.67 (s, 2H), 4.41 (s, 1H), 4.10-4.03 (m, 2H), 3.58-3.48 (m, 2H), 2.19-2.07 (m, 2H), 1.70-1.62 (m, 2H), 1.48-1.38 (m, 12H), 0.87 (s, 9H), 0.08 (s, 6H).

Tert-butyl (1-(3-amino-5-(((tert-butyldimethylsilyl) oxy)methyl)-1H-pyrazolo[3,4-b]pyrazin-6-yl)-4-methylpiperidin-4-yl)carbamate To a solution of tert-butyl (1-(3-(((tert-butyldimethylsilyl) oxy)methyl)-6-chloro-5-cyanopyrazin-2-yl)-4-methylpiperidin-4-yl)carbamate (12 mg, 0.024 mmol) in butan-1-ol (242 µl) was added hydrazine hydrate (2.1 µl, 0.054 mmol) and the resulting mixture was stirred at 105° C. for 6 h. The volatiles were removed under reduced pressure and the residue was purified via silica gel chromatography (0-10% MeOH in DCM) to give the title compound (8.0 mg, 67%) as a yellow solid. MS (ES+) C$_{23}$H$_{41}$N$_7$O$_3$Si requires: 491, found: 492 [M+H]$^+$. $^1$H NMR (600 MHz, Chloroform-d) δ 9.57 (s, 1H), 4.79 (s, 2H), 4.54 (s, 1H), 4.39 (s, 2H), 3.65-3.47 (m, 2H), 3.38-3.22 (m, 2H), 2.21-2.07 (m, 2H), 1.82-1.72 (m, 2H), 1.44 (s, 12H), 0.90 (s, 9H), 0.12 (s, 6H).

Tert-butyl (1-(3-bromo-5-(((tert-butyldimethylsilyl) oxy)methyl)-1H-pyrazolo[3,4-b]pyrazin-6-yl)-4-methylpiperidin-4-yl)carbamate To a cooled 0° C. solution of tert-butyl (1-(3-amino-5-(((tert-butyldimethylsilyl)oxy)methyl)-1H-pyrazolo[3,4-b]pyrazin-6-yl)-4-methylpiperidin-4-yl)carbamate (8.0 mg, 0.016 mmol) and copper(II) bromide (4.0 mg, 0.018 mmol) in acetonitrile (163 µl) was added isopentyl nitrite (5.1 mg, 0.044 mmol). The resulting mixture was stirred at 25° C. for 18 h in the absence of light. Water (1 mL) was added, and the layers were separated. The aqueous phase was extracted with EtOAc (3×3 mL), the combined organic layers were washed with sat. NaCl, dried over Na$_2$SO$_4$, filtered and concentrated under reduced pressure. The residue was purified via silica gel chromatography (0-50% EtOAc in hexanes) to give the title compound (4.0 mg, 44%) as a yellow liquid. MS (ES+) C$_{23}$H$_{39}$BrN$_6$O$_3$Si requires: 554, found: 555, 557 [M+H]$^+$. $^1$H NMR (600 MHz, Chloroform-d) δ 10.00 (s, 1H), 4.43 (s, 2H), 3.76-3.66 (m, 2H), 3.45-3.30 (m, 2H), 2.20-2.07 (m, 2H), 1.80-1.71 (m, 2H), 1.48-1.36 (m, 12H), 0.97-0.83 (m, 9H), 0.15 (s, 6H).

Tert-butyl 3-bromo-6-(4-((tert-butoxycarbonyl) amino)-4-methylpiperidin-1-yl)-5-(((tert-butyldimethylsilyl)oxy)methyl)-1H-pyrazolo[3,4-b]pyrazine-1-carboxylate To a solution of tert-butyl (1-(3-bromo-5-(((tert-butyldimethylsilyl)oxy)methyl)-1H-pyrazolo[3,4-b]pyrazin-6-yl)-4-methylpiperidin-4-yl)carbamate (26 mg, 0.047 mmol) in THF (468 µl) were added Boc$_2$O (13 µl, 0.056 mmol) and DMAP (6.8 mg, 0.056 mmol) and the resulting mixture was stirred at 25° C. for 3 h. The reaction mixture was diluted with EtOAc (10 mL) and washed with water (10 mL). The layers were separated, and the organic layer was washed with sat. NaCl (10 mL), dried over Na$_2$SO$_4$, filtered and concentrated under reduced pressure. The residue was purified via silica gel chromatography (0-20% EtOAc in hexanes) to give the title compound (26 mg, 85%) as a pale yellow solid. MS (ES+) C$_{28}$H$_{47}$BrN$_6$O$_5$Si requires: 654, found: 655 [M+H]$^+$.

Tert-butyl 6-(4-((tert-butoxycarbonyl)amino)-4-methylpiperidin-1-yl)-5-(((tert-butyldimethylsilyl) oxy)methyl)-3-(2,3-dichlorophenyl)-1H-pyrazolo[3, 4-b]pyrazine-1-carboxylate A solution of tert-butyl 3-bromo-6-(4-((tert-butoxycarbonyl)amino)-4-methylpiperidin-1-yl)-5-(((tert-butyldimethylsilyl)oxy)methyl)-1H-pyrazolo[3,4-b]pyrazine-1-carboxylate (26 mg, 0.040 mmol), (2,3-dichlorophenyl)boronic acid (9.8 mg, 0.052 mmol) and K$_2$CO$_3$ (22 mg, 0.16 mmol) in acetonitrile (397 µl) was degassed with N$_2$ for 2 min. PdCl$_2$(dppf)-CH$_2$Cl$_2$ adduct (6.5 mg, 7.9 µmol) was added and the mixture was degassed with N$_2$ for an additional 1 min. The reaction mixture was heated to 100° C. and stirred for 6 h. The reaction mixture was allowed to cool to room temperature, filtered through Celite, and the filtrate was concentrated under reduced pressure. The residue was purified via silica gel chromatography (0-50% EtOAc in hexanes) to give the title compound (8 mg, 28%) as a pale yellow liquid. MS (ES+) C$_{34}$H$_{50}$Cl$_2$N$_6$O$_5$Si requires: 720, found: 721 [M+H]$^+$. $^1$H NMR (600 MHz, Chloroform-d) δ 7.65 (d, J=7.7 Hz, 1H), 7.56 (d, J=8.0 Hz, 1H), 7.30 (t, J=8.1 Hz, 1H), 4.79 (s, 2H), 4.46 (s, 1H), 3.86-3.78 (m, 2H), 3.49-3.38 (m, 2H), 2.18-2.11 (m, 2H), 1.81-1.75 (m, 2H), 1.72 (s, 9H), 1.45-1.42 (m, 12H), 0.86 (s, 9H), 0.06 (s, 6H).

(6-(4-Amino-4-methylpiperidin-1-yl)-3-(2,3-dichlorophenyl)-1H-pyrazolo[3,4-b]pyrazin-5-yl)methanol To a cooled 0° C. solution of tert-butyl 6-(4-((tert-butoxycarbonyl)amino)-4-methylpiperidin-1-yl)-5-(((tert-butyl dim ethyl silyl)oxy)methyl)-3-(2,3-dichlorophenyl)-1H-pyrazolo[3,4-b]pyrazine-1-carboxylate (15 mg, 0.021 mmol) in DCM (208 µl) was added TFA (21 µl, 0.27 mmol). The resulting mixture was stirred at 25° C. for 18 h. The residue was purified via silica gel chromatography (0-20% MeOH in DCM) to give the title compound (2 mg, 24%) as a white solid. MS (ES+) C$_{18}$H$_{20}$Cl$_2$N$_6$O requires: 406, found: 390 [M-OH]$^+$. $^1$H NMR (600 MHz, Methanol-d$_4$) δ 7.69-7.65 (m, 1H), 7.64 (d, J=7.6 Hz, 1H), 7.46-7.40 (m, 1H), 4.76 (d, J=1.7 Hz, 2H), 3.82-3.75 (m, 2H), 3.41-3.36 (m, 2H), 2.09-2.02 (m, 2H), 1.99-1.91 (m, 2H), 1.52 (s, 3H).

91

Example 8: 6-(4-amino-4-methylpiperidin-1-yl)-3-(2,3-dichlorophenyl)-1H-pyrazolo[3,4-b]pyrazine-5-carboxamide

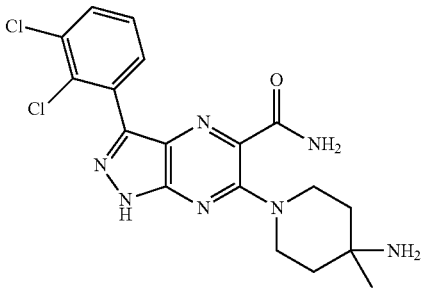 [SMILES: CC1(N)CCN(c2nc3[nH]nc(-c4cccc(Cl)c4Cl)c3nc2C(N)=O)CC1]

Scheme 4

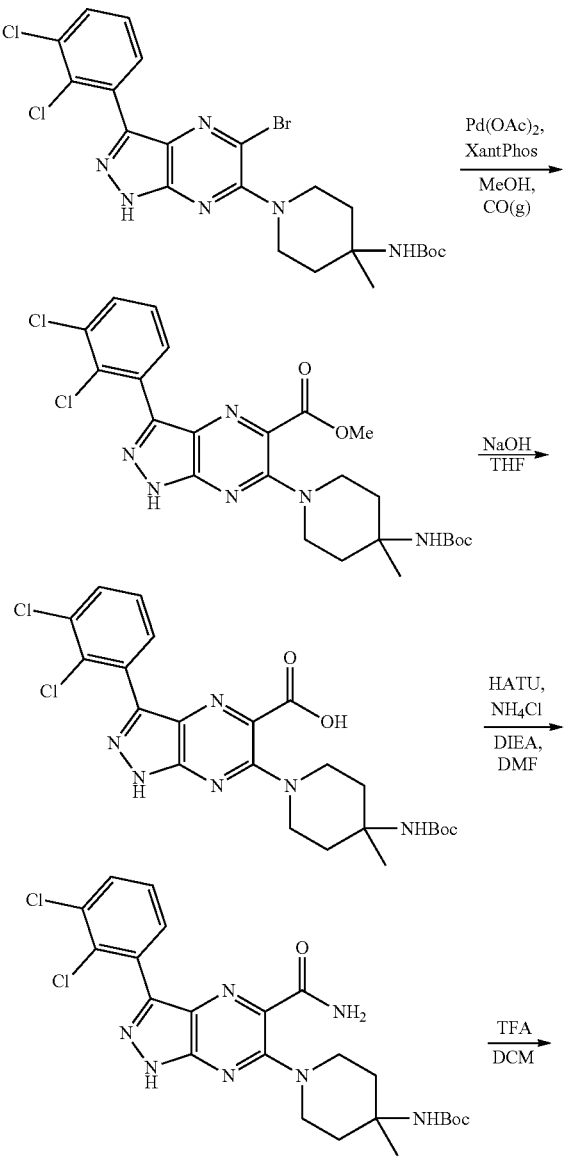

92

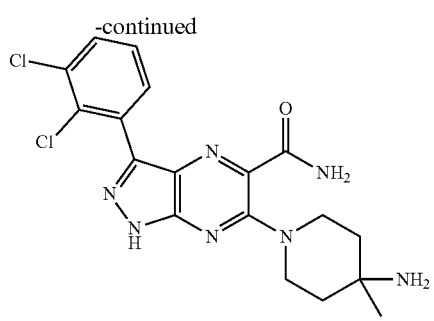

Methyl 6-(4-(tert-butoxycarbonylamino)-4-methylpiperidin-1-yl)-3-(2,3-dichlorophenyl)-1H-pyrazolo[3,4-b]pyrazine-5-carboxylate To a mixture of tert-butyl (1-(5-bromo-3-(2,3-dichlorophenyl)-1H-pyrazolo[3,4-b]pyrazin-6-yl)-4-methylpiperidin-4-yl)carbamate (300 mg, 0.54 mmol) in MeOH (20 mL) was added Pd(OAc)$_2$ (12 mg, 0.054 mmol), Xantphos (31 mg, 0.054 mmol), and TEA (0.5 mL). The mixture was flushed with carbon monoxide and refluxed with a carbon monoxide balloon for 15 h. The volatiles were removed under reduced pressure. The residue was adsorbed onto silica gel and purified via flash chromatography (10-100% EtOAc in petroleum ether) to give the title compound (300 mg, >100%). as a brown solid. MS (ES+) $C_{24}H_{28}Cl_2N_6O_4$ requires: 534, found: 535 [M+H]$^+$.

6-(4-(tert-Butoxycarbonylamino)-4-methylpiperidin-1-yl)-3-(2,3-dichlorophenyl)-1H-pyrazolo[3,4-b]pyrazine-5-carboxylic acid A mixture of methyl 6-(4-(tert-butoxycarbonylamino)-4-methylpiperidin-1-yl)-3-(2,3-dichlorophenyl)-1H-pyrazolo[3,4-b]pyrazine-5-carboxylate (190 mg, 0.35 mmol) and aq. NaOH (5 mL, 2M) in THF (10 mL) was heated at reflux for 48 h. The volatiles were removed under reduced pressure. The residue was diluted with EtOAc and sat. citric acid to adjust the pH to <5. The mixture was extracted with EtOAc (5×20 mL), dried over MgSO$_4$, filtered and concentrated. The residue was purified via silica gel chromatography (0-10% MeOH in DCM) to give the title compound (50 mg, 27%) as a brown solid. MS (ES+) $C_{23}H_{26}Cl_2N_6O_4$ requires: 520, found: 521 [M+H]$^+$.

tert-Butyl 1-(5-carbamoyl-3-(2,3-dichlorophenyl)-1H-pyrazolo[3,4-b]pyrazin-6-yl)-4-methylpiperidin-4-ylcarbamate To a mixture of 6-(4-(tert-butoxycarbonylamino)-4-methylpiperidin-1-yl)-3-(2,3-dichlorophenyl)-1H-pyrazolo[3,4-b]pyrazine-5-carboxylic acid (20 mg, 0.038 mmol) in DMF (2 mL) was added HATU (22 mg, 0.058 mmol) and the resulting mixture was stirred for 10 min before NH$_4$Cl (20 mg, 0.37 mmol) and DIPEA (0.2 mL) was added. The mixture was stirred for 1 h at rt. The mixture was diluted with water (20 mL), extracted with EtOAc (20 mL×3), washed with brine (20 mL), concentrated and used for the next step directly. MS (ES+) $C_{23}H_{27}Cl_2N_7O_3$ requires: 519, found: 520 [M+H]$^+$.

6-(4-Amino-4-methylpiperidin-1-yl)-3-(2,3-dichlorophenyl)-1H-pyrazolo[3,4-b]pyrazine-5-carboxamide To a solution of tert-butyl 1-(5-carbamoyl-3-(2,3-dichlorophenyl)-1H-pyrazolo[3,4-b]pyrazin-6-yl)-4-methylpiperidin-4-ylcarbamate (20 mg, 0.038 mmol) in DCM (5 mL) was added TFA (1 mL) was stirred at rt for 1 h. The volatiles were removed under reduced pressure. The residue was purified by preparative HPLC (Mobile phase: A=0.01% TFA/H$_2$O, B=0.01% TFA/MeCN; Gradient: B=10-90%; 12 min; Column: C18) to give the title compound (3.9 mg, 24%, TFA salt) as a light yellow solid. MS (ES+) C$_{18}$H$_{19}$Cl$_2$N$_7$O.C$_2$HF$_3$O$_2$ requires: 419, found: 420 [M+H]$^+$. $^1$H NMR (500 MHz, 600 MHz, Methanol-d$_4$) δ 7.68 (td, J=7.7, 1.5 Hz, 2H), 7.46 (t, J=7.9 Hz, 1H), 3.95 (d, J=14.4 Hz, 2H), 3.45-3.36 (m, 2H), 2.02 (t, J=9.6 Hz, 2H), 1.92 (d, J=13.3 Hz, 2H), 1.52 (s, 3H).

Example 9: 6-(4-amino-4-methylpiperidin-1-yl)-3-(2,3-dichlorophenyl)-1H-pyrazolo[3,4-b]pyrazine-5-carbaldehyde

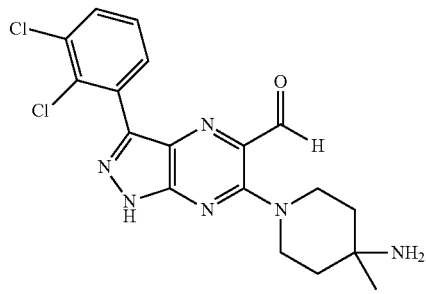 [SMILES: CC1(N)CCN(c2nc3[nH]nc(-c4cccc(Cl)c4Cl)c3nc2C=O)CC1]

Scheme 5

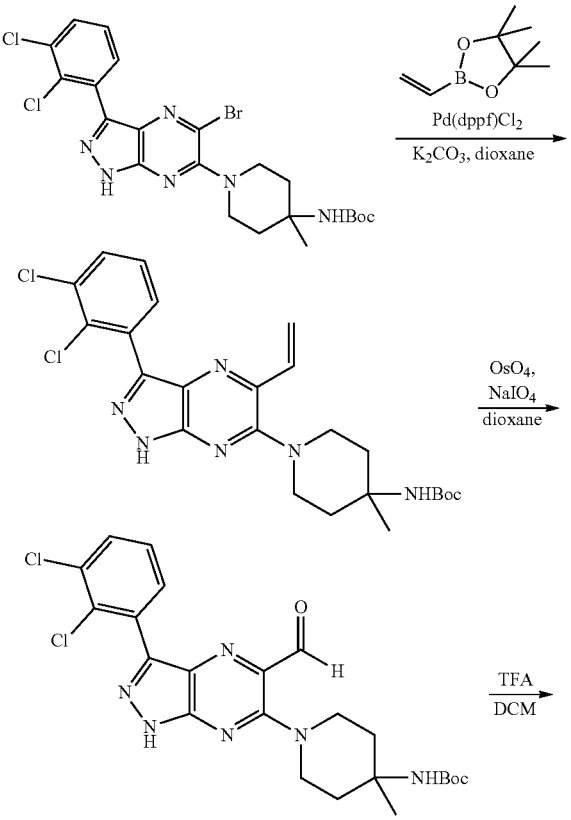

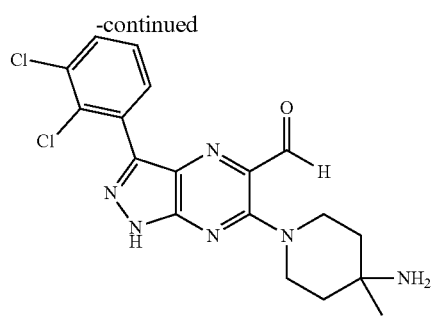

tert-Butyl (1-(3-(2,3-dichlorophenyl)-5-vinyl-1H-pyrazolo[3,4-b]pyrazin-6-yl)-4-methylpiperidin-4-yl)carbamate A microwave vial was charged with tert-butyl (1-(5-bromo-3-(2,3-dichlorophenyl)-1H-pyrazolo[3,4-b]pyrazin-6-yl)-4-methylpiperidin-4-yl)carbamate (200 mg, 0.360 mmol), 4,4,5,5-tetramethyl-2-vinyl-1,3,2-dioxaborolane (72.0 mg, 0.467 mmol), K$_2$CO$_3$ (149 mg, 1.08 mmol) and dioxane (3.3 mL). The reaction mixture was degassed with N2 for 1 min. PdCl$_2$(dppf)-CH$_2$Cl$_2$ adduct (29 mg, 0.036 mmol) was added and the mixture was degassed with N$_2$ for an additional 1 min. The vial was sealed and the reaction mixture was heated to 120° C. in the microwave reactor for 1 h. The volatiles were removed under reduced pressure. The residue was adsorbed onto silica gel and purified via flash chromatography (10-100% EtOAc in hexanes) to give the title compound (92 mg, 51%) as a yellow solid. MS (ES+) C$_{24}$H$_{28}$Cl$_2$N$_6$O$_2$ requires: 502, found: 503 [M+H]$^+$.

tert-Butyl (1-(3-(2,3-dichlorophenyl)-5-formyl-1H-pyrazolo[3,4-b]pyrazin-6-yl)-4-methylpiperidin-4-yl)carbamate To a solution of tert-butyl (1-(3-(2,3-dichlorophenyl)-5-vinyl-1H-pyrazolo[3,4-b]pyrazin-6-yl)-4-methylpiperidin-4-yl)carbamate (30 mg, 0.060 mmol) in dioxane (447 µl) and Water (149 µl) were added 2,6-lutidine (13.9 µl, 0.119 mmol), sodium periodate (51.0 mg, 0.238 mmol), and osmium tetroxide (9.4 µl, 1.2 µmol, 4% solution in water) and the resulting mixture was stirred at rt for 12 h. The volatiles were removed under reduced pressure. The residue was adsorbed onto silica gel and purified via flash chromatography (10-100% EtOAc in hexanes) to give the title compound (26 mg, 86%) as a pale yellow solid. MS (ES+) C$_{23}$H$_{26}$Cl$_2$N$_6$O$_3$ requires: 504, found: 505 [M+H]$^+$.

6-(4-Amino-4-methylpiperidin-1-yl)-3-(2,3-dichlorophenyl)-1H-pyrazolo[3,4-b]pyrazine-5-carbaldehyde To a solution of tert-butyl (1-(3-(2,3-dichlorophenyl)-5-formyl-1H-pyrazolo[3,4-b]pyrazin-6-yl)-4-methylpiperidin-4-yl)carbamate (25 mg, 0.049 mmol) in DCM (495 µl) was added trifluoroacetic acid (95 µl, 1.2 mmol) and the resulting mixture was stirred at rt for 1 h. The volatiles were removed under reduced pressure. The residue was purified by mass-triggered preparative HPLC (Mobile phase: A=0.1% TFA/H$_2$O, B=0.1% TFA/MeCN; Gradient: B=10-90%; 12 min; Column: C18) to give the title compound (8 mg, 40%, TFA salt) as a yellow solid. MS (ES+) C$_{18}$H$_{18}$Cl$_2$N$_6$O. C$_2$HF$_3$O$_2$ requires: 404, found: 405 [M+H]$^+$. $^1$H NMR (600 MHz, DMSO-d$_6$) δ 14.06 (s, 1H), 9.85 (s, 1H), 7.97 (s, 3H), 7.82 (d, J=8.3 Hz, 1H), 7.74 (d, J=7.6 Hz, 1H), 7.55 (t, J=7.8 Hz, 1H), 3.84-3.72 (m, 2H), 3.35-3.30 (m, 2H), 2.01-1.88 (m, 2H), 1.87-1.73 (m, 2H), 1.40 (s, 3H).

The following examples were synthesized with synthetic methods that were similar to that used for the above Examples, and can generally be made by methods disclosed herein. The Examples may be made as free bases or as salts.

| Example | Name | Structure | Exact Mass | Mass observed | Prepared according to Example |
|---|---|---|---|---|---|
| 10 | 1-(5-chloro-3-(2,3-dichlorophenyl)-1H-pyrazolo[3,4-b]pyrazin-6-yl)-4-methylpiperidin-4-amine | 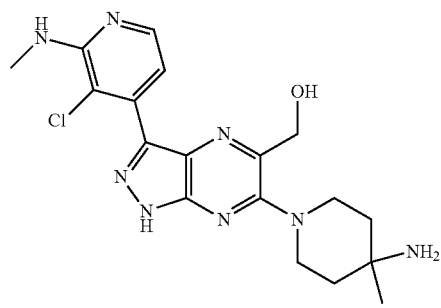 [SMILES: CNc1nccc(-c2n[nH]c3nc(N4CCC(C)(N)CC4)c(CO)nc23)c1Cl] | 410 | 411 | Example 2 |

Example 11: (6-(4-amino-4-methylpiperidin-1-yl)-3-(3-chloro-2-(methylamino)pyridin-4-yl)-1H-pyrazolo[3,4-b]pyrazin-5-yl)methanol

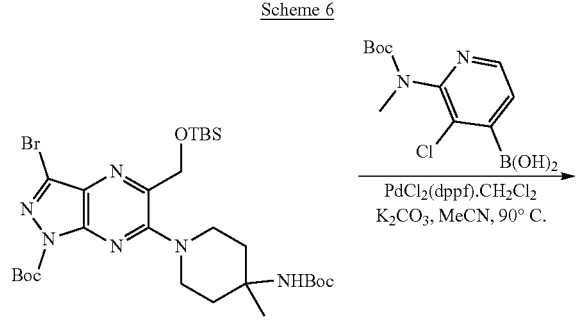

Scheme 6

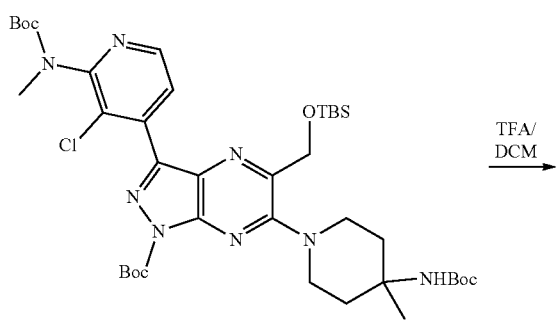

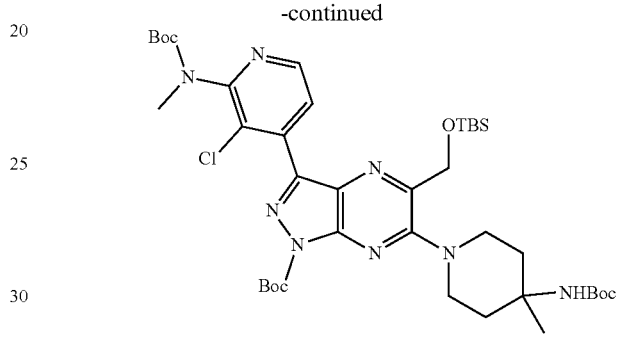

tert-Butyl 3-(2-((tert-butoxycarbonyl)(methyl)amino)-3-chloropyridin-4-yl)-6-(4-((tert-butoxycarbonyl)amino)-4-methylpiperidin-1-yl)-5-(((tert-butyldimethylsilyl)oxy)methyl)-1H-pyrazolo[3,4-b]pyrazine-1-carboxylate To a solution of tert-butyl 3-bromo-6-(4-((tert-butoxycarbonyl)amino)-4-methylpiperidin-1-yl)-5-(((tert-butyldimethylsilyl)oxy)methyl)-1H-pyrazolo[3,4-b]pyrazine-1-carboxylate (50 mg, 0.076 mmol) in MeCN (763 µl) were added (2-((tert-butoxycarbonyl)(methyl)amino)-3-chloropyridin-4-yl)boronic acid (28.4 mg, 0.099 mmol) and $K_2CO_3$ (42.2 mg, 0.305 mmol) and the resulting mixture was degassed with $N_2$ for 2 minutes. $PdCl_2(dppf)$-$CH_2Cl_2$ adduct (12.45 mg, 0.015 mmol) was added and the mixture was degassed with $N_2$ for an additional 1 minute. The reaction mixture was heated to 90° C. and stirred for 6 h. The reaction mixture was allowed to cool to room temperature, filtered through celite, and the filtrate was concentrated under reduced pressure. The residue was purified via silica gel chromatography 0-50% EtOAc in hexanes to give the desired compound (12 mg, 0.015 mmol, 19% yield) as a pale yellow liquid. $^1$H-NMR (600 MHz, $CDCl_3$) 8.48 (d, J=0.01 Hz, 1H), 7.77 (d, J=0.01 Hz, 1H), 4.80 (s, 2H), 3.89 (d(br), J=0.02 Hz, 2H), 3.49 (t(br), J=0.01 Hz, 2H), 3.27 (s, 3H), 2.16 (d(br), J=0.02 Hz, 2H), 1.77 (t(br), J=0.01 Hz, 2H), 1.73 (s, 9H), 1.45 (s, 9H), 1.44 (s, 3H), 1.42 (s, 9H), 0.89 (s, 9H), 0.08 (s, 6H) MS (ES+) $C_{39}H_{61}ClN_8O_7Si$ requires: 816, found: 717 [M+H-100]$^+$

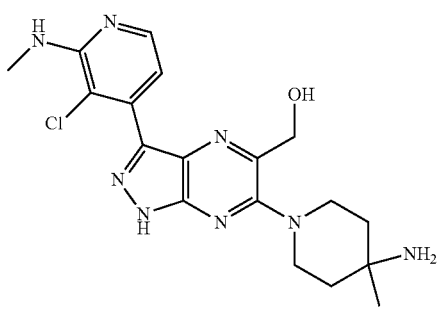 [SMILES: CNc1nccc(-c2n[nH]c3nc(N4CCC(C)(N)CC4)c(CO)nc23)c1Cl]

(6-(4-Amino-4-methylpiperidin-1-yl)-3-(3-chloro-2-(methylamino)pyridin-4-yl)-1H-pyrazolo[3,4-b]pyrazin-5-yl)methanol To a solution of tert-butyl 3-(2-((tert-butoxycarbonyl)(methyl)amino)-3-chloropyridin-4-yl)-6-(4-((tert-butoxycarbonyl)amino)-4-methylpiperidin-1-yl)-5-(((tert-butyldimethylsilyl)oxy)methyl)-1H-pyrazolo[3,4-b]pyrazine-1-carboxylate (12 mg, 0.015 mmol) in DCM (147 µl) was added TFA (29.4 µl, 0.015 mmol) and the resulting mixture was stirred at 25° C. for 18 h. The solvent was evaporated and the residue redissolved in MeOH (300 µL). K$_2$CO$_3$ (4.06 mg, 0.029 mmol) was added and the mixture was stirred for 3 h. The volatiles were removed under reduced pressure. The residue was purified via silica gel chromatography 10% MeOH in DCM with 0.5% NH$_4$OH to give the desired compound (1.5 mg, 3.7 µmol, 25% yield) as a pale yellow solid. $^1$H-NMR (600 MHz, CDCl$_3$) 8.18 (d, J=0.01 Hz, 1H), 7.04 (d, J=0.01 Hz, 1H), 5.32 (d(br), J=0.01, 1H), 4.78 (s, 2H), 3.39 (m, 4H), 3.12 (d, J=0.011 3H), 1.26 (s, 3H) MS (ES+) C$_{18}$H$_{23}$ClN$_8$O requires: 402, found: 403 [M+H]$^+$ Example 12: 1-(6-(4-amino-4-methylpiperidin-1-yl)-3-(2,3-dichlorophenyl)-1H-pyrazolo[3,4-b]pyrazin-5-yl)ethanol

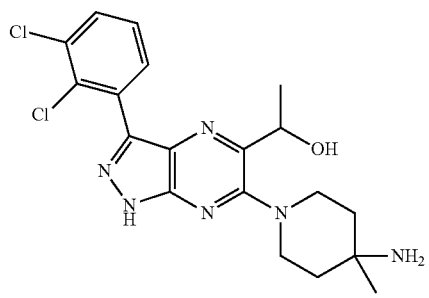 [SMILES: CC(O)c1nc2c(-c3cccc(Cl)c3Cl)n[nH]c2nc1N1CCC(C)(N)CC1]

Scheme 7

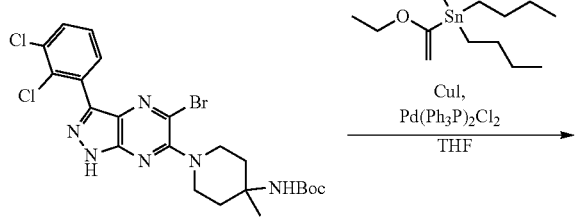

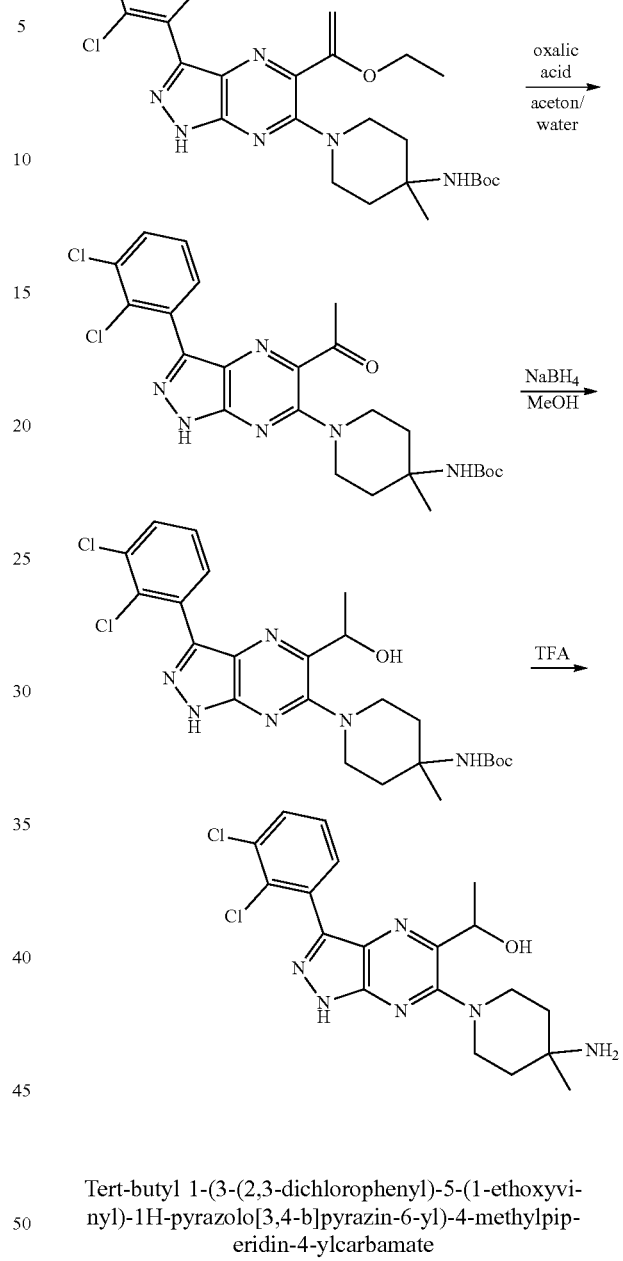

Tert-butyl 1-(3-(2,3-dichlorophenyl)-5-(1-ethoxyvinyl)-1H-pyrazolo[3,4-b]pyrazin-6-yl)-4-methylpiperidin-4-ylcarbamate A mixture of tert-butyl 1-(5-bromo-3-(2,3-dichlorophenyl)-1H-pyrazolo[3,4-b]pyrazin-6-yl)-4-methylpiperidin-4-ylcarbamate (100 mg, 0.148 mmol), tributyl(1-ethoxyvinyl)stannane (80 mg, 0.222 mmol), CuI (2.8 mg, 0.015 mmol), and Pd(Ph$_3$P)$_2$Cl$_2$ (10 mg, 0.015 mmol) in THF (1.5 mL) were flushed with Ar for 2 min. and the resulting mixture was heated to 70° C. for 2 hours. The mixture was cooled to room temperature, concentrated under reduced pressure and purified via silica gel chromatography (10-80% EtOAc in hexanes) to give the title compound as a brown oil (80 mg, 0.146 mmol). MS (ES+) C$_{26}$H$_{32}$Cl$_2$N$_6$O$_3$ requires: 546, found: 547 [M+H]$^+$.

Tert-butyl 1-(5-acetyl-3-(2,3-dichlorophenyl)-1H-pyrazolo[3,4-b]pyrazin-6-yl)-4-methylpiperidin-4-ylcarbamate To a mixture of tert-butyl 1-(3-(2,3-dichlorophenyl)-5-(1-ethoxyvinyl)-1H-pyrazolo[3,4-b]pyrazin-6-yl)-4-methylpiperidin-4-ylcarbamate (50 mg, 0.091 mmol) in acetone (3 mL)/water (1 mL) was added oxalic acid (50 mg, 0.555 mmol) and the mixture was stirred at 25° C. for 1 hour. Brine (25 mL) was added and the mixture extracted with EtOAc (3×25 mL), the organic phases combined, washed with brine, dried over Na$_2$SO$_4$, filtered, and concentrated under reduced pressure to give the title compound crude (50 mg, 0.096 mmol). The resulting mixture was used without further purification. MS (ES+) C24H28Cl2N6O3 requires: 518, found: 519 [M+H]$^+$

Tert-butyl 1-(3-(2,3-dichlorophenyl)-5-(1-hydroxyethyl)-1H-pyrazolo[3,4-b]pyrazin-6-yl)-4-methylpiperidin-4-ylcarbamate To a 0° C. solution of tert-butyl 1-(5-acetyl-3-(2,3-dichlorophenyl)-1H-pyrazolo[3,4-b]pyrazin-6-yl)-4-methylpiperidin-4-ylcarbamate (50 mg, 0.096 mmol) in MeOH (2 ml) was added NaBH$_4$ (20 mg, 0.528 mmol) and the resulting mixture was stirred at 0° C. for 20 min. Brine (25 mL) was added and the mixture extracted with EtOAc (3×25 mL), the organic phases combined, washed with brine, dried over Na$_2$SO$_4$, filtered, and concentrated under reduced pressure to obtain the title compound as a brown oil (50 mg, 0.096 mmol). The resulting mixture was used without further purification. MS (ES+) C24H30Cl2N6O3 requires: 520, found: 521 [M+H]$^+$

1-(6-(4-Amino-4-methylpiperidin-1-yl)-3-(2,3-dichlorophenyl)-1H-pyrazolo[3,4-b]pyrazin-5-yl)ethanol To tert-butyl 1-(3-(2,3-dichlorophenyl)-5-(1-hydroxyethyl)-1H-pyrazolo[3,4-b]pyrazin-6-yl)-4-methylpiperidin-4-ylcarbamate (50 mg, 0.096 mmol) was added TFA (2 ml) and the resulting mixture was stirred at 25° C. for 1 hour. The volatiles were removed under reduced pressure and the residue was purified by preparative HPLC (Mobile phase: A=0.01% TFA/H$_2$O, B=0.01% TFA/MeCN; Gradient: B=10-90%; 12 min; Column: C18) to obtain the title compound as a light yellow solid (20 mg, 0.045 mmol). MS (ES+) C21H27ClN8O requires: 442, found: 443 [M+H]$^+$. $^1$H NMR (500 MHz, MeOD) δ 7.69 (d, J=7.9 Hz, 2H), 7.45 (t, J=7.9 Hz, 1H), 5.20 (q, J=6.3 Hz, 1H), 3.85 (d, J=13.7 Hz, 1H), 3.62 (d, J=13.6 Hz, 1H), 3.46 (ddd, J=13.6, 8.8, 4.5 Hz, 1H), 3.27 (t, J=10.6 Hz, 1H), 2.21-2.08 (m, 1H), 2.05-1.86 (m, 3H), 1.58 (d, J=6.4 Hz, 3H), 1.53 (s, 3H).

Example 13: 6-(4-Amino-4-methylpiperidin-1-yl)-3-(2,3-dichlorophenyl)-N-hydroxy-1H-pyrazolo[3,4-b]pyrazine-5-carboxamide

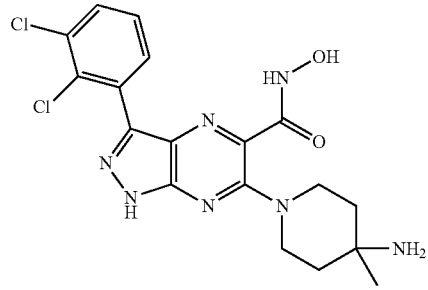 [SMILES: CC1(N)CCN(c2nc3[nH]nc(-c4cccc(Cl)c4Cl)c3nc2C(=O)NO)CC1]

Scheme 8

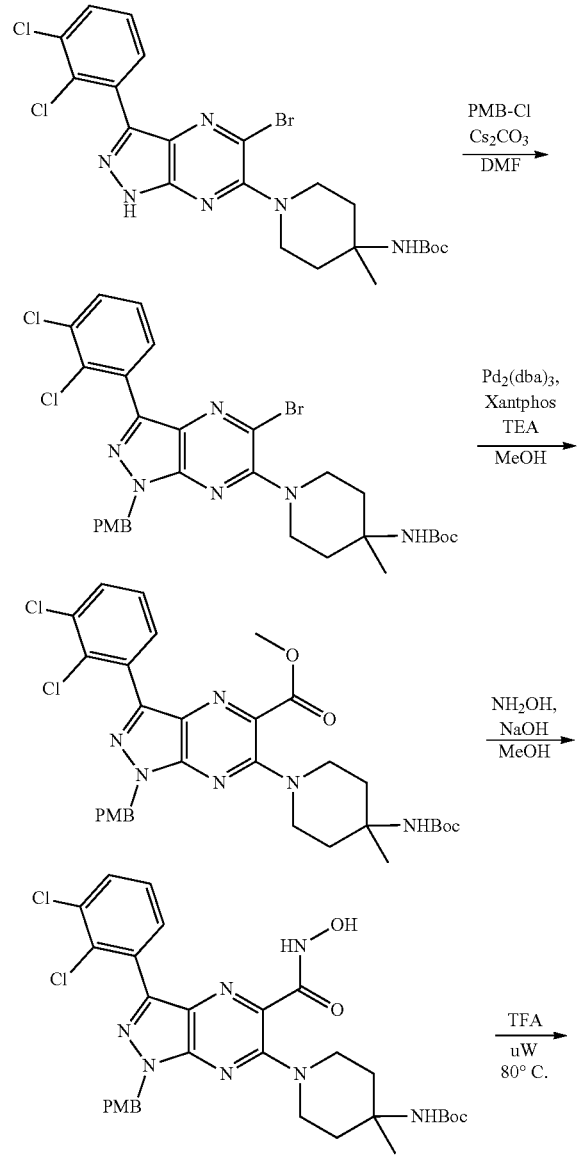

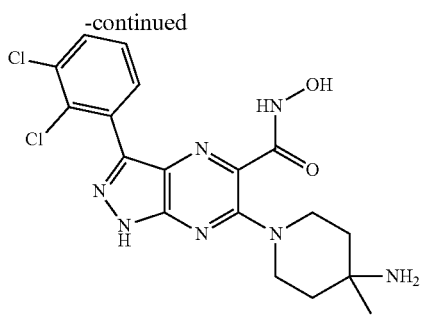

Tert-butyl 1-(5-bromo-3-(2,3-dichlorophenyl)-1-(4-methoxybenzyl)-1H-pyrazolo[3,4-b]pyrazin-6-yl)-4-methylpiperidin-4-ylcarbamate To a solution of tert-butyl 1-(5-bromo-3-(2,3-dichlorophenyl)-1H-pyrazolo[3,4-b]pyrazin-6-yl)-4-methylpiperidin-4-ylcarbamate (800 mg, 1.44 mmol) in DMF (10 mL) were added 1-(chloromethyl)-4-methoxybenzene (337 mg, 2.16 mmol) and $Cs_2CO_3$ (935 mg, 2.88 mmol) and the resulting mixture was stirred at 25° C. for 18 hours. The mixture was diluted with EtOAc (50 mL) and brine (50 mL) and the layers were separated. The aqueous layer was extracted with EtOAc (2×50 mL), the combined organic layers were washed with water (50 mL), $NH_4Cl$ (2×50 mL) and brine (50 mL). The organics were dried over $Na_2SO_4$, filtered and concentrated under reduced pressure. The residue was purified via silica gel chromatography (10-50% EtOAc in hexans) to give the title compound as a oil (1 g, 1.40 mmol, 98% yield). MS (ES+) C30H33BrCl2N6O3 requires: 674, found: 675 [M+H]+.

Methyl 6-(4-(tert-butoxycarbonylamino)-4-methylpiperidin-1-yl)-3-(2,3-dichlorophenyl)-1-(4-methoxybenzyl)-1H-pyrazolo[3,4-b]pyrazine-5-carboxylate To a solution of tert-butyl 1-(5-bromo-3-(2,3-dichlorophenyl)-1-(4-methoxybenzyl)-1H-pyrazolo[3,4-b]pyrazin-6-yl)-4-methylpiperidin-4-ylcarbamate (500 mg, 0.739 mmol) in MeOH (20 mL) were added $Pd_2(dba)_3$ (52 mg, 0.074 mmol), Xantphos (43 mg, 0.074 mmol), and TEA (747 mg, 7.4 mmol). The mixture was flushed with carbon monoxide and stirred at 70° C. under an atmosphere of carbon monoxide (1 atm) for 18 hours. The mixture was absorbed onto Silica gel (2 g) and concentrated. The residue was purified via silica gel chromatography (10-40% EtOAc in hexanes) to give the title compound as a brown solid (200 mg, 0.305 mmol, 41% yield). MS (ES+) C32H36Cl2N6O5 requires: 654, found: 655 [M+H]+.

Tert-butyl 1-(3-(2,3-dichlorophenyl)-5-(hydroxycarbamoyl)-1-(4-methoxybenzyl)-1H-pyrazolo[3,4-b]pyrazin-6-yl)-4-methylpiperidin-4-ylcarbamate To a 0° C. solution of methyl 6-(4-(tert-butoxycarbonylamino)-4-methylpiperidin-1-yl)-3-(2,3-dichlorophenyl)-1-(4-methoxybenzyl)-1H-pyrazolo[3,4-b]pyrazine-5-carboxylate (100 mg, 0.153 mmol) in MeOH (3 mL) were added $NH_2OH$ (50%, 0.5 mL), NaOH (sat in MeOH, 0.5 mL) and the resulting mixture was stirred at 0° C. for 1 hour. Brine (25 mL) was added and the layers were separated. The aqueous layer was extracted with EtOAc (3×25 mL), the combined organics washed with brine (25 ml), dried over $Na_2SO_4$, filtered and concentrated to give the title compound as a brown solid (100 mg, 0.152 mmol). The product was used without further purification. MS (ES+) C31H35Cl2N7O5 requires: 655, found: 656 [M+H]+.

6-(4-Amino-4-methylpiperidin-1-yl)-3-(2,3-dichlorophenyl)-N-hydroxy-1H-pyrazolo[3,4-b]pyrazine-5-carboxamide To a microwave vial containing tert-butyl 1-(3-(2,3-dichlorophenyl)-5-(hydroxycarbamoyl)-1-(4-methoxybenzyl)-1H-pyrazolo[3,4-b]pyrazin-6-yl)-4-methylpiperidin-4-ylcarbamate (90 mg, 0.137 mmol) was TFA (2 mL). The vial was capped and stirred at 80° C. under microwave irradiation for 2 hours. The mixture was concentrated under reduced pressure and the residue was purified by reverse phase preparative HPLC (Mobile phase: A=0.1% TFA/$H_2O$, B=0.1% TFA/MeCN; Gradient: B=10-90%; 12 min; Column: C18) to give the title compound as a light yellow solid (7.2 mg, 0.016 mmol, 11% yield). MS (ES+) C18H19Cl2N7O2 requires: 435, found: 436 [M+H]+. $^1$H NMR (500 MHz, MeOD) δ 7.68 (t, J=7.8 Hz, 2H), 7.45 (t, J=7.9 Hz, 1H), 3.96 (d, J=14.3 Hz, 2H), 3.39 (dd, J=25.6, 15.0 Hz, 2H), 1.98 (dt, J=43.2, 11.6 Hz, 4H), 1.52 (s, 3H).

Example 14: 1-(3-(2,3-dichlorophenyl)-5-(difluoromethyl)-1H-pyrazolo[3,4-b]pyrazin-6-yl)-4-methylpiperidin-4-amine

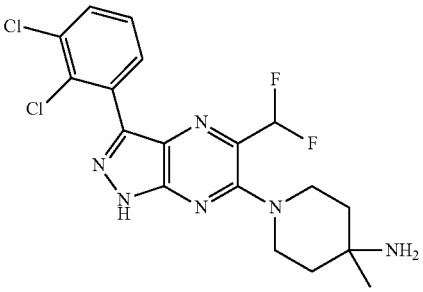 [SMILES: CC1(N)CCN(c2nc3[nH]nc(-c4cccc(Cl)c4Cl)c3nc2C(F)F)CC1]

Scheme 9

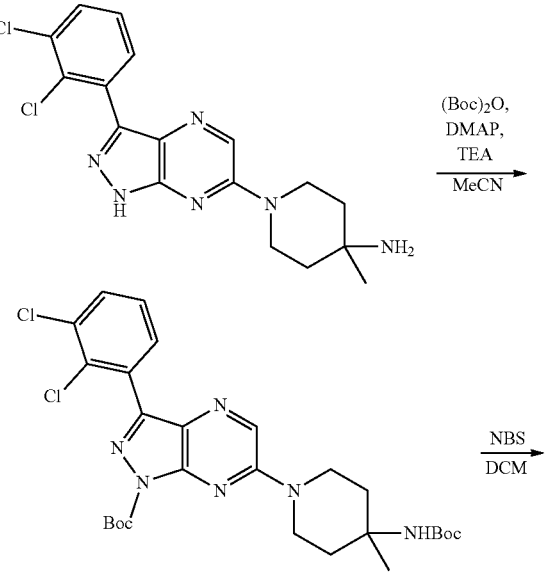

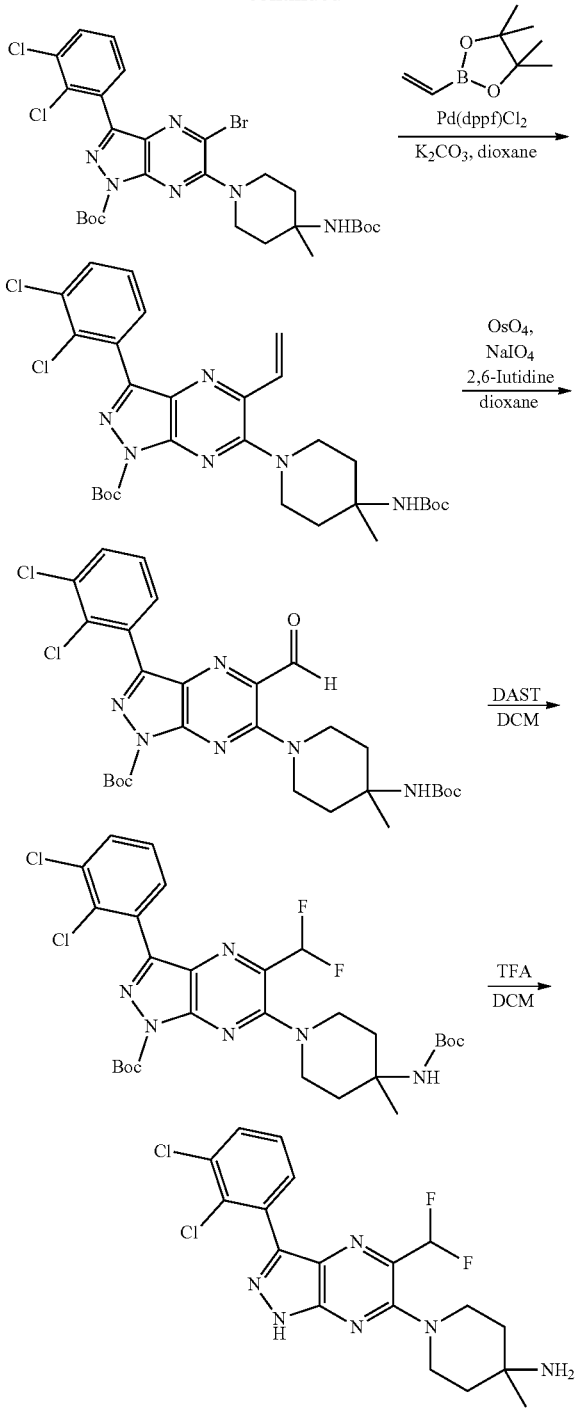

Tert-butyl 6-(4-((tert-butoxycarbonyl)amino)-4-methylpiperidin-1-yl)-3-(2,3-dichlorophenyl)-1H-pyrazolo[3,4-b]pyrazine-1-carboxylate To a solution of 1-(3-(2,3-dichlorophenyl)-1H-pyrazolo[3,4-b]pyrazin-6-yl)-4-methylpiperidin-4-amine (0.2 g, 0.530 mmol) in Acetonitrile (1.060 ml) were added TEA (0.111 ml, 0.795 mmol) and BOC2O (0.492 ml, 2.120 mmol) and followed by DMAP (6.48 mg, 0.053 mmol) and the resulting mixture was stirred at 60° C. for 66 h. The mixture was concentrated and the residue was purified via silica gel chromatography (0-50% EtOAc in hexanes to give tert-butyl 6-(4-((tert-butoxycarbonyl)amino)-4-methylpiperidin-1-yl)-3-(2,3-dichlorophenyl)-1H-pyrazolo[3,4-b]pyrazine-1-carboxylate (125 mg, 0.216 mmol, 40.8% yield) as a colorless liquid. MS (ES+) C27H34Cl2N6O4 requires: 576/578/560, found: 577/579/561 [M+H]+.

Tert-butyl 5-bromo-6-(4-((tert-butoxycarbonyl)amino)-4-methylpiperidin-1-yl)-3-(2,3-dichlorophenyl)-1H-pyrazolo[3,4-b]pyrazine-1-carboxylate To a solution of tert-butyl 6-(4-((tert-butoxycarbonyl)amino)-4-methylpiperidin-1-yl)-3-(2,3-dichlorophenyl)-1H-pyrazolo[3,4-b]pyrazine-1-carboxylate (100 mg, 0.173 mmol) in DCM (17320) at 0° C. was added NBS (46.2 mg, 0.260 mmol) and the resulting mixture was allowed to warm to RT over 1 h. The volatiles were removed under reduced pressure. The residue was adsorbed onto silica gel and purified via flash chromatography (0-100% EtOAc in hexanes) to give the title compound (82 mg, 0.125 mmol, 72.1% yield) as an orange amorphous material. MS (ES+) C27H33BrCl2N6O4 requires: 656, found: 657 [M+H]+.

Tert-butyl 6-(4-((tert-butoxycarbonyl)amino)-4-methylpiperidin-1-yl)-3-(2,3-dichlorophenyl)-5-vinyl-1H-1-pyrazolo[3,4-b]pyrazine-1-carboxylate A microwave vial was charged with tert-butyl 5-bromo-6-(4-((tert-butoxycarbonyl)amino)-4-methylpiperidin-1-yl)-3-(2,3-dichlorophenyl)-1H-pyrazolo[3,4-b]pyrazine-1-carboxylate (500 mg, 0.762 mmol), 4,4,5,5-tetramethyl-2-vinyl-1,3,2-dioxaborolane (153 mg, 0.990 mmol), K2CO3 (316 mg, 2.285 mmol) and Dioxane (6925 µl). The reaction mixture was degassed with N$_2$ for 1 min. PdCl2(dppf)-CH$_2$Cl$_2$Adduct (31.1 mg, 0.038 mmol) was added and the mixture was degassed with N$_2$ for an additional 1 min. The vial was sealed and the reaction mixture was heated to 120° C. in the microwave reactor for 1 h. The volatiles were removed under reduced pressure. The residue was adsorbed onto silica gel and purified via flash chromatography (0-100% EtOAc in hexanes) to give the title compound (240 mg, 0.398 mmol, 52.2% yield) as a yellow amorphous material. MS (ES+) C29H36Cl2N6O4 requires: 602, found: 603 [M+H]+.

Tert-butyl 6-(4-((tert-butoxycarbonyl)amino)-4-methylpiperidin-1-yl)-3-(2,3-dichlorophenyl)-5-formyl-1H-pyrazolo[3,4-b]pyrazine-1-carboxylate To a solution of tert-butyl (1-(3-(2,3-dichlorophenyl)-5-vinyl-1H-pyrazolo[3,4-b]pyrazin-6-yl)-4-methylpiperidin-4-yl)carbamate (240 mg, 0.477 mmol) in Dioxane (3575 µl) and Water (1192 µl) were added 2,6-lutidine (111 µl, 0.953 mmol) and osmium tetroxide (74.8 µl, 9.53 µmol) and the resulting mixture was stirred at RT for 3 h. The volatiles were removed under reduced pressure. The residue was adsorbed onto silica gel and purified via flash chromatography (0-100% EtOAc in hexanes) to give the title compound (188 mg, 0.372 mmol, 78% yield) as a pale yellow solid. MS (ES+) C28H34Cl2N6O5 requires: 605, found: 606 [M+H]+.

Tert-butyl 6-(4-((tert-butoxycarbonyl)amino)-4-methylpiperidin-1-yl)-3-(2,3-dichlorophenyl)-5-(difluoromethyl)-1H-pyrazolo[3,4-b]pyrazine-1-carboxylate To a solution of tert-butyl 6-(4-((tert-butoxycarbonyl)amino)-4-methylpiperidin-1-yl)-3-(2,3-dichlorophenyl)-5- formyl-1H-pyrazolo[3,4-b]pyrazine-1-carboxylate (22 mg, 0.036 mmol) in DCM (363 µl) at 0° C. was added DAST (14.40 µl, 0.109 mmol) and the resulting mixture was stirred at 25° C. for 18 h. The residue was adsorbed onto silica gel and purified via flash chromatography (0-100% EtOAc in hexanes) to give the title compound (12 mg, 0.019 mmol, 52.6% yield) as a yellow amorphous material. MS (ES+) C28H34Cl2F2N6O4 requires: 627, found: 628 [M+H]+.

1-(3-(2,3-Dichlorophenyl)-5-(difluoromethyl)-1H-pyrazolo[3,4-b]pyrazin-6-yl)-4-methylpiperidin-4-amine To a solution of tert-butyl 6-(4-((tert-butoxycarbonyl)amino)-4-methylpiperidin-1-yl)-3-(2,3-dichlorophenyl)-5-(difluoromethyl)-1H-pyrazolo[3,4-b]pyrazine-1-carboxylate (12 mg, 0.019 mmol) in DCM (382 µl) was added trifluoroacetic acid (44.2 µl, 0.574 mmol) and the resulting mixture was stirred at RT for 1 h. The volatiles were removed under reduced pressure. The sample was then frozen in MeOH/H2O and lyophilized. The title compound (10 mg, 0.018 mmol, 97% yield) was isolated as a pale yellow solid. MS (ES+) C18H18Cl2F2N6 requires: 427, found: 428 [M+H]+. $^1$H NMR (600 MHz, DMSO-$d_6$) δ 14.19 (s, 1H), 8.03 (s, 3H), 7.82 (dd, J=8.1, 1.5 Hz, 1H), 7.71 (dd, J=7.7, 1.5 Hz, 1H), 7.55 (t, J=7.9 Hz, 1H), 7.12 (t, J=53.4 Hz, 1H), 3.63-3.55 (m, 2H), 3.34-3.27 (m, 3H), 2.00-1.91 (m, 2H), 1.89-1.81 (m, 2H), 1.39 (s, 3H).

Example 15: 1-(3-(2,3-dichlorophenyl)-5-(fluoromethyl)-1H-pyrazolo[3,4-b]pyrazin-6-yl)-4-methylpiperidin-4-amine

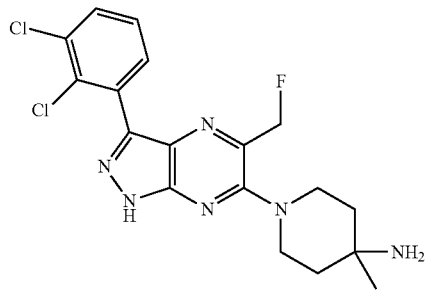 [SMILES: CC1(N)CCN(c2nc3[nH]nc(-c4cccc(Cl)c4Cl)c3nc2CF)CC1]

Scheme 10

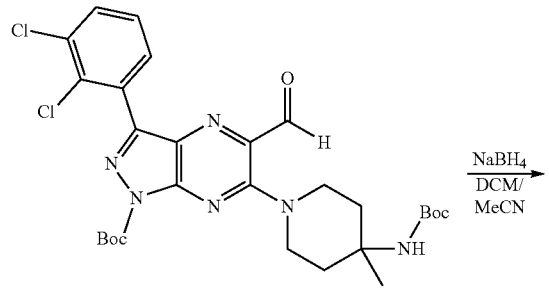

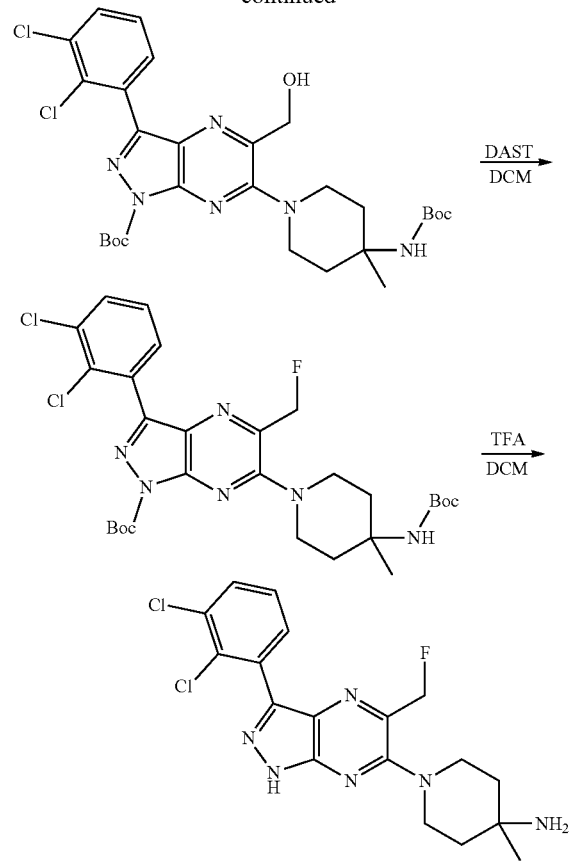

Tert-butyl 6-(4-((tert-butoxycarbonyl)amino)-4-methylpiperidin-1-yl)-3-(2,3-dichlorophenyl)-5-(hydroxymethyl)-1H-pyrazolo[3,4-b]pyrazine-1-carboxylate To a solution of tert-butyl 6-(4-((tert-butoxycarbonyl)amino)-4-methylpiperidin-1-yl)-3-(2,3-dichlorophenyl)-5-formyl-1H-pyrazolo[3,4-b]pyrazine-1-carboxylate (188 mg, 0.310 mmol) in DCM (1552 µl) and Methanol (1552 µl) was added sodium borohydride (35.2 mg, 0.931 mmol) and the resulting mixture was stirred at RT for 1 h. The volatiles were removed under reduced pressure. The yellow residue was dissolved in DCM (3 mL) and sat. Rochelles salt (2 mL) was added. The mixture was stirred for 18 hours. The layers were separated and the aqueous layer extracted with DCM (2×1 mL). The combined organics were dried over MgSO4, filtered, and concentrated. The residue was adsorbed onto silica gel and purified via flash chromatography (0-100% EtOAc in hexanes) to give the title compound (136 mg, 0.224 mmol, 72.1% yield) as a pale yellow amorphous material. MS (ES+) $C_{28}H_{36}Cl_2N_6O_5$ requires: 607, found: 608 [M+H]+.

Tert-butyl 6-(4-((tert-butoxycarbonyl)amino)-4-methylpiperidin-1-yl)-3-(2,3-dichlorophenyl)-5-(fluoromethyl)-1H-pyrazolo[3,4-b]pyrazine-1-carboxylate To a solution of tert-butyl 6-(4-((tert-butoxycarbonyl)amino)-4-methylpiperidin-1-yl)-3-(2,3-dichlorophenyl)-5-(hydroxymethyl)-1H-pyrazolo[3,4-b]pyrazine-1-carboxylate (136 mg, 0.224 mmol) in DCM (2239 µl) at 0° C. was added DAST (89 µl, 0.672 mmol) and the resulting mixture was allowed to warm to RT on own and stir 18 hours. The reaction was eluted through a 4 g plug of SiO2, eluting with DCM (5 mL) and EtOAc (15 mL). The volatiles were removed under reduced pressure. Isolated title compound crude (136 mg, 0.224 mmol, 100% yield). MS (ES+) C28H35Cl2FN6O4 requires: 609, found: 610 [M+H]$^+$.

1-(3-(2,3-Dichlorophenyl)-5-(fluoromethyl)-1H-pyrazolo[3,4-b]pyrazin-6-yl)-4-methylpiperidin-4-amine To a solution of tert-butyl 6-(4-((tert-butoxycarbonyl)amino)-4-methylpiperidin-1-yl)-3-(2,3-dichlorophenyl)-5-(fluoromethyl)-1H-pyrazolo[3,4-b]pyrazine-1-carboxylate (136 mg, 0.223 mmol) in DCM (2231 µl) was added TRIFLUOROACETIC ACID (17.19 µl, 0.223 mmol) and the resulting mixture was stirred at RT for 1 h. The volatiles were removed under reduced pressure. The residue was adsorbed onto Celite and purified via flash chromatography (0-10% MeOH in DCM w/0.5% NH4OH) to give the title compound (6 mg, 0.015 mmol, 6.57% yield) as a pale yellow solid. MS (ES+) C18H19Cl2FN6 requires: 408, found: 392 [M-NH2]$^+$. $^1$H NMR (600 MHz, DMSO-d$_6$) δ 13.99 (s, 1H), 8.03 (s, 3H), 7.80 (dd, J=8.1, 1.5 Hz, 1H), 7.70 (dd, J=7.7, 1.4 Hz, 1H), 7.54 (t, J=7.9 Hz, 1H), 5.53 (d, J=47.8 Hz, 2H), 3.66-3.55 (m, 2H), 3.31-3.25 (m, 2H), 1.99-1.91 (m, 2H), 1.89-1.80 (m, 2H), 1.40 (s, 3H).

Example 16: (6-((3S,4S)-4-amino-3-methyl-2-oxa-8-azaspiro[4.5]decan-8-yl)-3-(2,3-dichlorophenyl)-1H-pyrazolo[3,4-b]pyrazin-5-yl)methanol

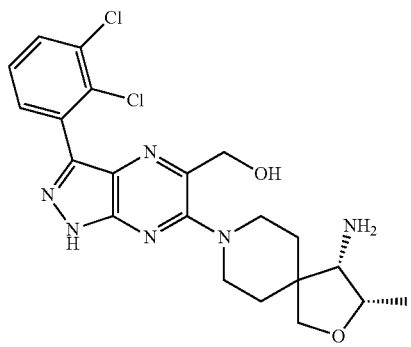 [SMILES: C[C@@H]1OCC2(CCN(c3nc4[nH]nc(-c5cccc(Cl)c5Cl)c4nc3CO)CC2)[C@@H]1N]

(6-((3S,4S)-4-amino-3-methyl-2-oxa-8-azaspiro[4.5]decan-8-yl)-3-(2,3-dichlorophenyl)-1H-pyrazolo[3,4-b]pyrazin-5-yl)methanol The title compound can be prepared from Example 7, step 2 using Intermediate 119. MS (ES+) C21H24Cl2N6O2 requires: 463, found: 464 [M+H]$^+$. $^1$H NMR (500 MHz, Chloroform-d) δ 7.64 (d, J=7.8 Hz, 1H), 7.59 (d, J=8.2 Hz, 1H), 7.34 (t, J=8.0 Hz, 2H), 4.79 (s, 2H), 4.28-4.16 (m, 2H), 3.86 (d, J=8.7 Hz, 1H), 3.74 (d, J=8.7 Hz, 1H), 3.56-3.44 (m, 2H), 3.26-3.08 (m, 2H), 3.06 (s, 1H), 2.01 (t, J=12.3 Hz, 2H), 1.87 (d, J=11.9 Hz, 2H), 1.79 (s, 1H), 1.27 (d, J=6.9 Hz, 3H).

Example 17: (6-((3S,4S)-4-amino-3-methyl-2-oxa-8-azaspiro[4.5]decan-8-yl)-3-(3-chloro-2-(ethylamino)pyridin-4-yl)-1H-pyrazolo[3,4-b]pyrazin-5-yl)methanol

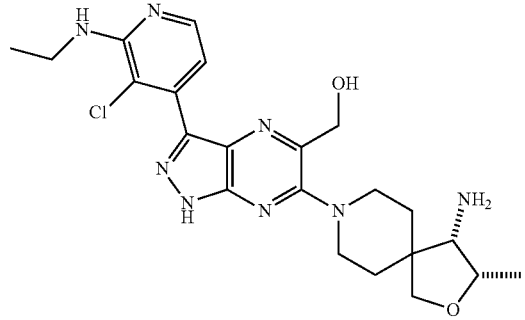 [SMILES: CCNc1nccc(-c2n[nH]c3nc(N4CCC5(CC4)CO[C@@H](C)[C@H]5N)c(CO)nc23)c1Cl]

(6-((3S,4S)-4-amino-3-methyl-2-oxa-8-azaspiro[4.5]decan-8-yl)-3-(3-chloro-2-(ethylamino)pyridin-4-yl)-1H-pyrazolo[3,4-b]pyrazin-5-yl)methanol The title compound can be prepared from Example 11 using Intermediate 119. MS (ES+) C22H29ClN8O2 requires: 472, found: 473 [M+H]$^+$. $^1$H NMR (600 MHz, Methanol-d$_4$) δ 8.03 (d, J=5.2 Hz, 1H), 6.96 (d, J=5.2 Hz, 1H), 4.76 (s, 2H), 4.29-4.19 (m, 2H), 3.86 (t, J=8.3 Hz, 2H), 3.73 (t, J=9.0 Hz, 2H), 3.68-3.62 (m, 2H), 3.54-3.49 (m, 2H), 3.26-3.11 (m, 2H), 3.05 (d, J=8.3, 4.9 Hz, 1H), 2.04-1.87 (m, 2H), 1.77 (t, J=18.3 Hz, 2H), 1.27 (t, J=7.2 Hz, 3H), 1.24-1.22 (m, 3H).

Example 18: (3S,4S)-8-(3-(3-chloro-2-(ethylamino)pyridin-4-yl)-5-methyl-1H-pyrazolo[3,4-b]pyrazin-6-yl)-3-methyl-2-oxa-8-azaspiro[4.5]decan-4-amine 2,2,2-trifluoroacetate

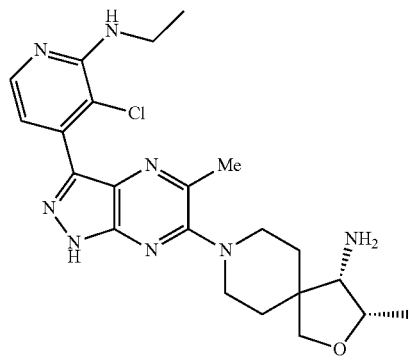 [SMILES: CCNc1nccc(-c2n[nH]c3nc(N4CCC5(CC4)CO[C@@H](C)[C@H]5N)c(C)nc23)c1Cl]

Scheme 11
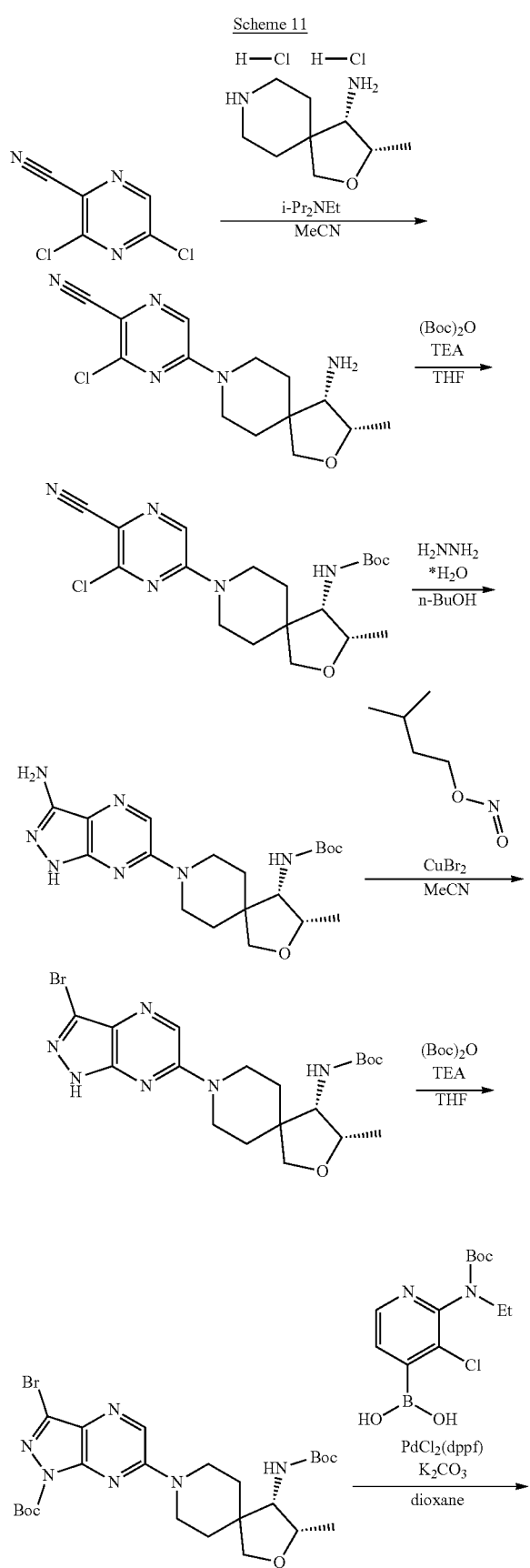
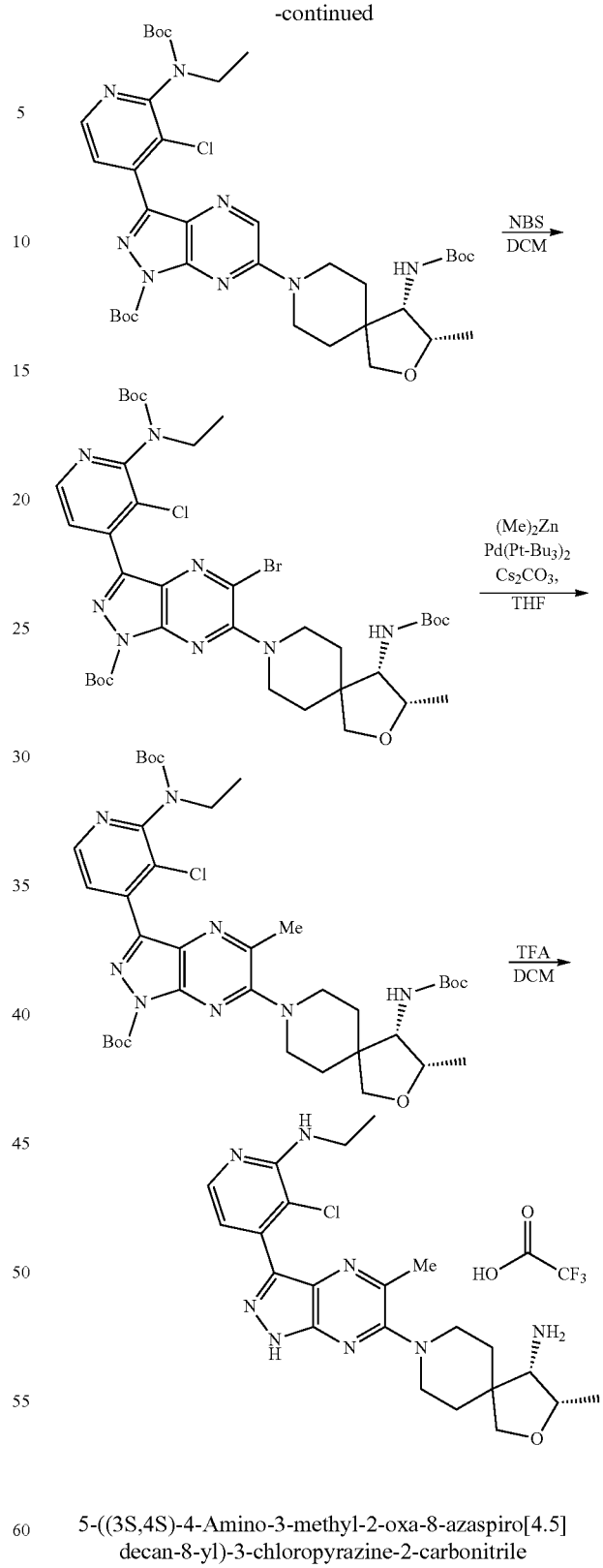
5-((3S,4S)-4-Amino-3-methyl-2-oxa-8-azaspiro[4.5]decan-8-yl)-3-chloropyrazine-2-carbonitrile
To a cooled 0° C. suspension of (3 S,4S)-3-methyl-2-oxa-8-azaspiro[4.5]decan-4-amine dihydrochloride (4.19 g, 17.2 mmol) in acetonitrile (86 mL) were added Hunig's base (15.06 mL, 86.0 mmol) and 3,5-dichloropyrazine-2-carbonitrile (3 g, 17.2 mmol). The resulting mixture was stirred at 25° C. for 1 h. The volatiles were removed under reduced pressure to give a yellow oil which was used without further purification. MS (ES+) C14H18ClN5O requires: 307, found: 308 [M+H]+.

Tert-butyl ((3S,4S)-8-(6-chloro-5-cyanopyrazin-2-yl)-3-methyl-2-oxa-8-azaspiro[4.5]decan-4-yl)carbamate To a solution of 5-((3S,4S)-4-amino-3-methyl-2-oxa-8-azaspiro[4.5]decan-8-yl)-3-chloropyrazine-2-carbonitrile (4.1 g, 13.3 mmol) in THF (66 mL) were added BOC-anhydride (3.7 mL, 15.9 mmol) and TEA (2.2 mL, 15.9 mmol) and the resulting mixture was stirred at 25° C. for 3 h. Water (20 mL) was added, and the layers were separated. The aqueous phase was extracted with EtOAc (3×25 mL), the combined organic layers were washed with sat. NaCl, dried over Na$_2$SO$_4$, filtered and concentrated under reduced pressure. The residue was purified via silica gel chromatography (0-5% MeOH in DCM to give the title compound (5 g, 12.2 mmol, 92% yield) as a yellow solid. MS (ES+) C19H26ClN5O3 requires: 407, found: 408 [M+H]+. $^1$H NMR (600 MHz, Chloroform-d) δ 7.98 (s, 1H), 4.66 (d, J=10.6 Hz, 1H), 4.20-4.08 (m, 1H), 4.04-3.97 (m, 1H), 3.90-3.70 (m, 3H), 3.68-3.58 (m, 2H), 1.90-1.77 (m, 2H), 1.78-1.70 (m, 1H), 1.66 (s, 1H), 1.63-1.57 (m, 2H), 1.52 (s, 9H), 1.20 (d, J=6.3 Hz, 3H).

Tert-butyl ((3S,4S)-8-(3-amino-1H-pyrazolo[3,4-b]pyrazin-6-yl)-3-methyl-2-oxa-8-azaspiro[4.5]decan-4-yl)carbamate To a solution of tert-butyl ((3S,4S)-8-(6-chloro-5-cyanopyrazin-2-yl)-3-methyl-2-oxa-8-azaspiro[4.5]decan-4-yl)carbamate (5 g, 12.2 mmol) in BuOH (60 mL) was added hydrazine hydrate (1.87 mL, 30.6 mmol) and the resulting mixture was stirred at 100° C. for 8 h. The volatiles were removed under reduced pressure to give a yellow oil that was used without further purification. MS (ES+) C19H29N7O3 requires: 403, found: 404 [M+H]+.

Tert-butyl ((3S,4S)-8-(3-bromo-1H-pyrazolo[3,4-b]pyrazin-6-yl)-3-methyl-2-oxa-8-azaspiro[4.5]decan-4-yl)carbamate To a cooled 0° C. solution of tert-butyl ((3S,4S)-8-(3-amino-1H-pyrazolo[3,4-b]pyrazin-6-yl)-3-methyl-2-oxa-8-azaspiro[4.5]decan-4-yl)carbamate (4 g, 9.9 mmol) and copper(II) bromide (2.43 g, 10.9 mmol) in acetonitrile (90 mL) was added isopentyl nitrite (3.60 mL, 26.8 mmol). The resulting mixture was stirred at 25° C. for 18 h in the absence of light. Water (20 mL) was added and the volatiles were removed under reduced pressure. The reaction mixture was diluted with DCM (50 mL) and washed with 3% NH$_4$OH (2×50 mL). The layers were separated, and the organic layer was washed with sat NaCl (30 mL), dried over Na$_2$SO$_4$, filtered and concentrated under reduced pressure. The residue was purified via silica gel chromatography (0-5% MeOH in DCM with 2% NH$_4$OH to give the title compound (1.7 g, 3.6 mmol, 36.7% yield) as a yellow liquid. MS (ES+) C$_{19}$H$_{27}$BrN$_6$O$_3$ requires: 467, found: 468 [M+H]+.

Tert-butyl 3-bromo-6-((3S,4S)-4-((tert-butoxycarbonyl)amino)-3-methyl-2-oxa-8-azaspiro[4.5]decan-8-yl)-1H-pyrazolo[3,4-b]pyrazine-1-carboxylate To a solution of tert-butyl ((3S,4S)-8-(3-bromo-1H-pyrazolo[3,4-b]pyrazin-6-yl)-3-methyl-2-oxa-8-azaspiro[4.5]decan-4-yl)carbamate (1.7 g, 3.6 mmol) in THF (35 mL) were added BOC-anhydride (1.013 mL, 4.3 mmol) and TEA (0.60 mL, 4.3 mmol) and the resulting mixture was stirred at 25° C. for 6 h. The volatiles were removed under reduced pressure and the residue was purified via silica gel chromatography (0-5% MeOH in DCM with 2% NH$_4$OH to give the title compound (1.3 g, 2.2 mmol, 63.0% yield) as a yellow liquid. MS (ES+) C$_{24}$H$_{35}$BrN$_6$O$_5$ requires: 567, found: 568 [M+H]+.

Tert-butyl 3-(2-((tert-butoxycarbonyl)(ethyl)amino)-3-chloropyridin-4-yl)-6-((3S,4S)-4-((tert-butoxycarbonyl)amino)-3-methyl-2-oxa-8-azaspiro[4.5]decan-8-yl)-1H-pyrazolo[3,4-b]pyrazine-1-carboxylate A solution of tert-butyl 3-bromo-6-((3S,4S)-4-((tert-butoxycarbonyl)amino)-3-methyl-2-oxa-8-azaspiro[4.5]decan-8-yl)-1H-pyrazolo[3,4-b]pyrazine-1-carboxylate (1.2 g, 2.1 mmol), (2-((tert-butoxycarbonyl)(ethyl)amino)-3-chloropyridin-4-yl)boronic acid (1.144 g, 3.8 mmol) and K$_2$CO$_3$ (1.169 g, 8.4 mmol) in dioxane (15 mL) was degassed with N$_2$ for 1 minutes. PdCl$_2$(dppf)-CH$_2$Cl$_2$ adduct (0.345 g, 0.4 mmol) was added and the mixture was degassed with N$_2$ for an additional 2 minutes. The reaction mixture was heated to 100° C. and stirred for 3 h. Water (5 mL) was added, the reaction mixture was filtered through Celite, and the filtrate was concentrated under reduced pressure. The reaction mixture was diluted with DCM (20 mL) and washed with water (15 mL). The layers were separated, and the organic layer was washed with sat NaCl (15 mL), dried over Na$_2$SO$_4$, filtered and concentrated under reduced pressure. The residue was purified via silica gel chromatography (0-5% MeOH in DCM with 2% NH$_4$OH to give the title compound (1.3 g, 1.7 mmol, 83% yield) as a yellow foam solid. MS (ES+) C36H51ClN8O7 requires: 743, found: 744 [M+H]+.

Tert-butyl 5-bromo-3-(2-((tert-butoxycarbonyl)(ethyl)amino)-3-chloropyridin-4-yl)-6-((3S,4S)-4-((tert-butoxycarbonyl)amino)-3-methyl-2-oxa-8-azaspiro[4.5]decan-8-yl)-1H-pyrazolo[3,4-b]pyrazine-1-carboxylate To a cooled 0° C. solution of tert-butyl 3-(2-((tert-butoxycarbonyl)(ethyl)amino)-3-chloropyridin-4-yl)-6-((3S,4S)-4-((tert-butoxycarbonyl)amino)-3-methyl-2-oxa-8-azaspiro[4.5]decan-8-yl)-1H-pyrazolo[3,4-b]pyrazine-1-carboxylate (1.3 g, 1.7 mmol) in DCM (17 mL) was added NBS (0.467 g, 2.6 mmol). The resulting mixture was stirred at 50° C. for 2 h. Sat. NaHCO$_3$(10 mL) was added, and the layers were separated. The aqueous phase was extracted with DCM (3×10 mL), the combined organic layers were washed with water, dried over Na$_2$SO$_4$, filtered and concentrated under reduced pressure. The residue was purified via silica gel chromatography (0-5% MeOH in DCM with 2% NH$_4$OH to give the title compound (1.28 g, 1.5 mmol, 89% yield) as a yellow foam solid. MS (ES+) C36H50BrClN8O7 requires: 822, found: 823 [M+H]+.

Tert-butyl 3-(2-((tert-butoxycarbonyl)(ethyl)amino)-3-chloropyridin-4-yl)-6-((3S,4S)-4-((tert-butoxycarbonyl)amino)-3-methyl-2-oxa-8-azaspiro[4.5]decan-8-yl)-5-methyl-1H-pyrazolo[3,4-b]pyrazine-1-carboxylate To a degassed and 0° C. solution of tert-butyl 5-bromo-3-(2-((tert-butoxycarbonyl)(ethyl)amino)-3-chloropyridin- 4-yl)-6-((3S,4S)-4-((tert-butoxycarbonyl)amino)-3-methyl-2-oxa-8-azaspiro[4.5]decan-8-yl)-1H-pyrazolo[3,4-b]pyrazine-1-carboxylate (500 mg, 0.6 mmol) in THF (6.0 mL) were added bis(tri-t-butylphosphine)palladium(0) (15.54 mg, 0.03 mmol) and dimethylzinc (912 µl, 0.9 mmol). The resulting mixture was stirred at 20° C. for 1 h. MeOH (3 mL) was added and the volatiles were removed under reduced pressure. The residue was purified by reverse phase preparative HPLC (Mobile phase: A=0.1% TFA/H$_2$O, B=0.1% TFA/MeCN; Gradient: B=50-90%; 12 min; Column: Y) to give the title compound (26 mg, 0.03 mmol, 5.65% yield) as a yellow liquid. MS (ES+) C37H53ClN8O7 requires: 757, found: 758 [M+H]$^+$. (3S,4S)-8-(3-(3-chloro-2-(Ethylamino)pyridin-4-yl)-5-methyl-1H-pyrazolo[3,4-b]pyrazin-6-yl)-3-methyl-2-oxa-8-azaspiro[4.5]decan-4-amine 2,2,2-trifluoroacetate. To a solution of tert-butyl 3-(2-((tert-butoxycarbonyl)(ethyl)amino)-3-chloropyridin-4-yl)-6-((3S,4S)-4-((tert-butoxycarbonyl)amino)-3-methyl-2-oxa-8-azaspiro[4.5]decan-8-yl)-5-methyl-1H-pyrazolo[3,4-b]pyrazine-1-carboxylate (26 mg, 0.03 mmol) in DCM (343 µl) was added TFA (26.4 µl, 0.3 mmol) and the resulting mixture was stirred at 25° C. for 3 h. The volatiles were removed under reduced pressure to give the title compound (18 mg, 0.032 mmol, 92% yield) as a yellow oil. MS (ES+) C22H29ClN8O requires: 456, found: 457 [M+H]$^+$. $^1$H NMR (600 MHz, Methanol-d$_4$) δ 7.95 (d, J=6.7 Hz, 1H), 7.66 (d, J=6.7 Hz, 1H), 4.34-4.29 (m, 1H), 3.98 (d, J=8.9 Hz, 1H), 3.88 (d, J=9.2 Hz, 1H), 3.77-3.66 (m, 2H), 3.61 (q, J=7.2 Hz, 2H), 3.49 (d, J=4.1 Hz, 1H), 3.11-2.99 (m, 2H), 2.68 (s, 3H), 2.08-1.99 (m, 2H), 1.99-1.94 (m, 1H), 1.83-1.76 (m, 1H), 1.39 (t, J=7.2 Hz, 3H), 1.33 (d, J=6.5 Hz, 3H).

Scheme 12

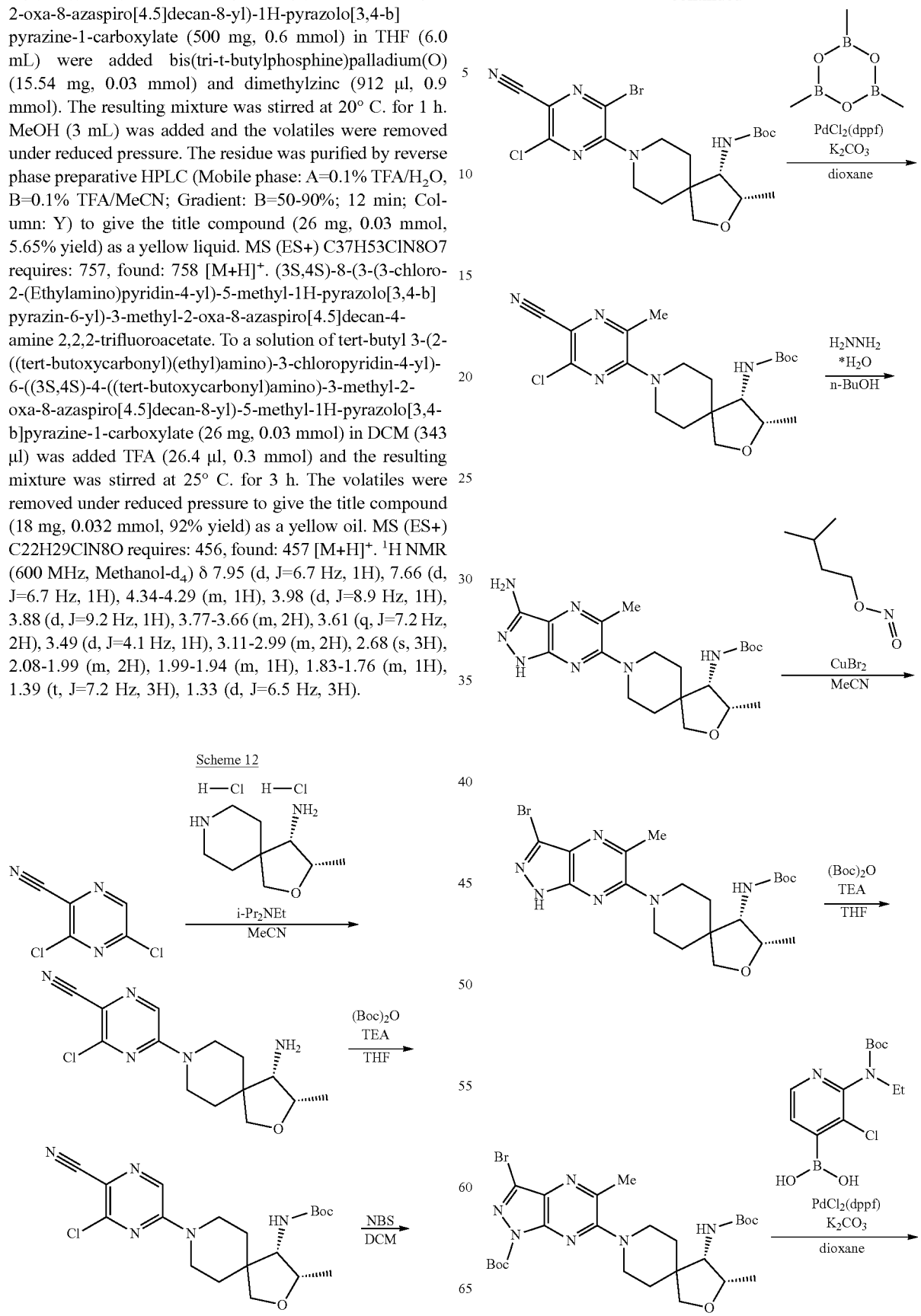

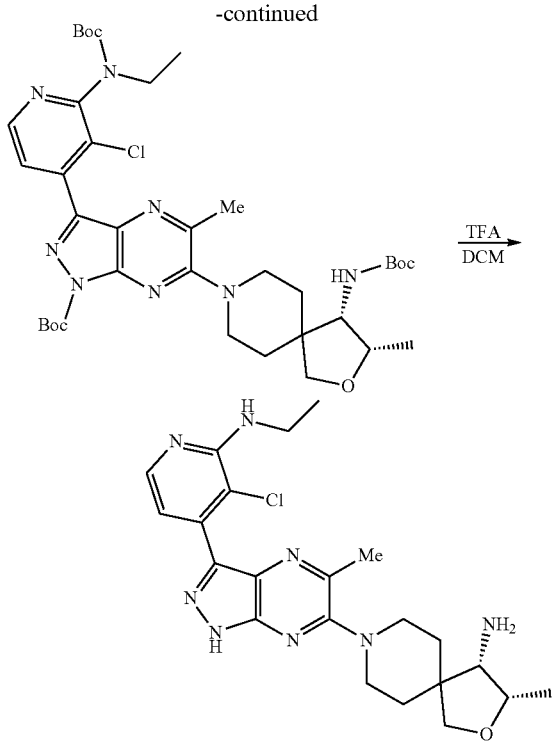

5-((3S,4S)-4-Amino-3-methyl-2-oxa-8-azaspiro[4.5]
decan-8-yl)-3-chloropyrazine-2-carbonitrile To a cooled 0° C. suspension of (3S,4S)-3-methyl-2-oxa-8-azaspiro[4.5]decan-4-amine dihydrochloride (28.0 g, 115 mmol) in acetonitrile (575 ml) were added Hunig's base (100 ml, 575 mmol) and 3,5-dichloropyrazine-2-carbonitrile (20 g, 115 mmol). The resulting mixture was stirred at 25° C. for 1 h. The volatiles were removed under reduced pressure to give a yellow oil which was used without further purification. MS (ES+) C14H18ClN5O requires: 307, found: 308 [M+H]+.

Tert-butyl ((3S,4S)-8-(6-chloro-5-cyanopyrazin-2-yl)-3-methyl-2-oxa-8-azaspiro[4.5]decan-4-yl)carbamate To a solution of 5-((3S,4S)-4-amino-3-methyl-2-oxa-8-azaspiro[4.5]decan-8-yl)-3-chloropyrazine-2-carbonitrile (35.4 g, 115 mmol) in DCM (460 ml) were added BOC-anhydride (32.0 ml, 138 mmol) and TEA (19.24 ml, 138 mmol) and the resulting mixture was stirred at 25° C. for 3 h. H2O (100 mL) was added, and the layers were separated. The aqueous phase was extracted with EtOAc (3×50 mL), the combined organic layers were washed with sat NaCl, dried over Na2SO4, filtered and concentrated under reduced pressure. The residue was purified via silica gel chromatography (0-90% EtOAc in hexanes to give tert-butyl ((3S,4S)-8-(6-chloro-5-cyanopyrazin-2-yl)-3-methyl-2-oxa-8-azaspiro[4.5]decan-4-yl)carbamate (38 g, 93 mmol, 81% yield) as a yellow foam solid. MS (ES+) C19H26ClN5O3 requires: 407, found: 408 [M+H]+.

Tert-butyl ((3S,4S)-8-(3-bromo-6-chloro-5-cyanopyrazin-2-yl)-3-methyl-2-oxa-8-azaspiro[4.5]decan-4-yl)carbamate To a solution of tert-butyl ((3S,4S)-8-(6-chloro-5-cyano-pyrazin-2-yl)-3-methyl-2-oxa-8-azaspiro[4.5]decan-4-yl) carbamate (46 g, 113 mmol) in DMF (564 ml) was added NBS (30.1 g, 169 mmol) and the resulting mixture was stirred at 50° C. for 18 h. The volatiles were removed under reduced pressure and the residue was purified via silica gel chromatography (0-80% EtOAc in hexanes to give tert-butyl ((3S,4S)-8-(3-bromo-6-chloro-5-cyanopyrazin-2-yl)-3-methyl-2-oxa-8-azaspiro[4.5]decan-4-yl)carbamate (24 g, 49.3 mmol, 43.7% yield) as a pale yellow foam solid. MS (ES+) C19H25BrClN5O3 requires: 486, found: 486,487 [M+H]+.

Tert-butyl ((3S,4S)-8-(6-chloro-5-cyano-3-methylpyrazin-2-yl)-3-methyl-2-oxa-8-azaspiro[4.5]decan-4-yl)carbamate A solution of tert-butyl ((3S,4S)-8-(3-bromo-6-chloro-5-cyanopyrazin-2-yl)-3-methyl-2-oxa-8-azaspiro[4.5]decan-4-yl)carbamate (5 g, 10.27 mmol), 2,4,6-trimethyl-1,3,5,2,4,6-trioxatriborinane (0.574 ml, 4.11 mmol) and K2CO3 (2.84 g, 20.54 mmol) in dioxane (51.4 ml) was degassed with N2 for 2 minutes. PdCl2(dppf)-CH2Cl2 adduct (0.839 g, 1.027 mmol) was added and the mixture was degassed with N2 for an additional 1 minutes. The reaction mixture was heated to 90° C. and stirred for 72 h. The reaction mixture was allowed to cool to room temperature and filtered through Celite, and the filtrate was concentrated under reduced pressure. The residue was purified via silica gel chromatography (0-70% EtOAc in hexanes to give tert-butyl ((3S,4S)-8-(6-chloro-5-cyano-3-methylpyrazin-2-yl)-3-methyl-2-oxa-8-azaspiro[4.5]decan-4-yl)carbamate (3.3 g, 7.82 mmol, 76% yield) as a yellow liquid. MS (ES+) C20H28ClN5O3 requires: 421, found: 422 [M+H]+.

Tert-butyl ((3S,4S)-8-(3-amino-5-methyl-1H-pyrazolo[3,4-b]pyrazin-6-yl)-3-methyl-2-oxa-8-azaspiro[4.5]decan-4-yl)carbamate To a solution of tert-butyl ((3S,4S)-8-(6-chloro-5-cyano-3-methylpyrazin-2-yl)-3-methyl-2-oxa-8-azaspiro[4.5]decan-4-yl)carbamate (3.3 g, 7.82 mmol) in BuOH (78 ml) was added hydrazine hydrate (0.979 g, 19.55 mmol) and the resulting mixture was stirred at 105° C. for 8 h. The reaction mixture was allowed to cool to room temperature and the volatiles were removed under reduced pressure. The residue was purified via silica gel chromatography (0-10% MeOH in DCM to give tert-butyl ((3S,4S)-8-(3-amino-5-methyl-1H-pyrazolo[3,4-b]pyrazin-6-yl)-3-methyl-2-oxa-8-azaspiro[4.5]decan-4-yl)carbamate (1.6 g, 3.83 mmol, 49.0% yield) as a yellow liquid. MS (ES+) C20H31N7O3 requires: 417, found: 418 [M+H]+.

Tert-butyl ((3S,4S)-8-(3-bromo-5-methyl-1H-pyrazolo[3,4-b]pyrazin-6-yl)-3-methyl-2-oxa-8-azaspiro[4.5]decan-4-yl)carbamate To a solution of tert-butyl ((3S,4S)-8-(3-amino-5-methyl-1H-pyrazolo[3,4-b]pyrazin-6-yl)-3-methyl-2-oxa-8-azaspiro[4.5]decan-4-yl)carbamate (1.6 g, 3.83 mmol) in acetonitrile (38.3 ml) were added copper(II) bromide (0.942 g, 4.22 mmol) and isopentyl nitrite (1.122 g, 9.58 mmol) and the resulting mixture was stirred at 25° C. for 18 h. The volatiles were removed under reduced pressure. The reaction mixture was diluted with EtOAc (20 mL), NH4OH (20 mL, 10% solution) was added, and the layers were separated. The organic layers were washed with NH4OH (2×20 mL, 10% solution), sat NaCl, dried over Na2SO4, filtered and concentrated under reduced pressure. The residue was purified via silica gel chromatography (0-5% MeOH in DCM to give tert-butyl ((3S,4S)-8-(3-bromo-5-methyl-1H-pyrazolo[3,4-b]pyrazin-6-yl)-3-methyl-2-oxa-8-azaspiro[4.5]decan-4-yl)carbamate (810 mg, 1.683 mmol, 43.9% yield) as a dark liquid. MS (ES+) $C_{20}H_{29}BrN_6O_3$ requires: 481, found: 482, 483 [M+H]$^+$.

Tert-butyl 3-bromo-6-((3S,4S)-4-((tert-butoxycarbonyl)amino)-3-methyl-2-oxa-8-azaspiro[4.5]decan-8-yl)-5-methyl-1H-pyrazolo[3,4-b]pyrazine-1-carboxylate To a solution of tert-butyl ((3 S,4 S)-8-(3-bromo-5-methyl-1H-pyrazolo[3,4-b]pyrazin-6-yl)-3-methyl-2-oxa-8-azaspiro[4.5]decan-4-yl)carbamate (810 mg, 1.683 mmol) in THF (16.800 mL) were added BOC-anhydride (0.469 mL, 2.019 mmol) and TEA (0.352 mL, 2.52 mmol) and the resulting mixture was stirred at 25° C. for 12 h. H$_2$O (20 mL) was added, and the layers were separated. The aqueous phase was extracted with EtOAc (3×15 mL), the combined organic layers were washed with sat NaCl, dried over Na$_2$SO$_4$, filtered and concentrated under reduced pressure. The residue was purified via silica gel chromatography (0-85% EtOAc in hexanes to give tert-butyl 3-bromo-6-((3 S,4S)-4-((tert-butoxycarbonyl)amino)-3-methyl-2-oxa-8-azaspiro[4.5]decan-8-yl)-5-methyl-1H-pyrazolo[3,4-b]pyrazine-1-carboxylate (650 mg, 1.118 mmol, 66.4% yield) as a pale yellow foam solid. MS (ES+) $C_{25}H_{37}BrN_6O_5$ requires: 581, found: 582, 583 [M+H]$^+$.

Tert-butyl 3-(2-((tert-butoxycarbonyl)(ethyl)amino)-3-chloropyridin-4-yl)-6-((3S,4S)-4-((tert-butoxycarbonyl)amino)-3-methyl-2-oxa-8-azaspiro[4.5]decan-8-yl)-5-methyl-1H-pyrazolo[3,4-b]pyrazine-1-carboxylate A solution of tert-butyl 3-bromo-6-((3S,4S)-4-((tert-butoxycarbonyl)amino)-3-methyl-2-oxa-8-azaspiro[4.5]decan-8-yl)-5-methyl-1H-pyrazolo[3,4-b]pyrazine-1-carboxylate (2.56 g, 4.40 mmol), (2-((tert-butoxycarbonyl)(ethyl)amino)-3-chloropyridin-4-yl)boronic acid (2.382 g, 7.92 mmol) and K$_2$CO$_3$ (2.434 g, 17.61 mmol) in dioxane (29.3 ml) was degassed with N$_2$ for 1 minutes. PdCl$_2$(dppf)-CH$_2$Cl$_2$ adduct (0.719 g, 0.880 mmol) was added and the mixture was degassed with N$_2$ for an additional 2 minutes. The reaction mixture was heated to 100° C. and stirred for 3 h. Water (5 mL) was added, the reaction mixture was filtered through Celite, and the filtrate was concentrated under reduced pressure. The reaction mixture was diluted with DCM (20 mL) and washed with H$_2$O (15 mL). The layers were separated, and the organic layer was washed with sat NaCl (15 mL), dried over Na$_2$SO$_4$, filtered and concentrated under reduced pressure. The residue was purified via silica gel chromatography (0-5% MeOH in DCM with 2% NH$_4$OH to give tert-butyl 3-(2-((tert-butoxycarbonyl)(ethyl)amino)-3-chloropyridin-4-yl)-6-((3S,4S)-4-((tert-butoxycarbonyl)amino)-3-methyl-2-oxa-8-azaspiro[4.5]decan-8-yl)-5-methyl-1H-pyrazolo[3,4-b]pyrazine-1-carboxylate (2.67 g, 3.52 mmol, 80% yield) as a yellow foam solid. MS (ES+) C36H51ClN8O7 requires: 743, found: 744 [M+H]$^+$.

(3S,4S)-8-(3-(3-chloro-2-(ethylamino)pyridin-4-yl)-5-methyl-1H-pyrazolo[3,4-b]pyrazin-6-yl)-3-methyl-2-oxa-8-azaspiro[4.5]decan-4-amine To a solution of tert-butyl 3-(2-((tert-butoxycarbonyl)(ethyl)amino)-3-chloropyridin-4-yl)-6-((3S,4S)-4-((tert-butoxycarbonyl)amino)-3-methyl-2-oxa-8-azaspiro[4.5]decan-8-yl)-5-methyl-1H-pyrazolo[3,4-b]pyrazine-1-carboxylate (2 g, 2.64 mmol) in DCM (26.4 ml) was added TFA (2.035 ml, 26.4 mmol) and the resulting mixture was stirred at 25° C. for 5 h. The volatiles were removed under reduced pressure and the residue was purified via silica gel chromatography (0-10% MeOH in DCM with 2% NH$_4$OH to give (3S,4S)-8-(3-(3-chloro-2-(ethylamino)pyridin-4-yl)-5-methyl-1H-pyrazolo[3,4-b]pyrazin-6-yl)-3-methyl-2-oxa-8-azaspiro[4.5]decan-4-amine as a pale yellow solid. MS (ES+) C22H29ClN8O requires: 456, found: 457 [M+H]$^+$. $^1$H NMR (600 MHz, Methanol-d$_4$) δ 7.95 (d, J=6.7 Hz, 1H), 7.66 (d, J=6.7 Hz, 1H), 4.34-4.29 (m, 1H), 3.98 (d, J=8.9 Hz, 1H), 3.88 (d, J=9.2 Hz, 1H), 3.77-3.66 (m, 2H), 3.61 (q, J=7.2 Hz, 2H), 3.49 (d, J=4.1 Hz, 1H), 3.11-2.99 (m, 2H), 2.68 (s, 3H), 2.08-1.99 (m, 2H), 1.99-1.94 (m, 1H), 1.83-1.76 (m, 1H), 1.39 (t, J=7.2 Hz, 3H), 1.33 (d, J=6.5 Hz, 3H).

Example 19: (3S,4S)-8-(5-Chloro-3-(3-chloro-2-(ethylamino)pyridin-4-yl)-1H-pyrazolo[3,4-b]pyrazin-6-yl)-3-methyl-2-oxa-8-azaspiro[4.5]decan-4-amine

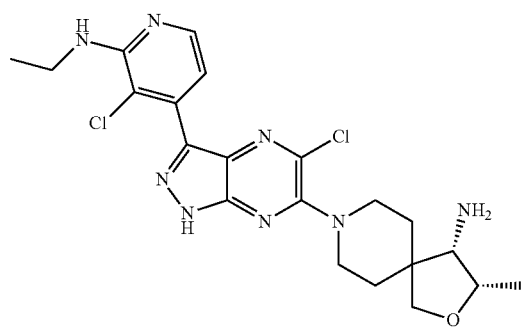 [SMILES: CCNc1nccc(-c2n[nH]c3nc(N4CCC5(CC4)CO[C@@H](C)[C@H]5N)c(Cl)nc23)c1Cl]

Scheme 13

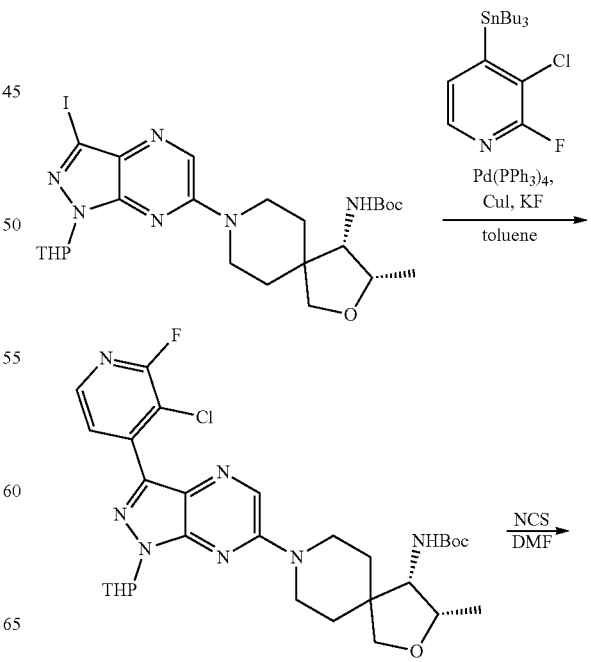

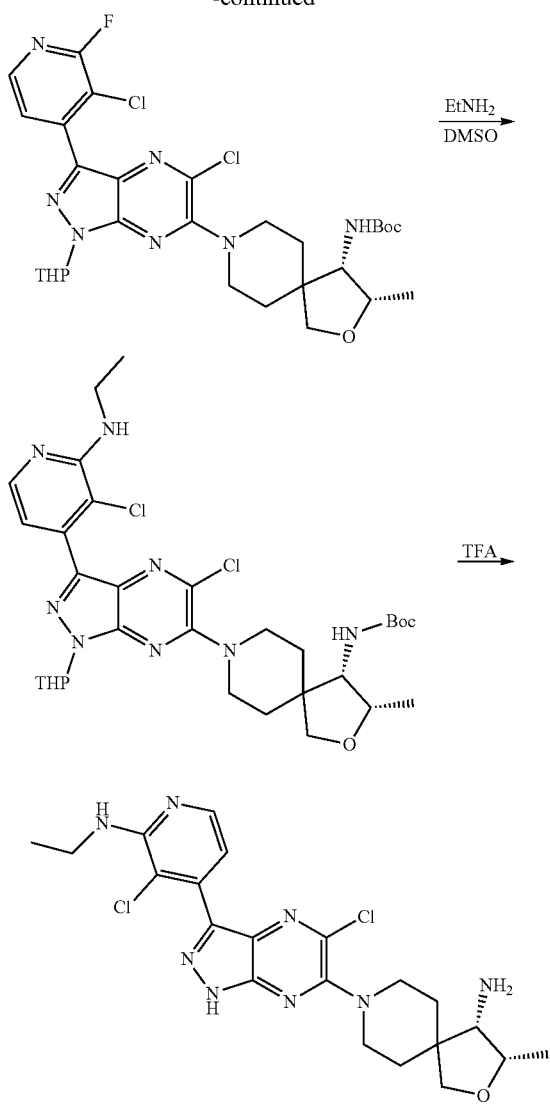

Tert-butyl (3S,4S)-8-(3-(3-chloro-2-fluoropyridin-4-yl)-1-(tetrahydro-2H-pyran-2-yl)-1H-pyrazolo[3,4-b]pyrazin-6-yl)-3-methyl-2-oxa-8-azaspiro[4.5]decan-4-ylcarbamate To a solution of 3-chloro-2-fluoro-4-(tributylstannyl)pyridine [Intermediate 120] (842 mg, 2 mmol) and tert-butyl (3S,4S)-8-(3-iodo-1-(tetrahydro-2H-pyran-2-yl)-1H-pyrazolo[3,4-b]pyrazin-6-yl)-3-methyl-2-oxa-8-azaspiro[4.5]decan-4-ylcarbamate (600 mg, 1 mmol) in toluene (25 mL) were added Pd(Ph$_3$P)$_4$ (116 mg, 0.1 mmol), CuI (19 mg, 0.1 mmol), and KF (232 mg, 4 mmol). The reaction mixture was purged with Ar for 2 min. and allowed to stir at 120° C. for 48 hours. The residue was purified via silica gel chromatography (0-55% EtOAc in hexanes to give the title compound as a light yellow solid (165 mg, 0.271 mmol, 28% yield). MS (ES+) C29H37ClFN7O4 requires: 601, found: 602 [M+H]$^+$.

Tert-butyl (3S,4S)-8-(5-chloro-3-(3-chloro-2-fluoropyridin-4-yl)-1-(tetrahydro-2H-pyran-2-yl)-1H-pyrazolo[3,4-b]pyrazin-6-yl)-3-methyl-2-oxa-8-azaspiro[4.5]decan-4-ylcarbamate To a solution of tert-butyl (3S,4S)-8-(3-(3-chloro-2-fluoropyridin-4-yl)-1-(tetrahydro-2H-pyran-2-yl)-1H-pyrazolo[3,4-b]pyrazin-6-yl)-3-methyl-2-oxa-8-azaspiro[4.5]decan-4-ylcarbamate (100 mg, 0.166 mmol) in DMF (5 mL) was added NCS (220 mg, 1.661 mmol) and the resulting mixture was stirred at 25° C. for 1 hour. Sat. NaHSO$_3$ (1 mL) and brine (15 mL) were added, and the layers were separated. The aqueous layer was extracted with EtOAc (3×15 mL), the combined organic layers were washed with water (15 mL), brine (15 mL), dried over Na$_2$SO$_4$, filtered and concentrated under reduced pressure to give the title compound as a brown oil (50 mg, 0.078 mmol, 45% yield). The product was used without further purification. MS (ES+) C29H36Cl2FN7O4 requires: 635, found: 636 [M+H]$^+$.

Tert-butyl (3S,4S)-8-(5-chloro-3-(3-chloro-2-(ethylamino)pyridin-4-yl)-1-(tetrahydro-2H-pyran-2-yl)-1H-pyrazolo[3,4-b]pyrazin-6-yl)-3-methyl-2-oxa-8-azaspiro[4.5]decan-4-ylcarbamate To a solution of tert-butyl (3S,4S)-8-(5-chloro-3-(3-chloro-2-fluoropyridin-4-yl)-1-(tetrahydro-2H-pyran-2-yl)-1H-pyrazolo[3,4-b]pyrazin-6-yl)-3-methyl-2-oxa-8-azaspiro[4.5]decan-4-ylcarbamate (40 mg, 0.062 mmol) in DMSO (0.5 mL) was added EtNH$_2$ (70%, 0.1 mL) and the resulting mixture was stirred at 25° C. for 2 hours. Water (10 mL) was added, and the layers were separated. The aqueous layer was extracted with EtOAc (3×15 mL), the combined organic layers were washed with water (15 mL), brine (15 mL), dried over Na$_2$SO$_4$, filtered and concentrated under reduced pressure to give the title compound as a brown oil (50 mg, 0.075 mmol). The product was used without further purification. MS (ES+) C31H42Cl2N8O4 requires: 660, found: 661 [M+H]$^+$.

(3S,4S)-8-(5-Chloro-3-(3-chloro-2-(ethylamino)pyridin-4-yl)-1H-pyrazolo[3,4-b]pyrazin-6-yl)-3-methyl-2-oxa-8-azaspiro[4.5]decan-4-amine To tert-butyl (3S,4S)-8-(5-chloro-3-(3-chloro-2-(ethylamino)pyridin-4-yl)-1-(tetrahydro-2H-pyran-2-yl)-1H-pyrazolo[3,4-b]pyrazin-6-yl)-3-methyl-2-oxa-8-azaspiro[4.5]decan-4-ylcarbamate (50 mg, 0.075 mmol) was added TFA (2 ml) and the resulting mixture was stirred at 25° C. for 1 hour. The volitiles were removed under reduced pressure and the residue was purified by reverse phase preparative HPLC (Mobile phase: A=0.1% TFA/H$_2$O, B=0.1% TFA/MeCN; Gradient: B=10-90%; 12 min; Column: C18) to give the title compound as a light yellow solid (7 mg, 0.014 mmol, 18% yield). MS (ES+) C21H26Cl2N8O requires: 476, found: 477 [M+H]$^+$. $^1$H NMR (500 MHz, MeOD) δ 8.02 (d, J=6.0 Hz, 1H), 7.30 (d, J=6.0 Hz, 1H), 4.34 (dd, J=6.5, 4.2 Hz, 1H), 4.11-3.94 (m, 3H), 3.91 (d, J=9.2 Hz, 1H), 3.59 (q, J=7.2 Hz, 2H), 3.51 (d, J=4.1 Hz, 1H), 3.23-3.00 (m, 2H), 2.13-1.90 (m, 3H), 1.82 (d, J=12.7 Hz, 1H), 1.36 (t, J=7.2 Hz, 6H).

Example 20: (6-((3S,4S)-4-Amino-3-methyl-2-oxa-8-azaspiro[4.5]decan-8-yl)-3-(3-chloro-2-(methylamino)pyridin-4-yl)-1H-pyrazolo[3,4-b]pyrazin-5-yl)methanol

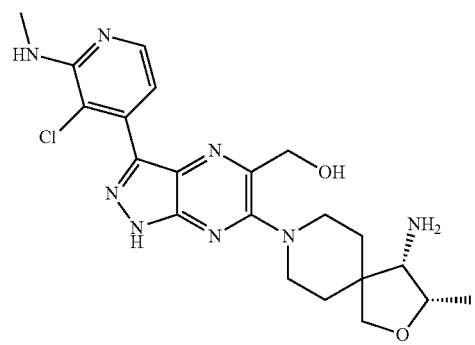

Scheme 14

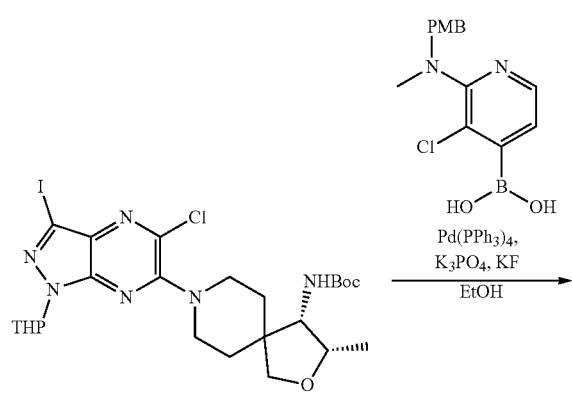

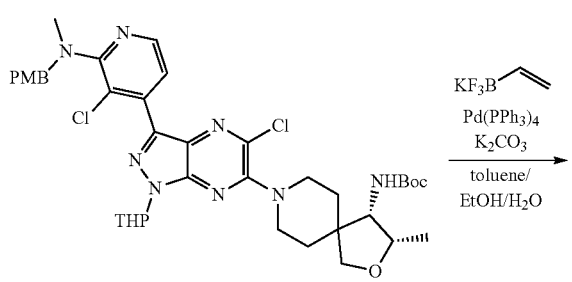

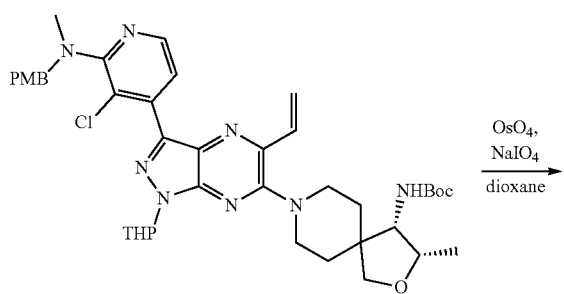

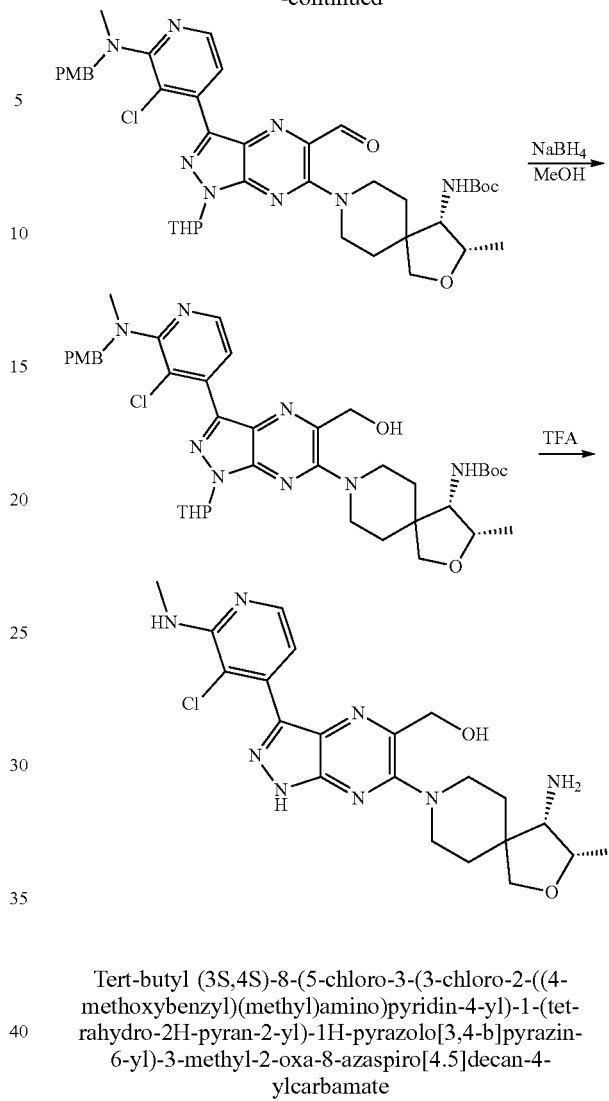

Tert-butyl (3S,4S)-8-(5-chloro-3-(3-chloro-2-((4-methoxybenzyl)(methyl)amino)pyridin-4-yl)-1-(tetrahydro-2H-pyran-2-yl)-1H-pyrazolo[3,4-b]pyrazin-6-yl)-3-methyl-2-oxa-8-azaspiro[4.5]decan-4-ylcarbamate To a solution of tert-butyl (3S,4S)-8-(5-chloro-3-iodo-1-(tetrahydro-2H-pyran-2-yl)-1H-pyrazolo[3,4-b]pyrazin-6-yl)-3-methyl-2-oxa-8-azaspiro[4.5]decan-4-ylcarbamate (220 mg, 0.347 mmol) in toluene (3 mL), EtOH (1.5 mL), and water (1 mL) were added 3-chloro-2-((4-methoxybenzyl)(methyl)amino)pyridin-4-ylboronic acid (212 mg, 0695 mmol), Pd(Ph$_3$P)$_4$ (40 mg, 0.035 mmol), KF (60 mg, 1.043 mmol), and K$_3$PO$_4$ (221 mg, 1.043 mmol) and the resulting mixture was heated to 120° C. for 18 hours. The volitiles were removed under reduced pressure and the residue was purified via silica gel chromatography (0-100% EtOAc in hexanes) to give the title compound as a brown solid (150 mg, 0.195 mmol, 75% yield). MS (ES+) C38H48Cl2N8O5 requires: 766, found: 767 [M+H]$^+$.

Tert-butyl (3S,4S)-8-(3-(3-chloro-2-((4-methoxybenzyl)(methyl)amino)pyridin-4-yl)-1-(tetrahydro-2H-pyran-2-yl)-5-vinyl-1H-pyrazolo[3,4-b]pyrazin-6-yl)-3-methyl-2-oxa-8-azaspiro[4.5]decan-4-ylcarbamate To a solution of tert-butyl (3S,4S)-8-(5-chloro-3-(3-chloro-2-((4-methoxybenzyl)(methyl)amino)pyridin-4-yl)-1-(tetrahydro-2H-pyran-2-yl)-1H-pyrazolo[3,4-b]pyrazin- 6-yl)-3-methyl-2-oxa-8-azaspiro[4.5]decan-4-ylcarbamate (190 mg, 0.2477 mmol) in toluene (2 mL), EtOH (1 mL), and H₂O (0.5 mL) were added potassium vinyltrifluoroborate (43 mg, 0.322 mmol), Pd(Ph₃P)₄ (28.6 mg, 0.025 mmol), K₂CO₃ (102 mg, 0.743 mmol) and the resulting mixture was heated to 120° C. for 1 hour. The volitiles were removed under reduced pressure and the residue was purified via silica gel chromatography (0-100% EtOAc in hexanes) to give the title compound as a brown solid (120 mg, 0.158 mmol, 63% yield). MS (ES+) C40H51ClN8O5 requires: 758, found: 759 [M+H]⁺.

Tert-butyl (3S,4S)-8-(3-(3-chloro-2-((4-methoxybenzyl)(methyl)amino)pyridin-4-yl)-5-formyl-1-(tetrahydro-2H-pyran-2-yl)-1H-pyrazolo[3,4-b]pyrazin-6-yl)-3-methyl-2-oxa-8-azaspiro[4.5]decan-4-ylcarbamate To a solution of tert-butyl (3S,4S)-8-(3-(3-chloro-2-((4-methoxybenzyl)(methyl)amino)pyridin-4-yl)-1-(tetrahydro-2H-pyran-2-yl)-5-vinyl-1H-pyrazolo[3,4-b]pyrazin-6-yl)-3-methyl-2-oxa-8-azaspiro[4.5]decan-4-ylcarbamate (120 mg, 0.158 mmol) in dioxane (4 ml) was added 2,6-dimethylpyridine (51 mg, 0.474 mmol), NaIO₄ (135 mg, 0.632 mmol in H₂O (1 ml)), and OsO₄ (0.27 mg, 0.001 mmol) and the resulting mixture was stirred at 25° C. for 1 hour. The reaction mixture was diluted with EtOAc (25 mL), H₂O (25 mL) was added, and the layers were separated. The aqueous phase was extracted with EtOAc (3×25 mL), the combined organic layers were washed with sat NaCl, dried over Na₂SO₄, filtered and concentrated under reduced pressure to give the title compound as an oil (120 mg, 0.197 mmol, 99% yield). The product was used without further purification. MS (ES+) C39H49ClN8O6 requires: 760, found: 761 [M+H]⁺.

Tert-butyl (3S,4S)-8-(3-(3-chloro-2-((4-methoxybenzyl)(methyl)amino)pyridin-4-yl)-5-(hydroxymethyl)-1-(tetrahydro-2H-pyran-2-yl)-1H-pyrazolo[3,4-b]pyrazin-6-yl)-3-methyl-2-oxa-8-azaspiro[4.5]decan-4-ylcarbamate To a 0° C. solution of tert-butyl (3S,4S)-8-(3-(3-chloro-2-((4-methoxybenzyl)(methyl)amino)pyridin-4-yl)-5-formyl-1-(tetrahydro-2H-pyran-2-yl)-1H-pyrazolo[3,4-b]pyrazin-6-yl)-3-methyl-2-oxa-8-azaspiro[4.5]decan-4-ylcarbamate (150 mg, 0.197 mmol) in MeOH (5 mL) was added NaBH₄ (15 mg, 0.394 mmol) and the resulting mixture was stirred at 0° C. for 30 min. Sat NaCl (50 mL) was added, and the layers were separated. The aqueous phase was extracted with EtOAc (3×25 mL), the combined organic layers were washed with sat NaCl, dried over Na₂SO₄, filtered and concentrated under reduced pressure to give the title compound as a brown oil (100 mg, 0.132 mmol, 67% yield). The product was used without further purification. MS (ES+) C39H51ClN8O6 requires: 762, found: 763 [M+H]⁺.

(6-((3S,4S)-4-Amino-3-methyl-2-oxa-8-azaspiro[4.5]decan-8-yl)-3-(3-chloro-2-(methylamino)pyridin-4-yl)-1H-pyrazolo[3,4-b]pyrazin-5-yl)methanol To tert-butyl (3S,4S)-8-(3-(3-chloro-2-((4-methoxybenzyl)(methyl)amino)pyridin-4-yl)-5-(hydroxymethyl)-1-(tetrahydro-2H-pyran-2-yl)-1H-pyrazolo[3,4-b]pyrazin-6-yl)-3-methyl-2-oxa-8-azaspiro[4.5]decan-4-ylcarbamate (100 mg, 0.132 mmol) was added TFA (5 mL) and the resulting mixture was stirred at 25° C. for 1 hour. The volitiles were removed under reduced pressure and the residue was purified by reverse phase preparative HPLC (Mobile phase: A=0.1% TFA/H₂O, B=0.1% TFA/MeCN; Gradient: B=10-90%; 12 min; Column: C18) to give the title compound as a light brown solid (11 mg, 0.019 mmol, 14% yield). MS (ES+) C26H35ClN8O4 requires:558, found: 559 [M+H]⁺. ¹H NMR (500 MHz, MeOD) δ 8.01 (d, J=6.3 Hz, 1H), 7.59 (d, J=6.3 Hz, 1H), 4.82 (s, 2H), 4.41-4.23 (m, 1H), 4.01 (d, J=9.2 Hz, 1H), 3.93-3.71 (m, 3H), 3.51 (d, J=4.1 Hz, 1H), 3.23-3.03 (m, 5H), 2.19-1.87 (m, 3H), 1.81 (d, J=12.7 Hz, 1H), 1.36 (d, J=6.5 Hz, 3H).

The following examples were synthesized with synthetic methods that were similar to that used for the above Examples, and can generally be made by methods disclosed herein. The Examples may be made as free bases or as salts.

| Example | Name | Structure | Charaterization |
|---|---|---|---|
| 21 | (6-((3S,4S)-4-amino-3-methyl-2-oxa-8-azaspiro[4.5]decan-8-yl)-3-(2-chloro-3-(oxetan-3-yloxy)phenyl)-1H-pyrazolo[3,4-b]pyrazin-5-yl)methanol | 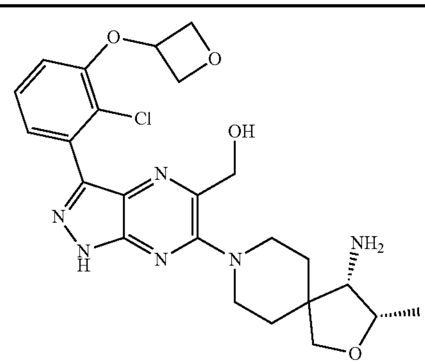 | 1H NMR (500 MHz, MeOD) δ 7.38 (t, J = 7.9 Hz, 1H), 7.35-7.09 (m, 1H), 6.85 (dd, J = 8.2, 1.3 Hz, 1H), 5.47-5.39 (m, 1H), 5.10 (t, J = 6.8 Hz, 2H), 4.81-4.73 (m, 4H), 4.34 (dd, J = 6.5, 4.1 Hz, 1H), 4.01 (d, J = 9.2 Hz, 1H), 3.95-3.69 (m, 3H), 3.50 (d, J = 4.0 Hz, 1H), 3.22-3.00 (m, 2H), 2.14-1.85 (m, 3H), 1.80 (d, J = 12.9 Hz, 1H), 1.35 (d, J = 6.5 Hz, 3H). MS (ES+) C24H29ClN6O4 requires: 500, found: 501 [M + H]⁺. |

| Example | Name | Structure | Charaterization |
|---|---|---|---|
| 22 | (6-((3S,4S)-4-amino-3-methyl-2-oxa-8-azaspiro[4.5]decan-8-yl)-3-(3-chloro-2-(oxetan-3-yloxy)pyridin-4-yl)-1H-pyrazolo[3,4-b]pyrazin-5-yl)methanol | 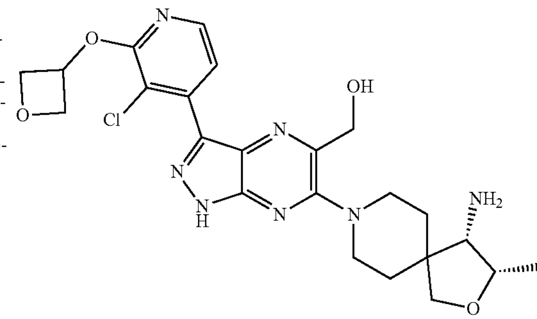 | $^1$H NMR (500 MHz, MeOD) δ 8.64 (d, J = 6.7 Hz, 1H), 8.47 (d, J = 6.8 Hz, 1H), 5.58 (dd, J = 9.4, 6.9 Hz, 1H), 5.15-5.00 (m, 1H), 4.95 (dd, J = 12.2, 6.9 Hz, 1H), 4.30-3.56 (m, 7H), 3.38 (t, J = 13.2 Hz, 1H), 3.13-2.88 (m, 2H), 2.04-1.58 (m, 4H), 1.24 (d, J = 6.5 Hz, 3H). MS (ES+) C23H28ClN7O4 requires: 501, found: 502 [M + H]$^+$. |

Example 23: 2-(4-(6-03S,4S)-4-amino-3-methyl-2-oxa-8-azaspiro[4.5]decan-8-yl)-5-(hydroxymethyl)-1H-pyrazolo[3,4-b]pyrazin-3-yl)-3-chloropyridin-2-yloxy)propane-1,3-diol

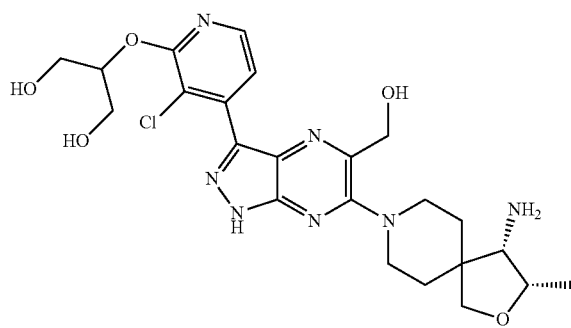 [SMILES: C[C@@H]1OCC2(CCN(c3nc4[nH]nc(-c5ccnc(OC(CO)CO)c5Cl)c4nc3CO)CC2)[C@@H]1N]

2-((4-(6-((3S,4S)-4-amino-3-methyl-2-oxa-8-azaspiro[4.5]decan-8-yl)-5-(hydroxymethyl)-1H-pyrazolo[3,4-b]pyrazin-3-yl)-3-chloropyridin-2-yl)oxy)propane-1,3-diol To (6-((3S,4S)-4-amino-3-methyl-2-oxa-8-azaspiro[4.5]decan-8-yl)-3-(3-chloro-2-(oxetan-3-yloxy)pyridin-4-yl)-1H-pyrazolo[3,4-b]pyrazin-5-yl)methanol (30 mg, 0.059 mmol) was added TFA (3 ml) and the resulting mixture was stirred at 25° C. for 1 hour. The volitiles were removed under reduced pressure. The residue dissolve in MeOH (3 ml) and K$_2$CO$_3$ (30 mg) was added and the resulting mixture was stirred at 25° C. for 15 min. The mixture was filtered and the residue was purified by reverse phase preparative HPLC (Mobile phase: A=0.1% TFA/H$_2$O, B=0.1% TFA/MeCN; Gradient: B=10-90%; 12 min; Column: C18) to give the title compound as a light brown solid (9 mg, 0.017 mmol, 3.4% yield). MS (ES+) C23H30ClN7O5 requires: 519, found: 520 [M+H]+. $^1$H NMR (500 MHz, MeOD) δ 7.72 (d, J=7.1 Hz, 1H), 6.95 (d, J=7.0 Hz, 1H), 4.80 (s, 2H), 4.50 (dd, J=13.2, 3.4 Hz, 1H), 4.34 (dd, J=6.5, 4.2 Hz, 1H), 4.19-3.69 (m, 6H), 3.63 (d, J=5.4 Hz, 2H), 3.49 (t, J=10.0 Hz, 1H), 3.25-2.98 (m, 2H), 2.02 (dt, J=30.1, 13.2 Hz, 3H), 1.80 (d, J=12.4 Hz, 1H), 1.35 (d, J=6.5 Hz, 3H).

Biological Activity Assay

The activity of the compounds in the Examples disclosed herein as PTPN11 inhibitors is illustrated in the following assays. Other compounds listed herein, which have not yet been made and/or tested, are predicted to have activity in these assays as well.

PTPN11 Enzymatic Assay

Recombinant full-length wild-type and E76K mutant human PTPN11 proteins were cloned, expressed (*E. coli* system), and isolated via a two-step purification of Ni affinity followed by S75 size exclusion chromatography.

Phosphatase activity of full length wild-type PTPN11 (PTPN11-WT) or PTPN11-E76K mutant enzyme was measured using the fluorogenic 6,8-difluoro-4-methylumbelliferyl phosphate (DiFMUP; Molecular Probes) as the substrate. Enzyme (250 pM) was incubated with or without increasing concentrations of compounds in assay buffer (62.5 mM HEPES, 125 mM NaCl, 1 mM EDTA, 1.25 mM TECP, 0.1% BSA) for 30 min at room temperature. Reaction was initiated by addition of DiFMUP (50 μM) at room temperature in 384-well black plate with a final reaction volume of 20 uL in assay buffer. After 1 hour, DiFMUP fluorescence signal was measured (Ex:340/Em:460) using Envision plate reader. Dose-response curves were analyzed using IC50 regression curve fitting (GeneData Screener). Curves were normalized to a high controls without inhibitor, and low controls without enzyme. Results are given below in Table 1. Other compounds disclosed herein are expected to have activity similar to the results below, showing activity as PTPN11 inhibitors.

pERK AlphaScreen Protocol

KYSE-520 cells (10 k cells/well) were grown in 384-well plate in 20 uL of medium (RPMI-1640, without phenol red, containing 10% FBS) at 37° C. with 5% CO2 overnight. DMSO (control) or increasing concentrations of compounds were diluted in medium, added to the 384-well plate (5 uL/well, final DMSO concentration of 1%), and cells were then incubated with compounds for 2 hr. Phospho-ERK levels were measured using phospho-ERK1/2 AlphaScreen SureFire (PerkinElmer, TGRESB10K) following manufacturer's recommendations. Dose-response curves were analyzed using IC50 regression curve fitting (GeneData Screener). Curves were normalized to a high control without inhibitor (DMSO only), and low control (1 μM selumetinib).

TABLE 10

Biological Activity for inhibition of PTPN11-E76K mutant enzyme and pERK AlphaScreen

| Example | PTPN11-E76K Avg IC$_{50}$ (nM) | pERK Avg IC$_{50}$ (nM) |
|---|---|---|
| 1 | 68 | 93 |
| 2 | 317 | 580 |
| 3 | 960 | 2000 |
| 4 | 465 | NA |
| 5 | 397 | 1967 |
| 6 | 950 | 3820 |
| 7 | 19 | 97 |
| 8 | 90 | NA |
| 9 | 190 | 647 |
| 10 | 277 | 502 |
| 11 | 17 | NA |
| 12 | 372 | 326 |
| 13 | 224 | 704 |
| 14 | 22 | 36 |
| 15 | 1 | 0.4 |
| 16 | 4 | 2 |
| 17 | 6 | 9 |
| 18 | 9 | 20 |
| 19 | 6 | 1 |
| 20 | 3 | 2 |
| 21 | 558 | 2706 |
| 22 | 48 | 3369 |

N.A. = Not Available

Colony Formation Assay

KYSE-520 cells (2000 cells/well) are plated in 6-well plate containing 2 mL of medium (RPMI-1640, containing 10% FBS), in the presence of DMSO (control; 1% final concentration) or increasing compound concentration. After 14 days of culture at 37° C. in a humidified 5% CO2 incubator, colonies are fixed and stained with 0.1% crystal violet and 15% ethanol solution. Plates are imaged and colony area quantified and normalized to DMSO with ImageJ, Colony Area plugin. (Guzman, Camilo, PloS one 2014). Compounds disclosed herein are expected to have activity in inhibiting cellular proliferation and/or colony formation in the foregoing assay.

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of structural Formula I

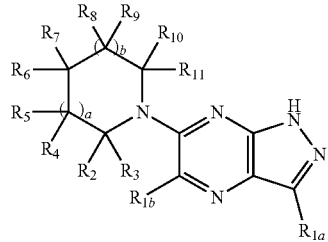

(I)

or a salt or tautomer thereof, wherein:
 a is 0 or 1;
 b is 0 or 1;
 $R_{1a}$ is selected from the group consisting of halo, phenyl, and a 5- to 6-membered heteroaryl group containing 1 to 4 heteroatoms or groups independently selected from the group consisting of N, C(O), O, and S; said phenyl or heteroaryl of $R_{1a}$ is optionally substituted with 1 to 5 $R_{12}$ groups independently selected from the group consisting of halo, hydroxy, amino, $C_{1-4}$ alkylamino, $C_{1-4}$ dialkylamino, cyano, $C_{1-4}$alkyl, $C_{1-4}$alkoxy, $C_{1-4}$hydroxyalkyl, $C_{1-4}$dihydroxyalkyl, hydroxyC$_{1-4}$alkoxy, dihydroxyC$_{1-4}$alkoxy, $C_{1-4}$haloalkyl, $C_{1-4}$aminoalkyl, $C_{3-8}$cycloalkyl, $C_{3-8}$cycloalkenyl, NR$_{15}$C(O)R$_{13}$, NR$_{15}$C(O)OR$_{13}$, NR$_{13}$C(O)NR$_{15}$R$_{16}$, NR$_{15}$S(O)R$_{13}$, NR$_{15}$S(O)$_2$R$_{13}$, C(O)NR$_{15}$R$_{16}$, S(O)NR$_{15}$R$_{16}$, S(O)$_2$NR$_{15}$R$_{16}$, C(O)R$_{13}$, C(O)OR$_{13}$, OR$_{13}$, SR$_{13}$, S(O)R$_{13}$, and S(O)$_2$R$_{13}$;

$R_{1b}$ is selected from the group consisting of halogen and $C_{1-6}$alkyl;

$R_2$, $R_3$, $R_{10}$, and $R_{11}$ are independently selected from the group consisting of hydrogen, $C_{1-4}$ alkyl, and $C_{3-8}$cycloalkyl;

$R_4$, $R_5$, $R_8$, and $R_9$ are independently selected from the group consisting of hydrogen, cyano, $C_{1-4}$ alkyl, $C_{1-4}$alkoxy, amino, hydroxy, $C_{3-8}$cycloalkyl, halo, and $C_{1-4}$alkylamino;

$R_6$ and $R_7$ together with the carbon atom to which they are both attached form a 3- to 7-membered saturated or unsaturated ring that can contain 1 to 3 heteroatoms or groups independently selected from the group consisting of N, C(O), O, and S(O)$_m$, and that is optionally substituted with one $R_{17}$ group, and that is optionally substituted with one or more $R_{18}$ groups;

m is 0, 1, or 2;

any two groups of $R_2$, $R_3$, $R_4$, $R_5$, $R_8$, $R_9$, $R_{10}$ and $R_{11}$ can form a 5- to 6-membered ring, optionally containing a N, O or S heteroatom;

any two groups of $R_2$, $R_4$, $R_8$ and $R_{10}$ can form a direct bond, or a 1 or 2 atom carbon bridge;

$R_{13}$, $R_{15}$, and $R_{16}$ are independently selected from the group consisting of hydrogen, $C_{1-4}$ alkyl, $C_{3-8}$cycloalkyl, and 3- to 6-membered heterocyclyl, wherein said alkyl, cycloalkyl and 3- to 6-membered heterocyclyl is optionally substituted by one or more substituents selected from the group consisting of hydroxy, cyano and halo; and each $R_{17}$ and $R_{18}$ is independently selected from the group consisting of amino, halo, hydroxy, cyano, trifluoromethyl, trifluoromethoxy, $C_{1-4}$ alkyl, and $C_{1-4}$ alkoxy.

2. The compound as recited in claim 1, wherein $R_{1a}$ phenyl or a 5 to 6-membered heteroaryl group containing 1 to 4 heteroatoms or groups independently selected from the group consisting of N, C(O), O, and S;
 said phenyl or heteroaryl of $R_{1a}$ is optionally substituted with 1 to 5 $R_{12}$ groups independently selected from the group consisting of halo, hydroxy, amino, $C_{1-4}$ alkylamino, $C_{1-4}$ dialkylamino, cyano, $C_{1-4}$alkyl, $C_{1-4}$alkoxy, $C_{1-4}$hydroxyalkyl, $C_{1-4}$haloalkyl, $C_{1-4}$aminoalkyl, $C_{3-8}$cycloalkyl, $C_{3-8}$cycloalkenyl, NR$_{15}$C(O)R$_{13}$, NR$_{15}$C(O)OR$_{13}$, NR$_{13}$C(O)NR$_{15}$R$_{16}$, NR$_{15}$S(O)R$_{13}$, NR$_{15}$S(O)$_2$R$_{13}$, C(O)NR$_{15}$R$_{16}$, S(O)NR$_{15}$R$_{16}$, S(O)$_2$NR$_{15}$R$_{16}$, C(O)R$_{13}$, C(O)OR$_{13}$, SR$_{13}$, S(O)R$_{13}$, and S(O)$_2$R$_{13}$; and $R_{13}$, $R_{15}$, and $R_{16}$ are independently selected from the group consisting of hydrogen, $C_{1-4}$alkyl, $C_{3-8}$cycloalkyl, wherein said alkyl or cycloalkyl is optionally substituted by one or more substituents selected from the group consisting of hydroxy, cyano and halo.

3. The compound as recited in claim 1, wherein $R_2$, $R_3$, $R_4$, $R_5$, $R_8$, $R_9$, $R_{10}$ and $R_{11}$ are each hydrogen.

4. The compound as recited in claim 1, wherein $R_6$ and $R_7$ together with the carbon atom to which they are both attached forms a 3- to 7-membered saturated or unsaturated ring that contains 1 to 3 heteroatoms or groups independently selected from the group consisting of N, C(O), O, and $S(O)_m$, and that is optionally substituted with one $R_{17}$ group, and that is optionally substituted with one or more $R_{18}$ groups.

5. The compound as recited in claim 1, wherein $R_6$ and $R_7$ together with the carbon atom to which they are both attached form a 3- to 6-membered heterocycloalkyl ring that is optionally substituted with one $R_{17}$ group, and that is optionally substituted with one or more $R_{18}$ groups.

6. The compound as recited in claim 1, wherein each $R_{17}$ is amino; and each $R_{18}$ is methyl.

7. The compound as recited in claim 1, wherein $R_{1a}$ is selected from the group consisting of:

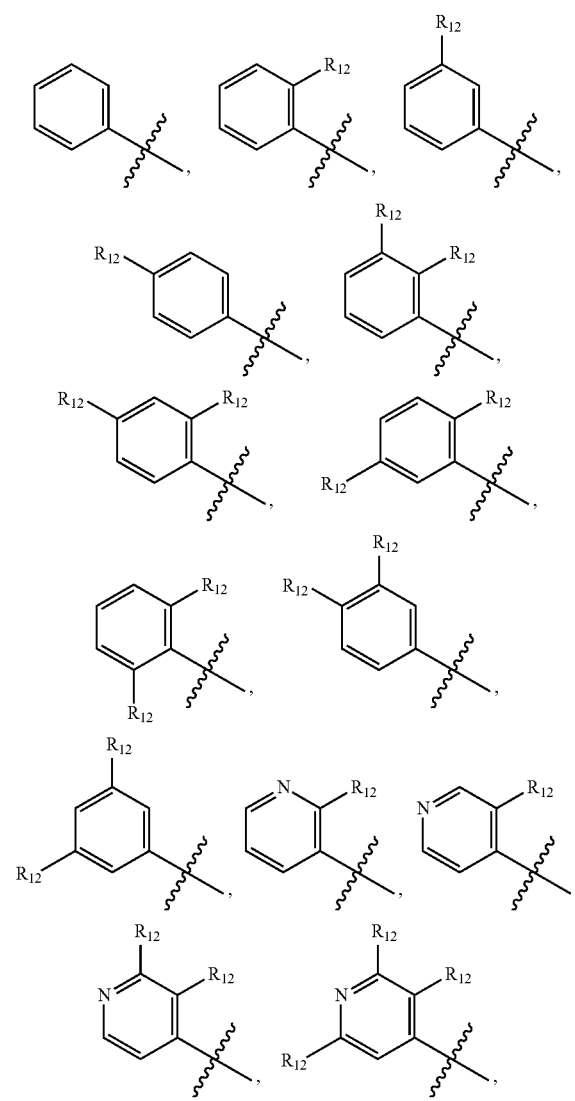

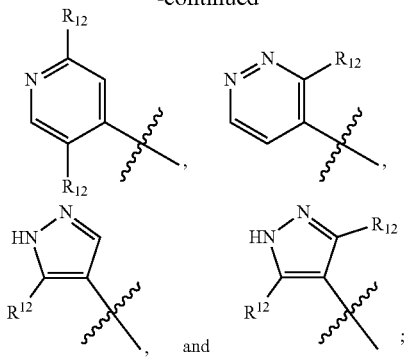

and
each $R_{12}$ is independently selected from the group consisting of halo, hydroxy, amino, $C_{1-4}$alkylamino, $C_{1-4}$dialkylamino, cyano, $C_{1-4}$alkyl, and $C_{1-4}$alkoxy.

8. The compound as recited in claim 7, wherein each $R_{12}$ is independently selected from the group consisting of halo, amino, methylamino, and ethylamino.

9. The compound as recited in claim 1, wherein $R_{1a}$ is phenyl or pyridyl, each of which is substituted with 0 to 2 $R_{12}$.

10. The compound as recited in claim 1, wherein $R_{1b}$ is halogen.

11. The compound as recited in claim 10, wherein $R_{1b}$ is chloro.

12. The compound as recited in claim 1, wherein $R_{1b}$ is $C_{1-6}$alkyl.

13. The compound as recited in claim 12, wherein $R_{1b}$ is methyl.

14. The compound as recited in claim 1, having a structure selected from the group consisting of:

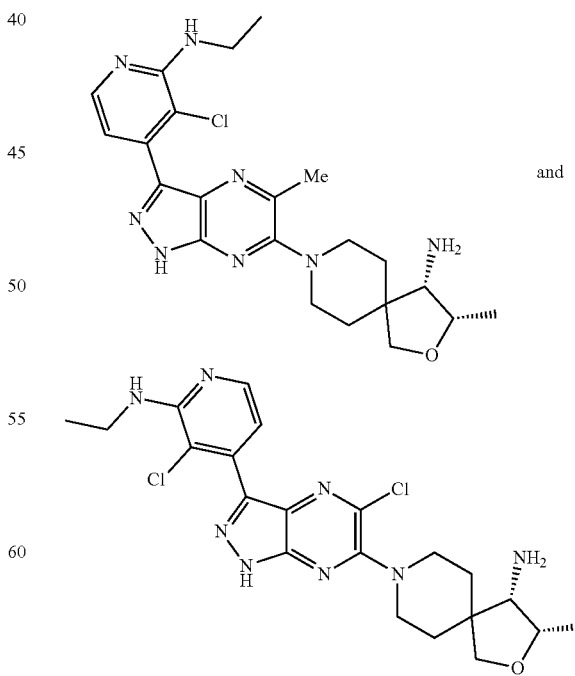

or a salt or tautomer thereof.

15. A pharmaceutical composition comprising a compound as recited in claim 1, together with a pharmaceutically acceptable carrier.

16. A method of treatment of a PTPN11-mediated disease comprising the administration of a therapeutically effective amount of a compound as recited in claim 1, to a patient in need thereof.

17. The method as recited in claim 16, wherein the disease is cancer.

18. The method as recited in claim 17, wherein the cancer is selected from the group consisting of breast cancer, colon cancer, leukemia, and melanoma.

* * * * *